United States Patent
Puno

(10) Patent No.: US 10,835,386 B2
(45) Date of Patent: Nov. 17, 2020

(54) INTER-BODY IMPLANTATION SYSTEM AND METHOD

(71) Applicant: R Tree Innovations, LLC, Prospect, KY (US)

(72) Inventor: Rolando M. Puno, Prospect, KY (US)

(73) Assignee: R Tree Innovations, LLC, Prospect, KY (US)

( * ) Notice: Subject to any disclaimer, the term of this patent is extended or adjusted under 35 U.S.C. 154(b) by 252 days.

(21) Appl. No.: 15/810,829

(22) Filed: Nov. 13, 2017

(65) Prior Publication Data

US 2018/0064558 A1  Mar. 8, 2018

Related U.S. Application Data

(63) Continuation of application No. 12/833,342, filed on Jul. 9, 2010, now Pat. No. 9,814,599.

(Continued)

(51) Int. Cl.
*A61F 2/44* (2006.01)
*A61B 17/17* (2006.01)
(Continued)

(52) U.S. Cl.
CPC ........ *A61F 2/4465* (2013.01); *A61B 17/1757* (2013.01); *A61F 2/4611* (2013.01); *A61F 2/4684* (2013.01); *A61B 17/708* (2013.01); *A61F 2/46* (2013.01); *A61F 2002/2835* (2013.01); *A61F 2002/305* (2013.01); *A61F 2002/3008* (2013.01); *A61F 2002/30056* (2013.01); *A61F 2002/30092* (2013.01); *A61F 2002/30133* (2013.01); *A61F 2002/30365* (2013.01); *A61F 2002/30462* (2013.01); *A61F 2002/30492* (2013.01); *A61F 2002/30538* (2013.01); *A61F 2002/30571* (2013.01); *A61F 2002/30579* (2013.01); *A61F 2002/30594* (2013.01); *A61F 2002/30624* (2013.01); *A61F 2002/30632* (2013.01); *A61F 2002/30672* (2013.01); *A61F 2002/30808* (2013.01);
(Continued)

(58) Field of Classification Search
CPC ...................... A61F 2002/4415; A61F 2/4465
See application file for complete search history.

(56) References Cited

U.S. PATENT DOCUMENTS

| | | |
|---|---|---|
| 609,366 A | 8/1898 | Potter |
| 2,029,495 A | 2/1936 | Lowe |

(Continued)

FOREIGN PATENT DOCUMENTS

| | | |
|---|---|---|
| DE | 19710392 C1 | 7/1999 |
| EP | 637439 A1 | 2/1995 |

(Continued)

*Primary Examiner* — Olivia C Chang
(74) *Attorney, Agent, or Firm* — Lerner, David, Littenberg, Krumholz & Mentlik, LLP

(57) ABSTRACT

A system for implanting an inter-body device between adjacent vertebrae comprises an inter-body device having a plurality of cans secured to a flexible bridge and having a relief portion therebetween. An inserter tube and complementary bullnoses are advantageously secured to the vertebrae by an extension arm for securing the assembly precisely in place. A plurality of articulating trial implants are provided to test fit a disc space for the proper sized inter-body device.

22 Claims, 73 Drawing Sheets

Related U.S. Application Data

(60) Provisional application No. 61/224,333, filed on Jul. 9, 2009.

(51) Int. Cl.
*A61F 2/46* (2006.01)
*A61B 17/70* (2006.01)
*A61F 2/28* (2006.01)
*A61F 2/30* (2006.01)

(52) U.S. Cl.
CPC ............. *A61F 2002/30879* (2013.01); *A61F 2002/30892* (2013.01); *A61F 2002/448* (2013.01); *A61F 2002/4415* (2013.01); *A61F 2002/4627* (2013.01); *A61F 2002/4629* (2013.01); *A61F 2210/0014* (2013.01); *A61F 2220/0025* (2013.01); *A61F 2220/0033* (2013.01); *A61F 2220/0075* (2013.01); *A61F 2230/0015* (2013.01); *A61F 2250/0006* (2013.01); *A61F 2250/0032* (2013.01); *A61F 2250/0098* (2013.01); *A61F 2310/00023* (2013.01)

(56) References Cited

U.S. PATENT DOCUMENTS

| | | | |
|---|---|---|---|
| 2,465,305 A | 3/1949 | Cope |
| 3,848,601 A | 11/1974 | Ma et al. |
| 4,239,045 A | 12/1980 | Schlein |
| 4,481,943 A | 11/1984 | Michelson |
| 4,566,466 A | 1/1986 | Ripple et al. |
| 4,697,586 A | 10/1987 | Gazale |
| D295,318 S | 4/1988 | Gazale |
| 4,736,738 A | 4/1988 | Lipovsek et al. |
| 4,881,534 A | 11/1989 | Uhl et al. |
| 4,908,892 A | 3/1990 | Michelson |
| 4,949,435 A | 8/1990 | Michelson |
| 4,957,495 A | 9/1990 | Kluger |
| 4,959,058 A | 9/1990 | Michelson |
| 4,968,298 A | 11/1990 | Michelson |
| 4,973,321 A | 11/1990 | Michelson |
| 4,985,019 A | 1/1991 | Michelson |
| 5,009,661 A | 4/1991 | Michelson |
| 5,015,247 A | 5/1991 | Michelson |
| 5,026,386 A | 6/1991 | Michelson |
| 5,052,373 A | 10/1991 | Michelson |
| 5,059,194 A | 10/1991 | Michelson |
| 5,135,210 A | 8/1992 | Michelson |
| 5,195,526 A | 3/1993 | Michelson |
| 5,195,541 A | 3/1993 | Obenchain |
| 5,250,061 A | 10/1993 | Michelson |
| 5,423,842 A | 6/1995 | Michelson |
| 5,425,772 A | 6/1995 | Brantigan |
| 5,451,227 A | 9/1995 | Michaelson |
| 5,484,437 A | 1/1996 | Michelson |
| 5,531,749 A | 7/1996 | Michelson |
| 5,562,736 A | 10/1996 | Ray et al. |
| 5,626,266 A | 5/1997 | Michelson |
| D381,746 S | 7/1997 | Koros et al. |
| 5,649,945 A | 7/1997 | Ray et al. |
| 5,662,300 A | 9/1997 | Michelson |
| 5,722,977 A | 3/1998 | Wilhelmy |
| 5,782,830 A | 7/1998 | Farris |
| 5,788,701 A | 8/1998 | McCue |
| D401,335 S | 11/1998 | Koros et al. |
| 5,851,214 A | 12/1998 | Larsen et al. |
| 6,004,326 A | 12/1999 | Castro et al. |
| 6,032,309 A | 3/2000 | Michelson |
| 6,063,088 A | 5/2000 | Winslow |
| 6,083,225 A | 7/2000 | Winslow et al. |
| 6,096,038 A | 8/2000 | Michelson |
| 6,110,177 A | 8/2000 | Ebner et al. |
| 6,126,664 A | 10/2000 | Troxell et al. |
| 6,129,740 A | 10/2000 | Michelson |
| 6,142,997 A | 11/2000 | Michelson |
| D437,055 S | 1/2001 | Michelson |
| 6,174,311 B1 | 1/2001 | Branch et al. |
| 6,175,962 B1 | 1/2001 | Michelson |
| 6,193,721 B1 | 2/2001 | Michelson |
| 6,193,757 B1 | 2/2001 | Foley et al. |
| 6,200,322 B1 | 3/2001 | Branch et al. |
| 6,206,923 B1 | 3/2001 | Boyd |
| D440,311 S | 4/2001 | Michelson |
| D442,691 S | 5/2001 | Michelson |
| 6,224,607 B1 | 5/2001 | Michelson |
| 6,257,459 B1 | 7/2001 | Michelson et al. |
| 6,258,094 B1 | 7/2001 | Nicholson et al. |
| 6,261,295 B1 | 7/2001 | Nicholson et al. |
| 6,269,974 B1 | 8/2001 | Michelson et al. |
| 6,290,724 B1 | 9/2001 | Marino |
| D449,692 S | 10/2001 | Michelson |
| 6,299,030 B1 | 10/2001 | Michelson et al. |
| 6,302,914 B1 | 10/2001 | Michelson |
| D450,122 S | 11/2001 | Michelson |
| 6,318,602 B1 | 11/2001 | Michelson et al. |
| 6,332,887 B1 | 12/2001 | Knox |
| 6,338,309 B1 | 1/2002 | Michelson |
| D454,197 S | 3/2002 | Michelson |
| D454,953 S | 3/2002 | Michelson |
| 6,364,880 B1 | 4/2002 | Michelson |
| 6,370,694 B1 | 4/2002 | Michelson |
| D457,242 S | 5/2002 | Michelson |
| 6,383,186 B1 | 5/2002 | Michelson |
| 6,383,188 B2 | 5/2002 | Kuslich et al. |
| 6,387,130 B1 | 5/2002 | Stone et al. |
| 6,395,031 B1 | 5/2002 | Foley et al. |
| D460,188 S | 7/2002 | Michelson |
| D460,189 S | 7/2002 | Michelson |
| 6,436,098 B1 | 8/2002 | Michelson |
| 6,436,101 B1 | 8/2002 | Hamada |
| D463,560 S | 9/2002 | Michelson |
| 6,454,771 B1 | 9/2002 | Michelson |
| 6,500,180 B1 | 12/2002 | Foley et al. |
| 6,506,151 B2 | 1/2003 | Estes et al. |
| 6,514,260 B1 | 2/2003 | Zdeblick et al. |
| 6,517,544 B1 | 2/2003 | Michelson |
| 6,537,280 B2 | 3/2003 | Dinger et al. |
| 6,537,320 B1 | 3/2003 | Michelson |
| 6,554,836 B2 | 4/2003 | Michelson |
| 6,561,194 B2 | 5/2003 | Michelson |
| 6,565,574 B2 | 5/2003 | Michelson |
| 6,575,899 B1 | 6/2003 | Foley et al. |
| 6,575,977 B1 | 6/2003 | Michelson |
| 6,575,981 B1 | 6/2003 | Boyd et al. |
| 6,579,318 B2 | 6/2003 | Varga et al. |
| 6,595,996 B2 | 7/2003 | Dinger et al. |
| 6,599,291 B1 | 7/2003 | Foley et al. |
| 6,609,322 B1 | 8/2003 | Michelson |
| 6,610,065 B1 | 8/2003 | Branch et al. |
| 6,610,089 B1 | 8/2003 | Liu et al. |
| 6,613,090 B2 | 9/2003 | Fuss et al. |
| 6,616,666 B1 | 9/2003 | Michelson |
| 6,620,162 B2 | 9/2003 | Kuslich et al. |
| 6,620,163 B1 | 9/2003 | Michelson |
| 6,620,196 B1 | 9/2003 | Trieu |
| 6,635,060 B2 | 10/2003 | Hanson et al. |
| 6,635,062 B2 | 10/2003 | Ray, III et al. |
| 6,641,582 B1 | 11/2003 | Hanson et al. |
| 6,648,891 B2 | 11/2003 | Kim |
| 6,652,534 B2 | 11/2003 | Zucherman et al. |
| 6,656,178 B1 | 12/2003 | Veldhuizen et al. |
| 6,679,887 B2 | 1/2004 | Nicholson et al. |
| 6,695,849 B2 | 2/2004 | Michelson |
| 6,712,818 B1 | 3/2004 | Michelson |
| 6,719,794 B2 | 4/2004 | Gerber et al. |
| 6,730,127 B2 | 5/2004 | Michelson |
| 6,740,087 B2 | 5/2004 | Knox |
| 6,764,491 B2 | 7/2004 | Frey et al. |
| 6,767,367 B1 | 7/2004 | Michelson |
| 6,770,074 B2 | 8/2004 | Michelson |
| 6,770,094 B2 | 8/2004 | Fehling et al. |
| 6,811,474 B2 | 11/2004 | Cherian et al. |
| 6,824,565 B2 | 11/2004 | Muhanna et al. |

(56) References Cited

U.S. PATENT DOCUMENTS

| | | |
|---|---|---|
| 6,830,570 B1 | 12/2004 | Frey et al. |
| 6,833,006 B2 | 12/2004 | Foley et al. |
| 6,840,941 B2 | 1/2005 | Rogers et al. |
| 6,852,127 B2 | 2/2005 | Varga et al. |
| 6,855,148 B2 | 2/2005 | Foley et al. |
| 6,893,466 B2 | 5/2005 | Trieu |
| 6,913,621 B2 | 7/2005 | Boyd et al. |
| 6,916,320 B2 | 7/2005 | Michelson |
| 6,923,830 B2 | 8/2005 | Michelson |
| 6,926,718 B1 | 8/2005 | Michelson |
| 6,929,606 B2 | 8/2005 | Ritland |
| 6,929,647 B2 | 8/2005 | Cohen |
| 6,951,538 B2 | 10/2005 | Ritland |
| 6,962,606 B2 | 11/2005 | Michelson |
| 6,966,912 B2 | 11/2005 | Michelson |
| 6,969,390 B2 | 11/2005 | Michelson |
| 6,969,405 B2 | 11/2005 | Suddaby |
| 6,972,019 B2 | 12/2005 | Michelson |
| 6,974,480 B2 | 12/2005 | Messerli et al. |
| 6,989,031 B2 | 1/2006 | Michelson |
| 6,991,654 B2 | 1/2006 | Foley |
| 7,011,663 B2 | 3/2006 | Michelson |
| 7,014,638 B2 | 3/2006 | Michelson |
| 7,018,416 B2 | 3/2006 | Hanson et al. |
| 7,025,787 B2 | 4/2006 | Bryan et al. |
| 7,033,362 B2 | 4/2006 | McGahan et al. |
| 7,033,392 B2 | 4/2006 | Schmiel et al. |
| 7,037,339 B2 | 5/2006 | Houfburg |
| 7,041,107 B2 | 5/2006 | Pohjonen et al. |
| 7,056,342 B2 | 6/2006 | Michelson |
| 7,060,073 B2 | 6/2006 | Frey et al. |
| 7,063,701 B2 | 6/2006 | Michelson |
| 7,063,702 B2 | 6/2006 | Michelson |
| 7,063,725 B2 | 6/2006 | Foley |
| 7,070,070 B2 | 7/2006 | Michelson et al. |
| 7,077,844 B2 | 7/2006 | Michelson |
| 7,083,625 B2 | 8/2006 | Berry |
| 7,094,239 B1 | 8/2006 | Michelson |
| 7,108,416 B1 | 9/2006 | Osawa |
| 7,112,224 B2 | 9/2006 | Liu et al. |
| 7,125,424 B2 | 10/2006 | Banick et al. |
| 7,125,425 B2 | 10/2006 | Foley et al. |
| 7,163,561 B2 | 1/2007 | Michelson |
| 7,166,110 B2 | 1/2007 | Yundt |
| 7,169,152 B2 | 1/2007 | Foley et al. |
| 7,179,262 B2 | 2/2007 | Bryan et al. |
| 7,179,263 B2 | 2/2007 | Zdeblick et al. |
| 7,182,783 B2 | 2/2007 | Trieu |
| 7,204,851 B2 | 4/2007 | Trieu et al. |
| 7,207,991 B2 | 4/2007 | Michelson |
| 7,211,085 B2 | 5/2007 | Michelson |
| 7,223,292 B2 | 5/2007 | Messerli et al. |
| 7,226,483 B2 | 6/2007 | Gerber et al. |
| 7,235,082 B2 | 6/2007 | Bartish et al. |
| 7,247,169 B1 | 7/2007 | Lo et al. |
| 7,264,622 B2 | 9/2007 | Michelson |
| 7,267,692 B2 | 9/2007 | Fortin et al. |
| 7,297,147 B2 | 11/2007 | Michelson |
| 7,309,359 B2 | 12/2007 | Trieu et al. |
| 7,318,839 B2 | 1/2008 | Malberg et al. |
| 7,320,688 B2 | 1/2008 | Foley et al. |
| 7,371,233 B2 | 5/2008 | Swanson et al. |
| 7,396,360 B2 | 7/2008 | Lieberman |
| 7,410,501 B2 | 8/2008 | Michelson |
| 7,435,262 B2 | 10/2008 | Michelson |
| 7,442,209 B2 | 10/2008 | Michelson |
| 7,445,636 B2 | 11/2008 | Michelson |
| 7,445,637 B2 | 11/2008 | Taylor |
| 7,452,359 B1 | 11/2008 | Michelson |
| 7,465,317 B2 | 12/2008 | Malberg et al. |
| 7,470,273 B2 | 12/2008 | Dougherty-Shah |
| 7,476,226 B2 | 1/2009 | Weikel et al. |
| 7,476,252 B2 | 1/2009 | Foley |
| 7,479,160 B2 | 1/2009 | Branch et al. |
| 7,481,413 B2 | 1/2009 | Funari |
| 7,481,812 B2 | 1/2009 | Frey et al. |
| 7,500,977 B2 | 3/2009 | Assell et al. |
| 7,500,991 B2 | 3/2009 | Bartish, Jr. et al. |
| 7,503,936 B2 | 3/2009 | Trieu |
| 7,507,242 B2 | 3/2009 | Triplett et al. |
| 7,507,243 B2 | 3/2009 | Lambrecht et al. |
| 7,520,900 B2 | 4/2009 | Trieu |
| 7,534,254 B1 | 5/2009 | Michelson |
| 7,547,306 B2 | 6/2009 | Michelson |
| 7,559,942 B2 | 7/2009 | Paul et al. |
| 7,569,057 B2 | 8/2009 | Liu et al. |
| 7,575,580 B2 | 8/2009 | Lim et al. |
| 7,578,820 B2 | 8/2009 | Moore et al. |
| 7,588,578 B2 | 9/2009 | Triplett et al. |
| 7,597,695 B2 | 10/2009 | Schmiel et al. |
| 7,611,536 B2 | 11/2009 | Michelson |
| 7,615,079 B2 | 11/2009 | Flickinger et al. |
| 7,618,454 B2 | 11/2009 | Bentley et al. |
| 7,625,374 B2 | 12/2009 | Branch et al. |
| 7,625,381 B2 | 12/2009 | Michelson |
| 7,632,312 B2 | 12/2009 | Leclercq |
| 7,637,953 B2 | 12/2009 | Branch et al. |
| 7,651,497 B2 | 1/2010 | Michelson |
| 7,655,027 B2 | 2/2010 | Michelson |
| 7,686,805 B2 | 3/2010 | Michelson |
| 7,691,148 B2 | 4/2010 | Michelson |
| 7,704,250 B2 | 4/2010 | Michelson |
| 7,704,255 B2 | 4/2010 | Michelson |
| 7,708,779 B2 | 5/2010 | Edie |
| 7,740,630 B2 | 6/2010 | Michelson |
| 7,758,581 B2 | 7/2010 | Chervitz et al. |
| 7,758,647 B2 | 7/2010 | Amin et al. |
| 7,771,479 B2 | 8/2010 | Humphreys et al. |
| 7,780,731 B2 | 8/2010 | Marnay et al. |
| 7,789,914 B2 | 9/2010 | Michelson |
| 7,794,501 B2 | 9/2010 | Edie et al. |
| 7,803,157 B2 | 9/2010 | Michelson |
| 7,803,188 B2 | 9/2010 | Justis et al. |
| 7,806,932 B2 | 10/2010 | Webb et al. |
| 7,811,285 B2 | 10/2010 | Michelson |
| 7,828,800 B2 | 11/2010 | Michelson |
| 7,853,406 B2 | 12/2010 | Michelson et al. |
| 7,857,856 B2 | 12/2010 | Trieu |
| 7,875,034 B2 | 1/2011 | Josse et al. |
| 7,887,565 B2 | 2/2011 | Michelson |
| 7,901,458 B2 | 3/2011 | DeRidder et al. |
| 9,814,599 B2 | 11/2017 | Puno |
| 2001/0010021 A1 | 7/2001 | Boyd et al. |
| 2001/0016741 A1 | 8/2001 | Burkus et al. |
| 2001/0047207 A1 | 11/2001 | Michelson |
| 2002/0026244 A1 | 2/2002 | Trieu |
| 2003/0032962 A1 | 2/2003 | McGahan et al. |
| 2003/0147006 A1 | 8/2003 | Graef et al. |
| 2003/0149438 A1 | 8/2003 | Nichols et al. |
| 2003/0158553 A1 | 8/2003 | Michelson |
| 2003/0195517 A1 | 10/2003 | Michelson |
| 2003/0216740 A1 | 11/2003 | Michelson |
| 2004/0093083 A1 | 5/2004 | Branch et al. |
| 2004/0186574 A1 | 9/2004 | Varga et al. |
| 2004/0220567 A1 | 11/2004 | Eisermann et al. |
| 2004/0220572 A1 | 11/2004 | Michelson |
| 2004/0225361 A1 | 11/2004 | Glenn et al. |
| 2004/0230309 A1 | 11/2004 | DiMauro et al. |
| 2004/0249388 A1 | 12/2004 | Michelson |
| 2005/0010294 A1 | 1/2005 | Michelson |
| 2005/0015149 A1 | 1/2005 | Michelson |
| 2005/0033433 A1 | 2/2005 | Michelson |
| 2005/0038511 A1 | 2/2005 | Martz et al. |
| 2005/0055026 A1 | 3/2005 | Biedermann et al. |
| 2005/0059971 A1 | 3/2005 | Michelson |
| 2005/0096745 A1 | 5/2005 | Andre et al. |
| 2005/0119747 A1 | 6/2005 | Fabris Monterumici et al. |
| 2005/0131541 A1 | 6/2005 | Trieu |
| 2005/0165489 A1 | 7/2005 | Michelson |
| 2005/0171549 A1 | 8/2005 | Boehm et al. |
| 2005/0171606 A1 | 8/2005 | Michelson |
| 2005/0171607 A1 | 8/2005 | Michelson |
| 2005/0187552 A1 | 8/2005 | Michelson |
| 2005/0187554 A1 | 8/2005 | Michelson |

(56) References Cited

U.S. PATENT DOCUMENTS

| | | |
|---|---|---|
| 2005/0222684 A1 | 10/2005 | Ferree |
| 2005/0251146 A1 | 11/2005 | Martz et al. |
| 2005/0267578 A1 | 12/2005 | Michelson |
| 2006/0036247 A1 | 2/2006 | Michelson |
| 2006/0041258 A1 | 2/2006 | Galea |
| 2006/0085001 A1 | 4/2006 | Michelson |
| 2006/0129244 A1 | 6/2006 | Ensign |
| 2006/0142858 A1 | 6/2006 | Colleran et al. |
| 2006/0184172 A1 | 8/2006 | Michelson |
| 2006/0189999 A1 | 8/2006 | Zwirkoski |
| 2006/0212119 A1 | 9/2006 | Varga et al. |
| 2006/0229727 A1 | 10/2006 | Foley |
| 2006/0241758 A1 | 10/2006 | Peterman et al. |
| 2006/0241759 A1 | 10/2006 | Trieu |
| 2006/0241761 A1 | 10/2006 | Gately |
| 2006/0247781 A1 | 11/2006 | Francis |
| 2006/0265077 A1 | 11/2006 | Zwirkoski |
| 2007/0010886 A1 | 1/2007 | Banick et al. |
| 2007/0010889 A1 | 1/2007 | Francis |
| 2007/0032872 A1 | 2/2007 | Simonton et al. |
| 2007/0055274 A1 | 3/2007 | Appenzeller et al. |
| 2007/0067035 A1 | 3/2007 | Falahee |
| 2007/0073398 A1 | 3/2007 | Fabian et al. |
| 2007/0088436 A1 | 4/2007 | Parsons et al. |
| 2007/0093897 A1 | 4/2007 | Gerbec et al. |
| 2007/0093898 A1 | 4/2007 | Schwab et al. |
| 2007/0118222 A1 | 5/2007 | Lang |
| 2007/0118224 A1 | 5/2007 | Shah et al. |
| 2007/0123985 A1 | 5/2007 | Errico et al. |
| 2007/0123986 A1 | 5/2007 | Schaller |
| 2007/0142843 A1 | 6/2007 | Dye |
| 2007/0162041 A1 | 7/2007 | Robie et al. |
| 2007/0191861 A1 | 8/2007 | Allard et al. |
| 2007/0208423 A1 | 9/2007 | Messerli et al. |
| 2007/0208426 A1 | 9/2007 | Trieu |
| 2007/0213737 A1 | 9/2007 | Schermerhorn et al. |
| 2007/0213739 A1 | 9/2007 | Michelson |
| 2007/0213826 A1 | 9/2007 | Smith et al. |
| 2007/0225808 A1 | 9/2007 | Warnick |
| 2007/0233245 A1 | 10/2007 | Trieu |
| 2007/0255413 A1 | 11/2007 | Edie et al. |
| 2007/0260314 A1 | 11/2007 | Biyani |
| 2007/0270862 A1 | 11/2007 | Yu et al. |
| 2007/0276406 A1 | 11/2007 | Mahoney et al. |
| 2007/0282441 A1 | 12/2007 | Stream et al. |
| 2007/0282449 A1 | 12/2007 | de Villiers et al. |
| 2008/0009880 A1 | 1/2008 | Warnick et al. |
| 2008/0027544 A1 | 1/2008 | Melkent |
| 2008/0045966 A1 | 2/2008 | Buttermann et al. |
| 2008/0058821 A1 | 3/2008 | Maurer et al. |
| 2008/0058933 A1 | 3/2008 | Garner et al. |
| 2008/0065082 A1 | 3/2008 | Chang |
| 2008/0077146 A1 | 3/2008 | Pernsteiner et al. |
| 2008/0077241 A1 | 3/2008 | Nguyen |
| 2008/0091211 A1 | 4/2008 | Gately |
| 2008/0097435 A1 | 4/2008 | DeRidder et al. |
| 2008/0097454 A1 | 4/2008 | DeRidder et al. |
| 2008/0103596 A1 | 5/2008 | Shikinami et al. |
| 2008/0119935 A1 | 5/2008 | Alvarez |
| 2008/0125865 A1 | 5/2008 | Abdelgany |
| 2008/0132901 A1 | 6/2008 | Recoules-Arche et al. |
| 2008/0133012 A1 | 6/2008 | McGuckin |
| 2008/0140085 A1 | 6/2008 | Gately et al. |
| 2008/0161810 A1 | 7/2008 | Melkent |
| 2008/0177270 A1 | 7/2008 | Sorrenti et al. |
| 2008/0208255 A1 | 8/2008 | Siegal |
| 2008/0208344 A1 | 8/2008 | Kilpela et al. |
| 2008/0221687 A1 | 9/2008 | Viker |
| 2008/0221694 A1 | 9/2008 | Warnick et al. |
| 2008/0234678 A1 | 9/2008 | Gutierrez et al. |
| 2008/0234687 A1 | 9/2008 | Schaller et al. |
| 2008/0234827 A1 | 9/2008 | Schaller et al. |
| 2008/0243255 A1 | 10/2008 | Butler et al. |
| 2008/0249628 A1 | 10/2008 | Altarac et al. |
| 2008/0255564 A1 | 10/2008 | Michelson |
| 2008/0262555 A1 | 10/2008 | Assell et al. |
| 2008/0269756 A1 | 10/2008 | Tomko et al. |
| 2008/0287955 A1 | 11/2008 | Michelson |
| 2008/0300601 A1 | 12/2008 | Fabian et al. |
| 2008/0306488 A1 | 12/2008 | Altarac et al. |
| 2008/0306489 A1 | 12/2008 | Altarac et al. |
| 2008/0312743 A1 * | 12/2008 | Vila ............. A61F 2/442 623/17.16 |
| 2009/0024134 A1 | 1/2009 | Triplett et al. |
| 2009/0024135 A1 | 1/2009 | Triplett et al. |
| 2009/0030423 A1 | 1/2009 | Puno |
| 2009/0030458 A1 | 1/2009 | Malberg et al. |
| 2009/0048676 A1 | 2/2009 | Fabian, Jr. |
| 2009/0054991 A1 | 2/2009 | Biyani et al. |
| 2009/0062833 A1 | 3/2009 | Song |
| 2009/0088847 A1 | 4/2009 | Krishna et al. |
| 2009/0105832 A1 | 4/2009 | Allain et al. |
| 2009/0112217 A1 | 4/2009 | Hester |
| 2009/0143809 A1 | 6/2009 | Assell et al. |
| 2009/0143859 A1 | 6/2009 | McClellan, III et al. |
| 2009/0149960 A1 | 6/2009 | Hushka et al. |
| 2009/0157125 A1 | 6/2009 | Hoffman et al. |
| 2009/0157186 A1 | 6/2009 | Magerl |
| 2009/0177195 A1 | 7/2009 | Rawles et al. |
| 2009/0177205 A1 | 7/2009 | McCormack et al. |
| 2009/0177285 A1 | 7/2009 | Frey et al. |
| 2009/0182431 A1 | 7/2009 | Butler et al. |
| 2009/0198246 A1 | 8/2009 | Lim |
| 2009/0216239 A1 | 8/2009 | Johansson et al. |
| 2009/0216241 A1 | 8/2009 | Dinville |
| 2010/0023013 A1 | 1/2010 | Flickinger et al. |
| 2010/0152790 A1 | 6/2010 | Hestad |
| 2010/0217394 A1 | 8/2010 | Michelson |
| 2010/0305702 A1 | 12/2010 | Michelson |
| 2011/0009966 A1 | 1/2011 | Michelson |
| 2013/0110239 A1 | 5/2013 | Siegal et al. |

FOREIGN PATENT DOCUMENTS

| | | |
|---|---|---|
| EP | 1093760 A2 | 4/2001 |
| EP | 1369357 A1 | 12/2003 |
| EP | 1419741 A2 | 5/2004 |
| EP | 1442732 A1 | 8/2004 |
| EP | 1500372 A1 | 1/2005 |
| EP | 1504735 A2 | 2/2005 |
| EP | 1525853 A2 | 4/2005 |
| EP | 1525863 A2 | 4/2005 |
| EP | 1709920 A2 | 10/2006 |
| EP | 1847229 A2 | 10/2007 |
| FR | 2729557 A1 | 7/1996 |
| FR | 2900814 A1 | 11/2007 |
| WO | 9001298 A1 | 2/1990 |
| WO | 9002524 A1 | 3/1990 |
| WO | 9526164 A1 | 10/1995 |
| WO | 9614799 A1 | 5/1996 |
| WO | 9963891 A1 | 12/1999 |
| WO | 0042898 A2 | 7/2000 |
| WO | 0066011 A1 | 11/2000 |
| WO | 0066045 A1 | 11/2000 |
| WO | 0156497 A2 | 8/2001 |
| WO | 0180784 A1 | 11/2001 |
| WO | 02078514 A2 | 10/2002 |
| WO | 02098276 A2 | 12/2002 |
| WO | 2005011539 A2 | 2/2005 |
| WO | 2005077288 A1 | 8/2005 |
| WO | 2006072941 A2 | 7/2006 |
| WO | 2007124352 A2 | 11/2007 |
| WO | 2008016598 A2 | 2/2008 |
| WO | 2008036505 A2 | 3/2008 |
| WO | 2008058070 A2 | 5/2008 |
| WO | 2011006077 A1 | 1/2011 |
| WO | 2011006081 A1 | 1/2011 |
| WO | 0156513 A1 | 8/2011 |

* cited by examiner

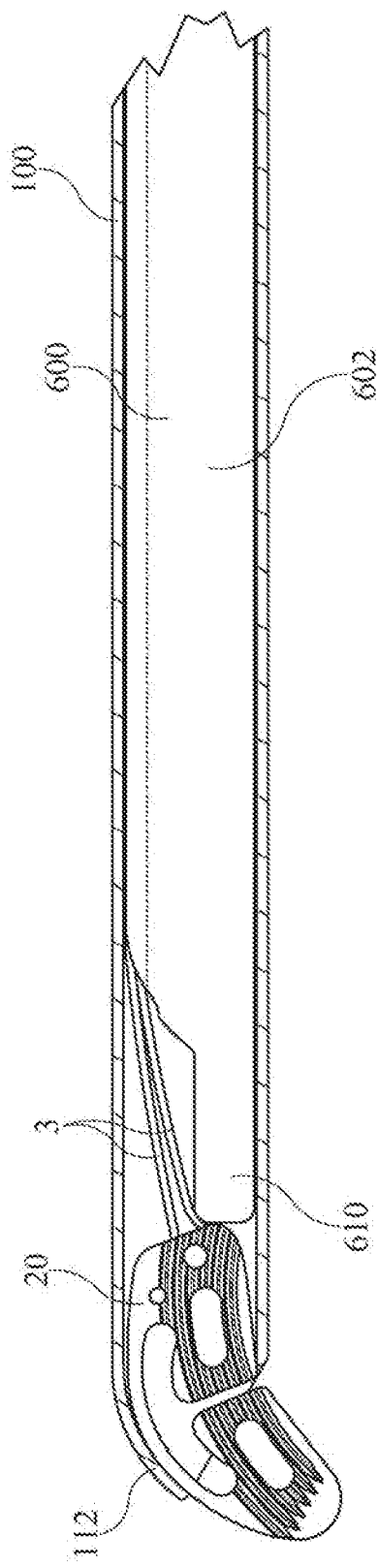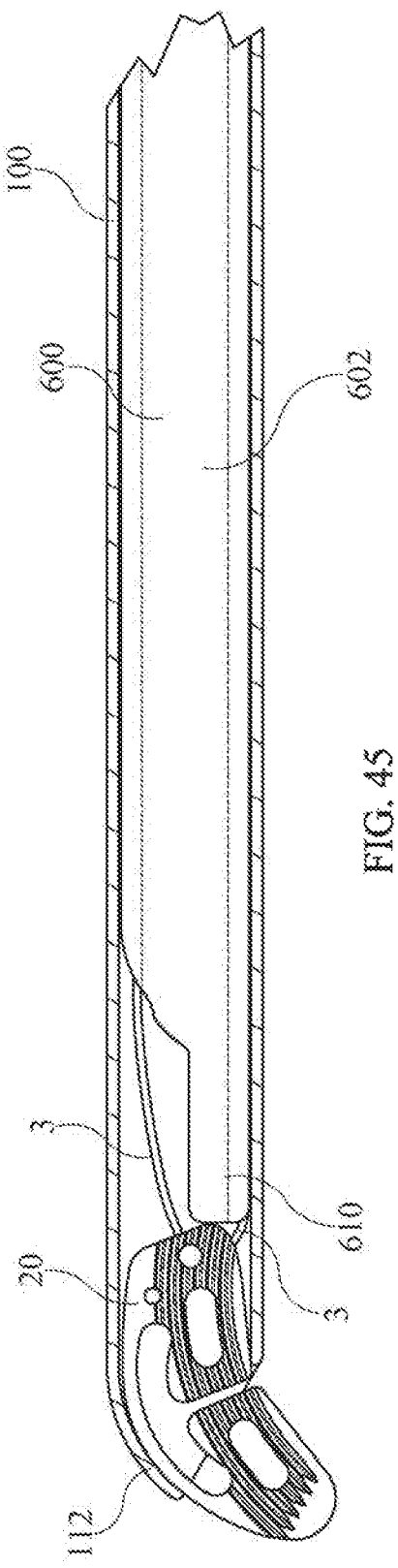

INTER-BODY IMPLANTATION SYSTEM AND METHOD

CROSS-REFERENCE TO RELATED APPLICATIONS

This application is a continuation of U.S. patent application Ser. No. 12/833,342, filed Jul. 9, 2010, now U.S. Pat. No. 9,814,599, which claims the benefit of U.S. Provisional Patent Application Ser. No. 61/224,333, filed Jul. 9, 2009, the entire contents of each of which are incorporated by reference herein.

TECHNICAL FIELD

The present invention relates generally to an inter-body device for intervertebral disc replacement or inter-body spinal fusion and more specifically to a system including a device for disc replacement or an inter-body device for spinal fusion and an insertion system and method for placing the aforementioned devices in an intervertebral space utilizing a plurality of surgical approaches.

BACKGROUND

The normal human spine is comprised of seven cervical, twelve thoracic, and five lumbar vertebrae. Intervertebral discs are interposed between adjacent vertebrae with the exception of the first two cervical vertebrae. The spinal vertebrae are supported by ligaments, tendons and muscles which allow movement such as flexion, extension, lateral bending and rotation.

Motion between vertebrae occurs through the relative motion of the disc and two facet joints. The disc lies in the front or anterior portion of the spine. The facet joints lie laterally on either side of the posterior portion of the spine. The basic shape of a human intervertebral disc is oval, having a depression in a longitudinal side thereof to form a kidney bean shape.

The spine is a flexible structure that is capable of great curvature and twist in a plurality of directions. However, developmental or genetic irregularities, trauma, chronic stress and degeneration due to wear may result in the need for surgical intervention to effect repair. In cases of degeneration (or injury and disease) it may be necessary or desirable to remove a disc that is no longer performing the function of separation between adjacent vertebrae. This is particularly desirable in cases of degeneration or herniation, which often result in chronic and debilitating back pain.

A damaged disc may be replaced with a prosthetic disc that is intended to be functionally identical to the natural disc. Some prior art replacement discs are shaped to approximate the shape of the natural disc that is being replaced, and further are comprised of a flexible material having a shape memory such that the disc may be deformed for insertion through a small area in the spine, then expand to its normal shape once insertion is completed. One of the major difficulties with many prior art discs is that they are most easily inserted utilizing an anterior surgical insertion due to the structure of the spine and arrangement of nerves proximate the spine. The anterior surgical approach to disc replacement is, however, quite invasive.

Furthermore, many prior art disc replacements are complex devices made of a combination of materials and are also bulky and difficult to place properly between adjacent vertebrae. The implantation of these prior art devices requires invasive surgery for proper placement. Additionally, some disc replacements utilize materials such as hydrogels to simulate the gelatinous texture of the natural disc nucleus. However, these materials tend to be easily damaged during implantation and also tend to migrate into undesired areas of the body.

A number of prior art inter-body devices to effect the fusion of adjacent vertebrae to each other are also employed to alleviate the pain and discomfort caused by disc degeneration. Implantation of these prior art devices is typically quite unwieldy and invasive due primarily to their complex structure and the complex geometry of the human spine.

Accordingly, a need exists for an inter-body disc device or a disc replacement device and an implantation system for inserting the inter-body fusion or disc replacement device that are robust and surgically minimally invasive for the efficacious replacement of damaged or degenerated intervertebral discs.

SUMMARY

The present invention obviates the aforementioned difficulties in the prior art by providing an improved inter-body device that more closely resembles natural disc physiology and by providing a system and method for deploying improved inter-body devices that enables a surgeon to accurately and quickly place an inter-body device of appropriate size in a disc space, thereby minimizing surgery times and greatly enhancing recovery times for disc replacement surgeries.

The improved inter-body devices of the present invention comprise a plurality of cans, or generally annular bodies, that extend from a flexible bridge that permits the cans to flex independently and compress together for ease of deployment in said disc space, while relaxing to their natural shape once deployed. The cans may further include a plurality of apertures for accepting bone graft material to aid in the fusion process, as well as corrugated upper and lower surfaces that act to guide the inter-body devices upon entry into the disc space and engage the adjacent vertebrae.

The inter-body insertion system of the present invention includes an inserter tube that is shaped to guide a plurality of instruments into the disc space in the same orientation throughout the process. Once inserted, the inserter tube may be secured to the spine by means of an extension arm that locks the tube in place. A plurality of bullnose instruments having distal tips of varying shapes are used to prepare the disc space for entry of the inter-body device as well as to aid in inserting the inter-body device into the disc space.

Additionally, the system of the present invention includes a plurality of articulating trial implants that may be inserted to determine the proper implant length prior to deployment of an inter-body device. The trial implants of the invention may articulate with respect to an implant rod that aids in positioning them in the disc space, thereby providing for relatively easy trial implant insertion and removal.

The invention further comprises a novel inserter tube handle that is capable of being secured to a complementary handle that attaches to a plurality of bullnose instruments for insertion into the disc space. A box cutter having a distal tip with opposed cutting edges is provided to shave the posterior endplates of adjacent vertebrae in preparation for implant insertion.

The invention also includes a bone graft insertion system that utilizes a novel bone graft plunger for distributing morselized bone graft material throughout the anterior disc space.

Other features, advantages, and objects of the present invention will become apparent from the detailed description of the invention herein below, taken in conjunction with the appended drawing Figures.

BRIEF DESCRIPTION OF THE DRAWING FIGURES

FIG. 44 is a partial side view of an inter-body device and bullnose inside an inserter tube in accordance with one embodiment of the present invention;

FIG. 45 is a partial side view of an inter-body device and bullnose inside an inserter tube in accordance with one embodiment of the present invention;

DETAILED DESCRIPTION

Figure 1:
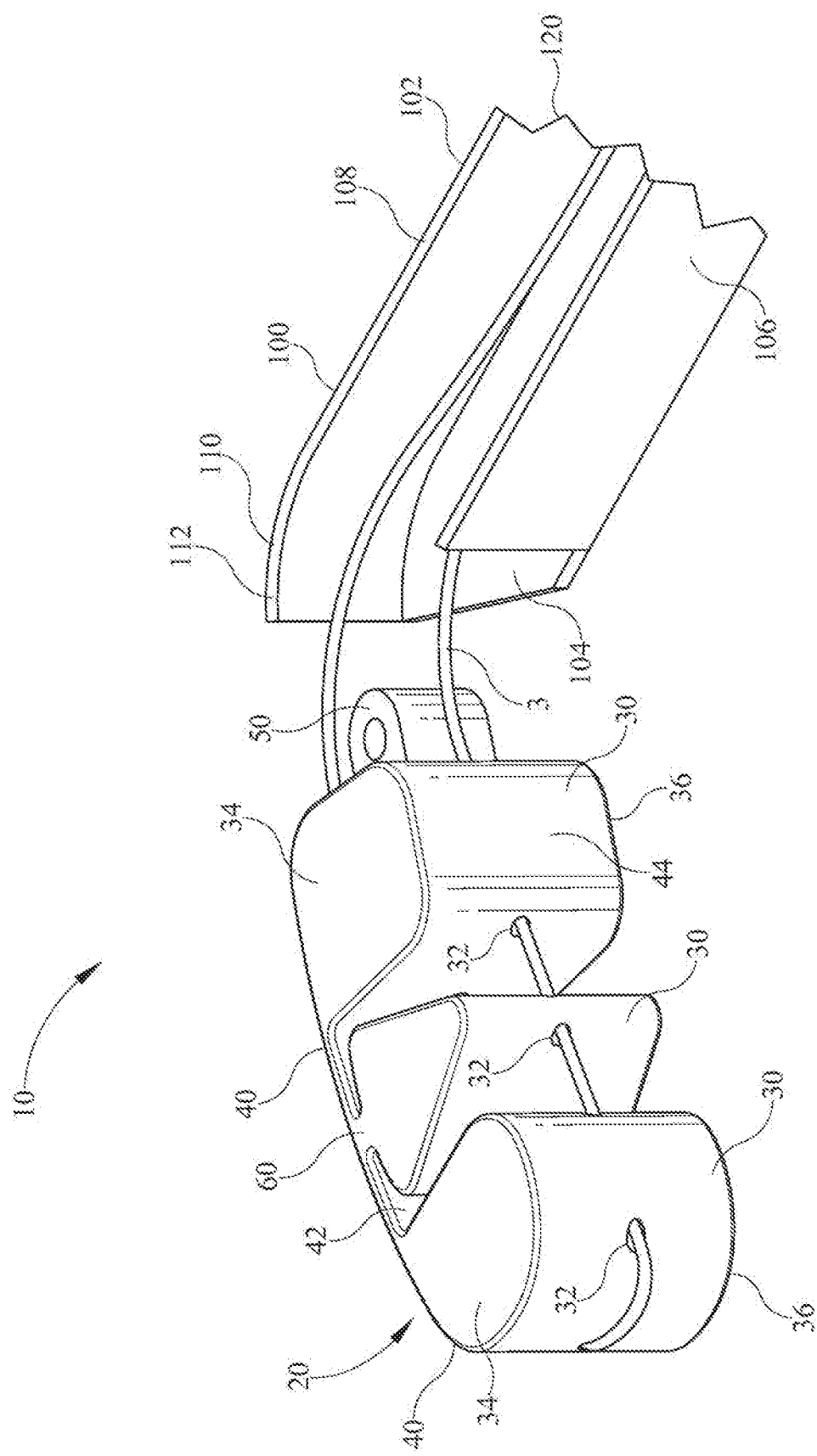
FIG. 1 is a perspective view of a an inter-body device and an inserter tube in accordance with one embodiment of the present invention.
Figure 2:
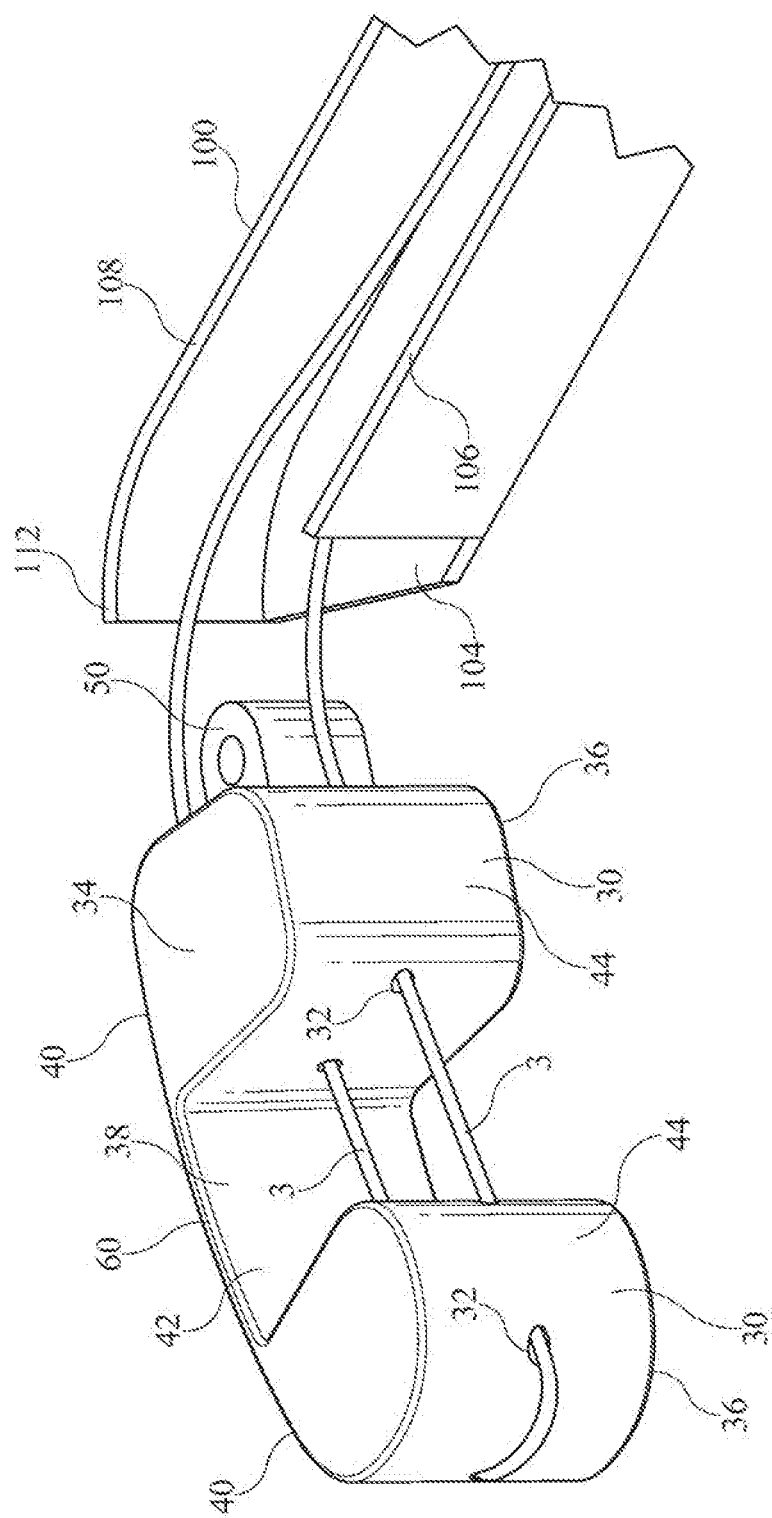
FIG. 2 is a perspective view of a an inter-body device and an inserter tube in accordance with one embodiment of the present invention.
Figure 3:
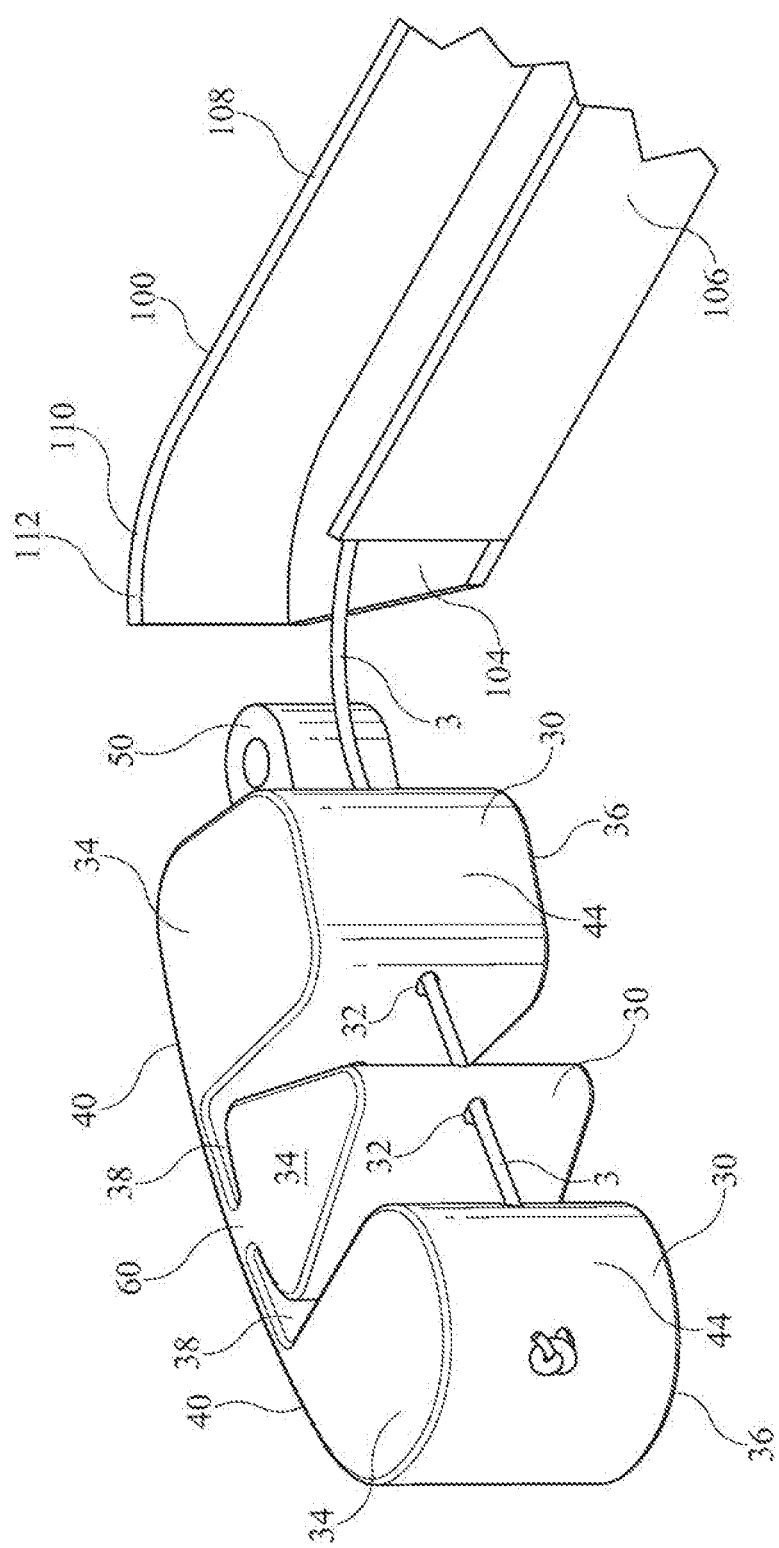
FIG. 3 is a perspective view of a an inter-body device and an inserter tube in accordance with one embodiment of the present invention.
Figure 50:
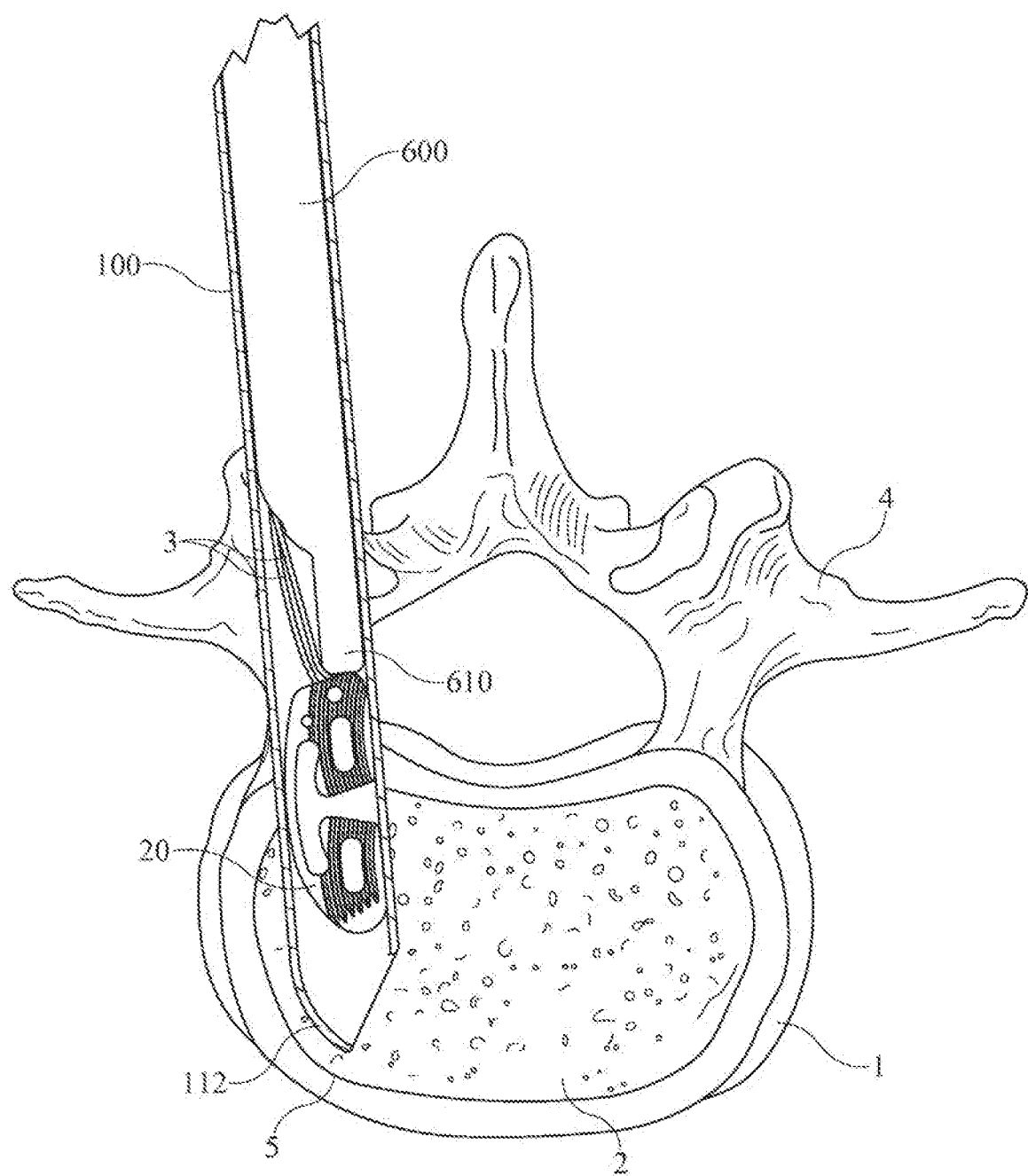
FIG. 50 is a top view of an inserter tube in a disc space, with an inter-body device and bullnose advancing into said disc space in accordance with one embodiment of the present invention.
Figure 55:
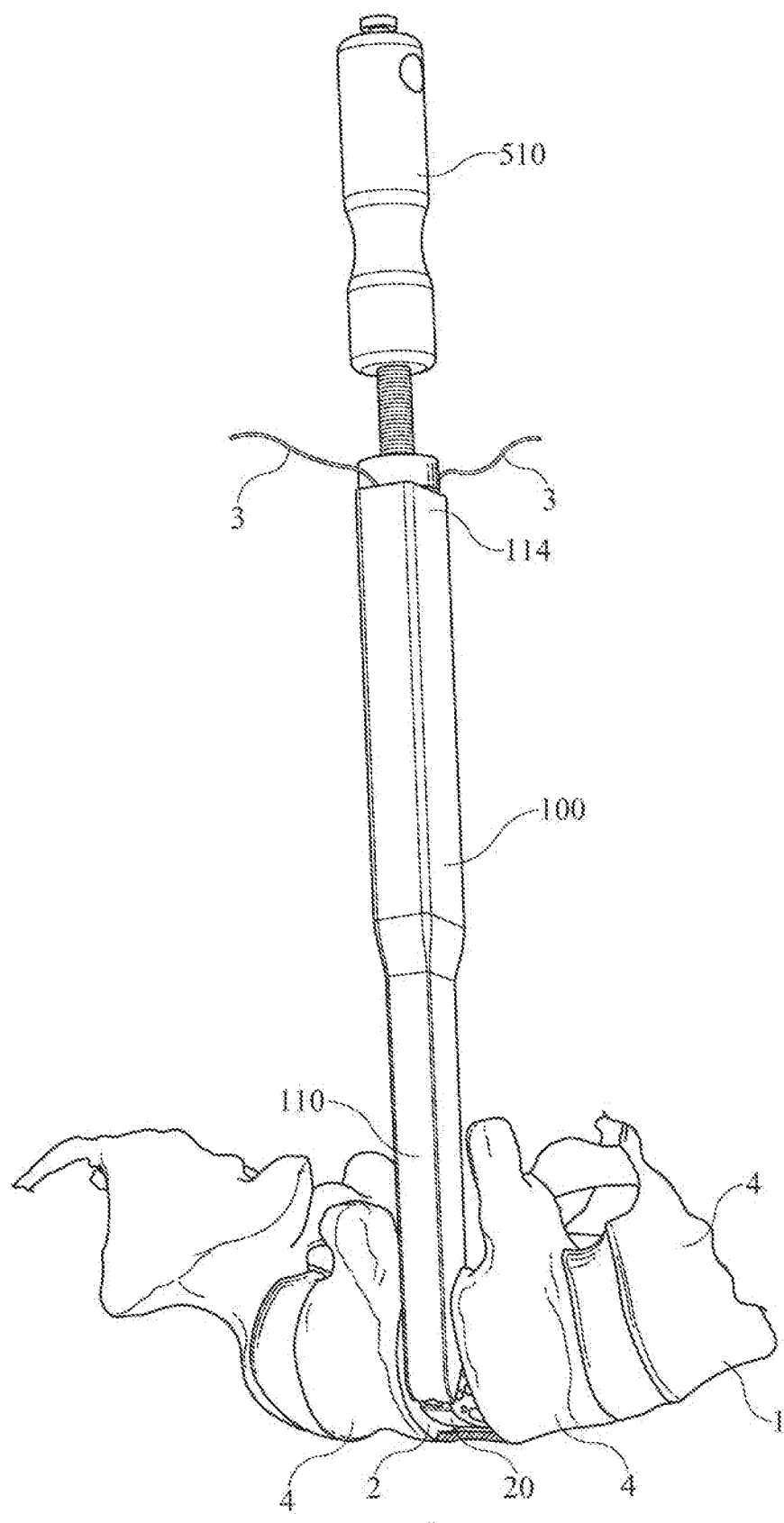
FIG. 55 is a side view of an inserter tube advanced into a disc space in accordance with one embodiment of the present invention.

Referring now to the drawing Figures, and in particular FIGS. 1-3, and in accordance with a preferred constructed embodiment of the system 10 of the present invention, there is depicted an inter-body device 20 and an inserter tube 100 for orienting and inserting said inter-body device 20 into a disc space of a human spine. Drawing FIGS. 50 and 55 depict one example of the insertion of inter-body device 20 into a disc space 2 of a spine 1 between vertebrae 4, and may be referred to throughout this specification for reference to the human anatomy to which the present invention is applied. Furthermore, it should be noted that the disc to be replaced by the inter-body device 20 of the present invention is first removed by a surgeon performing a thorough discectomy. Typically, it is desirable to extend the discectomy to a contralateral half of the disc space to allow placement of the longest inter-body device 20 possible and to maximize bony surface exposure for fusion to occur. If there is significant disc space 2 collapse, a complete discectomy may not be possible until disc space 2 distraction is performed utilizing one of many known in the art distraction tools.

As seen in FIG. 1, inter-body device 20 may comprise a plurality of lobes or cans 30, each spaced one from another and depending from a flexible bridge 60 that permits independent flexure and motion of each can 30 to facilitate entry into disc space 2. Flexible bridge 60 may be comprised of a memory metal such as nitinol or other flexible plastic material that has shape memory so that the overall shape of inter-body device 20 is retained once device 20 is implanted. In the embodiments of the invention depicted in FIGS. 1-3 each can 30 includes a pair of generally parallel passageways 32 therein, through which a suture 3 may be threaded to aid in positioning of inter-body device 20, as well as to enable retrieval device 20 should its' placement prove unsatisfactory. Once inter-body device 20 is properly inserted into disc space 2, suture 3 may be manipulated to aid in implant positioning by pulling on either end thereof. Once device 20 is properly positioned, suture 3 may simply be pulled through both passageways 32 and thus removed from inter-body device 20.

Inter-body device 20 cans 30 may further comprise an upper surface 34 and a lower surface 36 that contact upper and lower surfaces of adjacent vertebrae 4 once inter-body device 20 is properly positioned in disc space 2. Inter-body device 20 may further comprise an anterior wall 40 that may be integral with bridge 60, and may be generally convex in shape. Anterior wall 40 may terminate in distal and proximal cans 30. Anterior wall 40 includes an interior wall portion 42 that extends between adjacent cans 30. Additionally, each can 30 includes a posterior wall 44 that extends generally between upper 34 and lower 36 portions of cans 30 on a posterior portion thereof.

While many embodiments of the inter-body device 20 of the present invention are shown to have a generally anterior curvature, it should be recognized that inter-body devices 20 having a posterior curvature are within the scope of the present invention. Additionally, inter-body device 20 is preferably formed of a material that is durable and non-reactive. A wide variety of biocompatible materials may be utilized to manufacture the inter-body device 20 of the present invention, including but not limited to biocompatible polymers, elastomeric materials, hydrogels, hydrophilic polymers, shape memory polymers, and shape memory metals. It is understood that one of ordinary skill in the art would be aware of a variety of materials suitable for such implantation. In one embodiment of the invention, inter-body device 20 is comprised of a carbon fiber material while in another, device 20 is comprised of a polyetherketone (PEK) material.

As shown in FIG. 1, proximal can 30 may include a hitch 50, depicted in this embodiment of the invention as a generally annular protrusion extending outwardly from proximal can 30, which may be grasped or secured to various insertion tools as will be discussed in greater detail herein below.

FIGS. 1-3 also depict an inserter tube 100 shown with one wall removed to show the path of suture 3 through inserter tube 100. Inserter tube 100 comprises a pair of opposed upper and lower walls 102, 104 and opposed medial and lateral walls 106, 108 that define a hollow tubular member through which inter-body device 20 may be deployed. Inserter tube 100 includes a distal end 110 wherein lateral wall 108 forms a curved portion 112 that guides the deployment of inter-body device 20 as it is advanced through inserter tube 100. In this embodiment of the present invention lateral wall 108 curved portion 112 has a length greater than that of medial wall 106 to allow inter-body device 20 to curve into disc space 2 as it is advanced through inserter tube 100.

Cans 30 of each inter-body device 20 are spaced such that a relief area 38 is defined by the void space between cans 30. Relief area 38 permits inter-body device 20 and cans 30 to flex and compress during insertion and placement into disc space 2 while returning to its relaxed shape once it is properly positioned. FIG. 2 depicts an inter-body device 20 having only two cans 30, thereby providing for a much larger relief area 38. FIG. 3 depicts an inter-body device 20 wherein suture 3 is knotted at a terminal end for retrieval of device 20 back through inserter tube 100.

Figure 4:
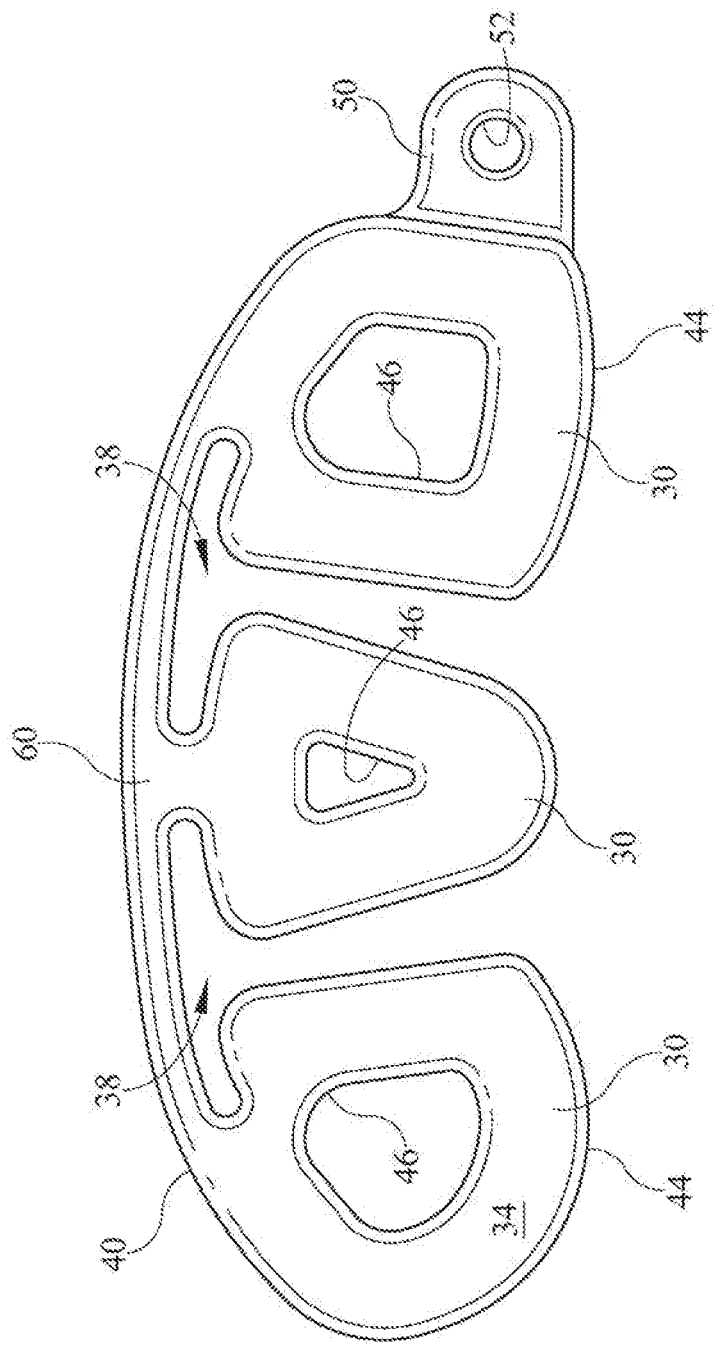
FIG. 4 is a top view of an inter-body device in accordance with one embodiment of the present invention.

FIG. 4 is a top view of an embodiment of the present invention whereby each can 30 of inter-body device 20 includes an aperture 46 therein for accepting a morselized bone graft material to enhance the spinal fusion process. Additionally, as seen in FIG. 4 hitch 50 may comprise a generally annular aperture 52 therein for accepting a pin (not shown) or other instrument for inserting, retrieving and positioning inter-body device 20 in disc space 2.

Figure 5:
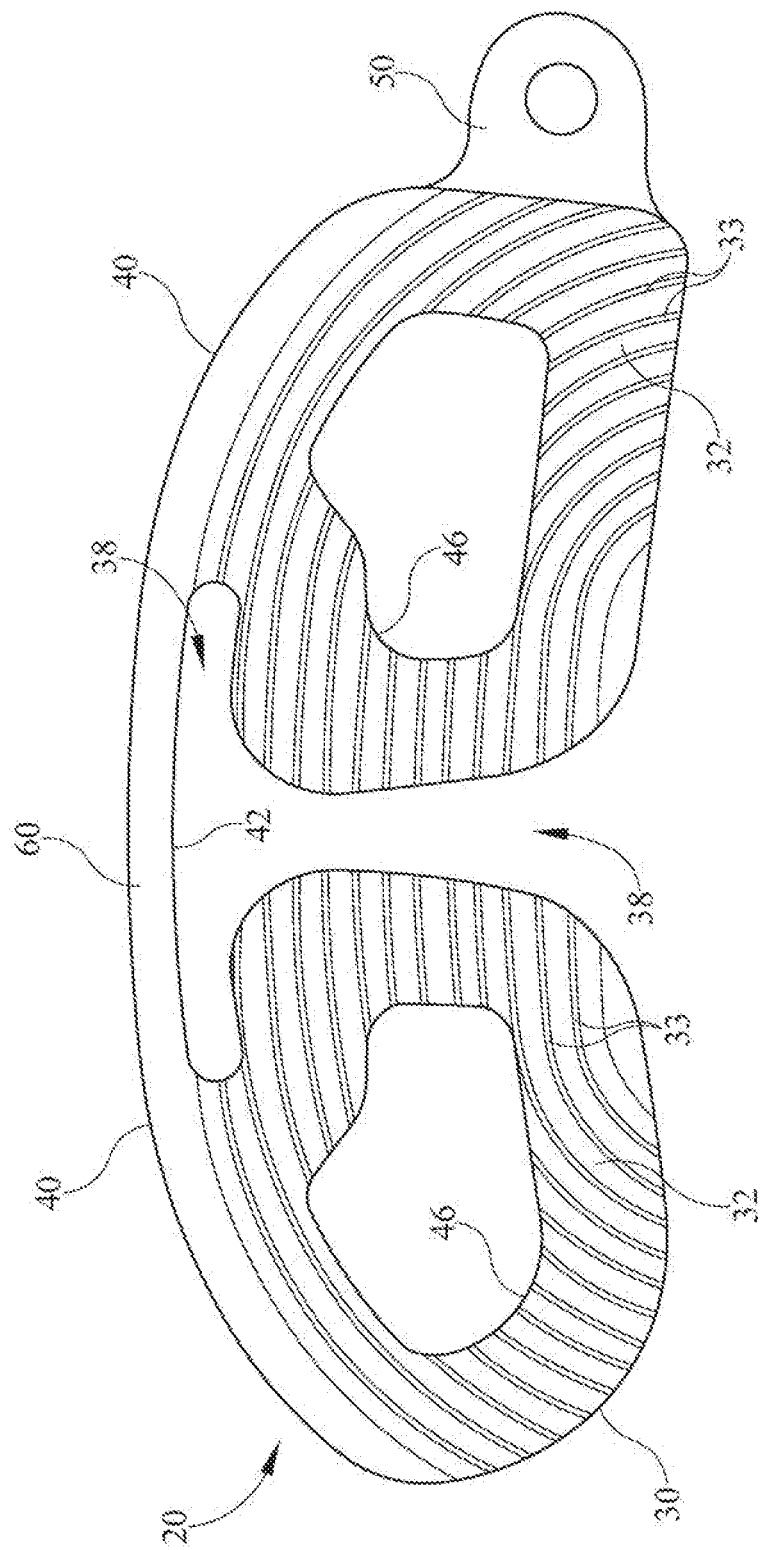
FIG. 5 is a top view of an inter-body device in accordance with one embodiment of the present invention.
Figure 6:
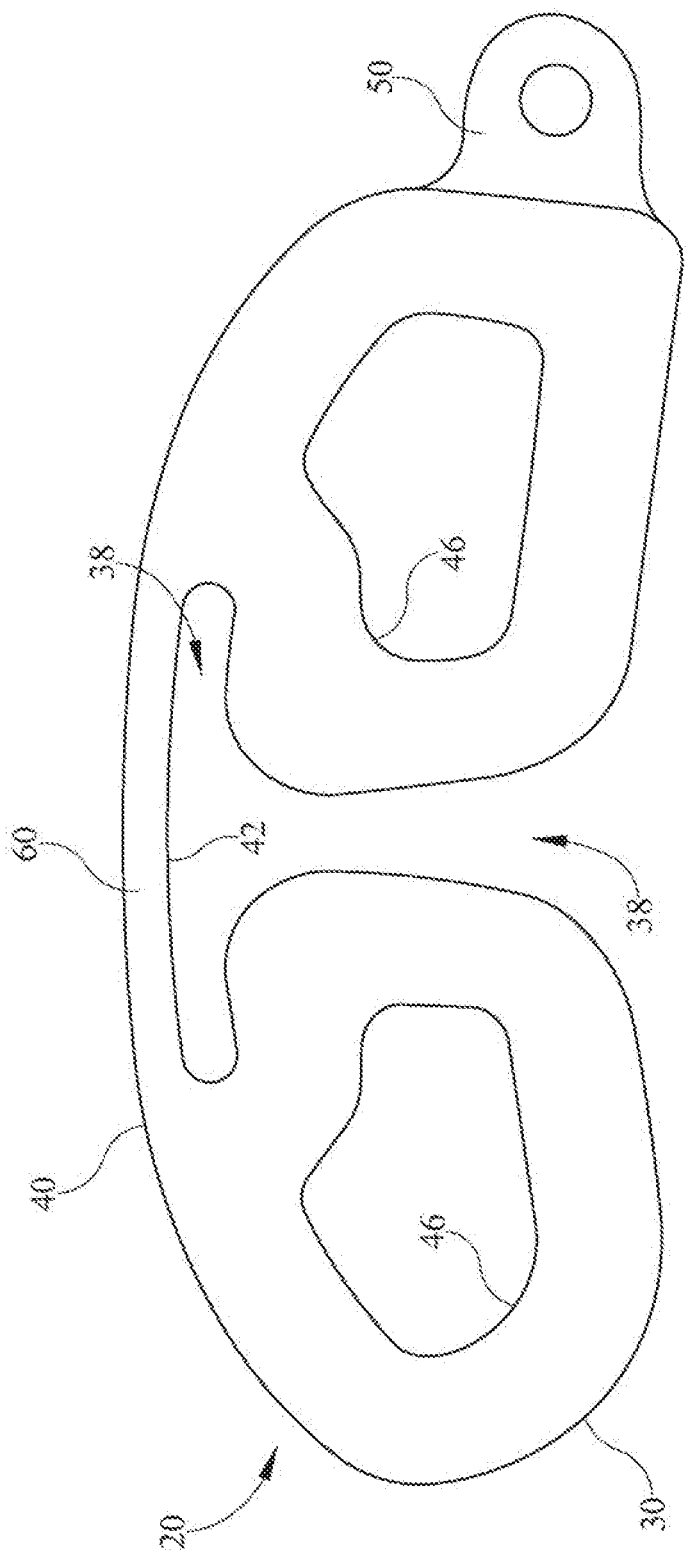
FIG. 6 is a top view of an inter-body device in accordance with one embodiment of the present invention.

FIGS. 5 and 6 depict a further embodiment of the present invention whereby relief portion 38 of inter-body device 20 proximate interior wall 42 defines an elongated slot that enables bridge 60 to flex while each can 30 flexes independently of the other and is capable of motion in three planes. This feature of the invention enables accurate positioning of device 20 in disc space 2 by allowing device 20 to deform during insertion into disc space 2 and expand back to its relaxed shape once properly inserted. The embodiment of the invention shown in FIG. 5 depicts upper surfaces 32 having a plurality of corrugated ridges 33 thereon. Lower surfaces 34 may also include a plurality of corrugated ridges 33 to allow inter-body device 20 to engage the upper and lower surfaces of adjacent vertebrae when inserted in disc space 2, which also assists in device 20 positioning within disc space 2.

Figure 7:
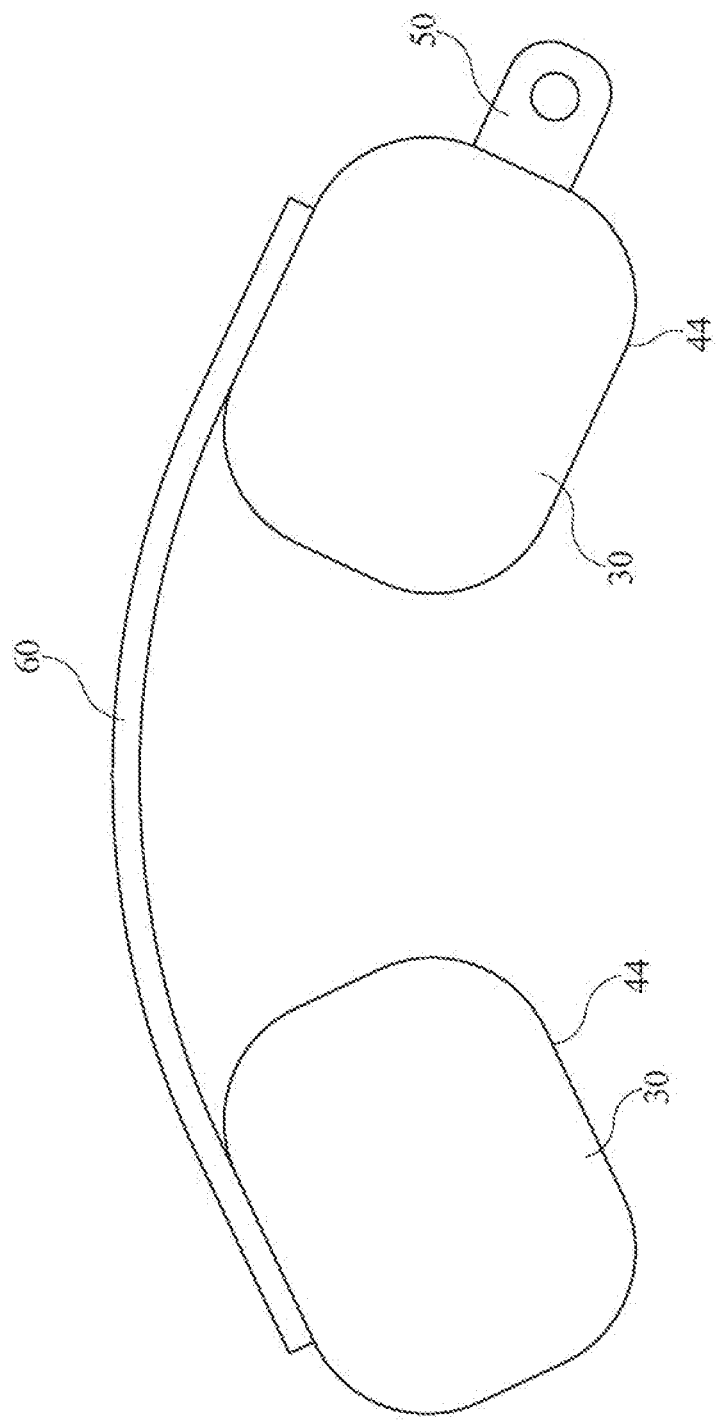
FIG. 7 is a top view of an inter-body device in accordance with one embodiment of the present invention.
Figure 8:
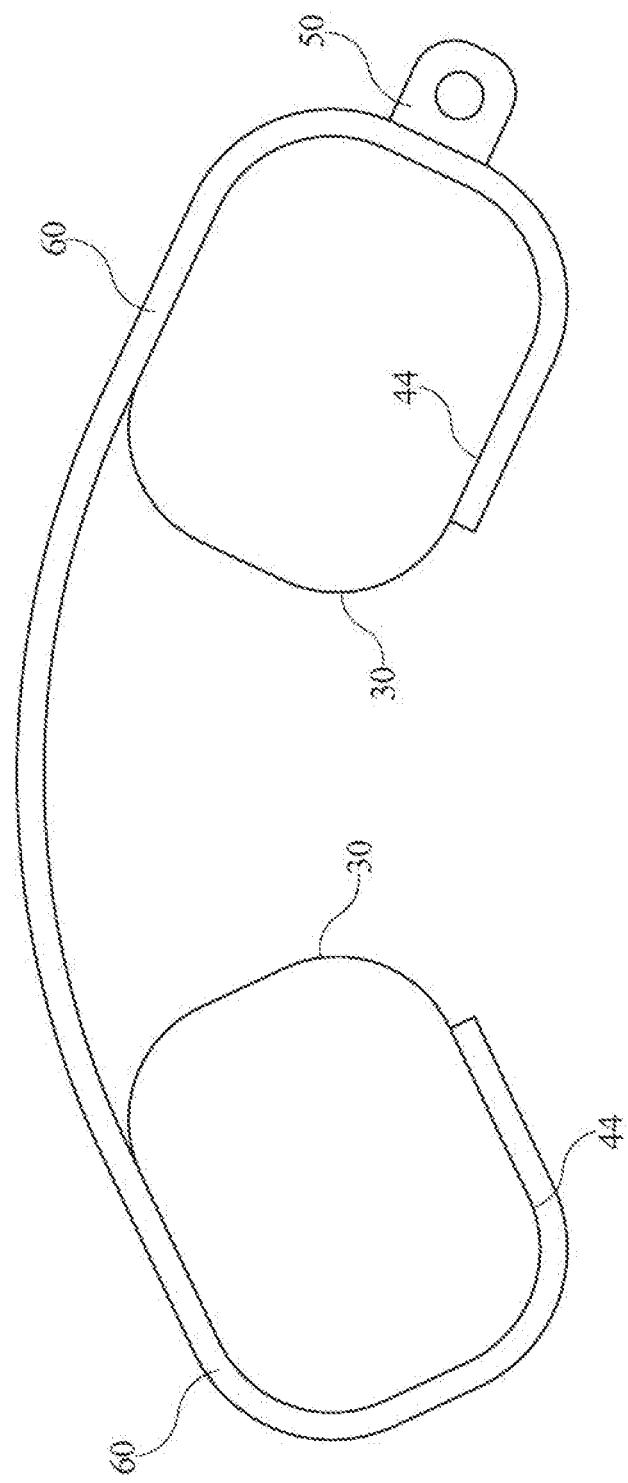
FIG. 8 is a top view of an inter-body device in accordance with one embodiment of the present invention.

FIG. 7 depicts a yet further embodiment of inter-body device 20 whereby flexible bridge 60 is secured to a pair of opposed cans 30, the proximal one of which includes a hitch 50 depending therefrom to facilitate insertion and removal. FIG. 8 depicts a similar embodiment to that of FIG. 7 wherein flexible bridge 60 extends around can 30 posterior wall 44 to firmly secure can 30 to bridge 60 while still permitting independent movement of each can 30.

Figure 9:
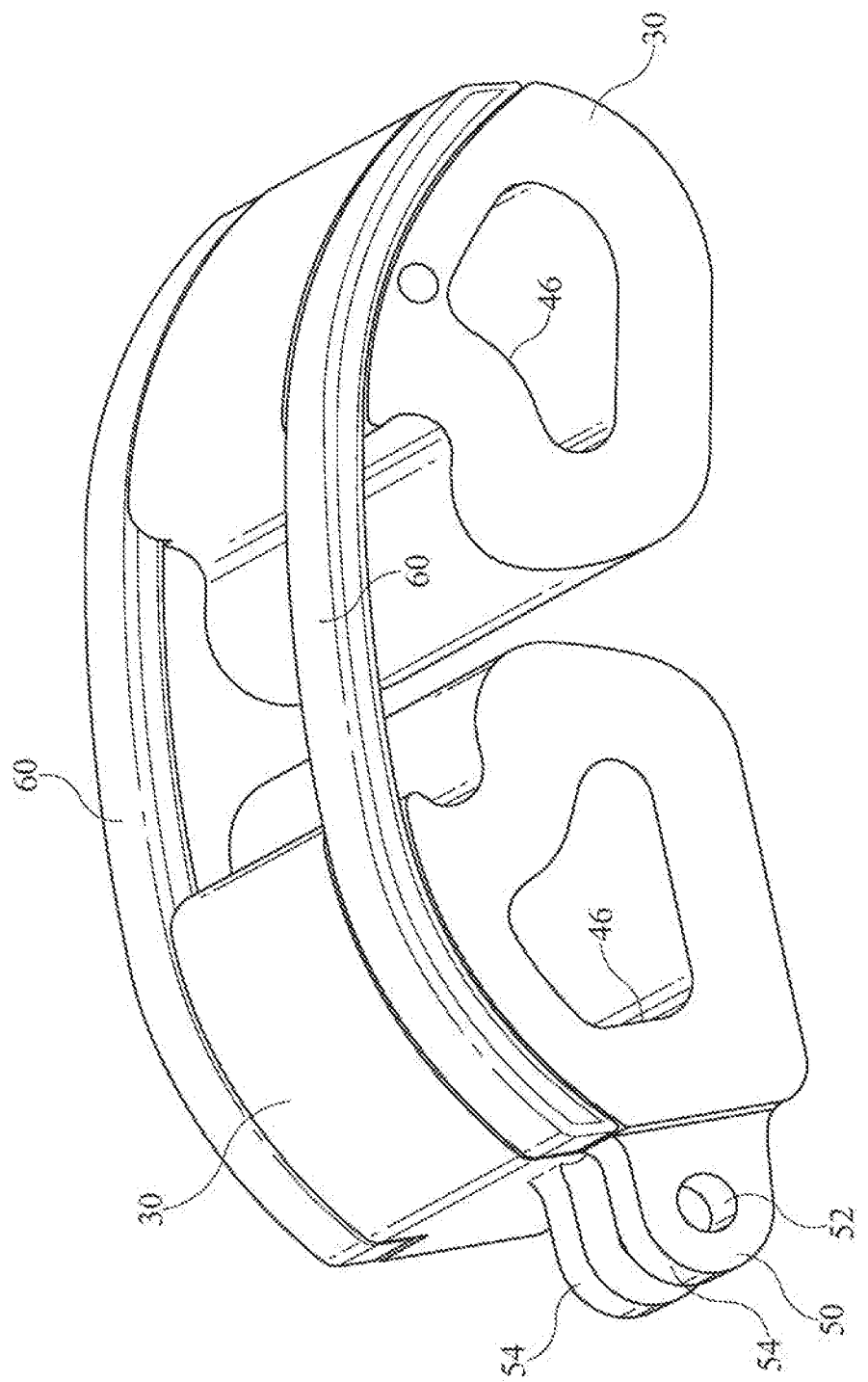
FIG. 9 is a perspective view of an inter-body device in accordance with one embodiment of the present invention.

FIG. 9 shows an additional exemplary embodiment of inter-body device 20 having a pair of spaced opposed flexible bridges 60, each secured to a pair of spaced cans 30 providing a relatively large relief area 38. In this embodiment of the invention, a hitch 50 is provided having a pair of spaced flanges 54 extending from proximal can 30, each with an aperture 52 therein to accept a pin (not shown) for connecting inter-body device 20 to an insertion and removal tool as will be discussed in greater detail herein below.

Referring now to FIGS. 10-14 there are depicted a plurality of articulating inter-body devices 200 in accordance with a yet further embodiment of the present invention. Inter-body device 200 comprises a distal half 210 and a proximal half 220 connected by a central hinge 230. Each half 210, 220 of trial implant 200 includes a passageway 232 into which a segment of flexible spine 240 is inserted. Flexible spine 240 may be comprised of a memory metal to permit halves 210, 200 to flex with respect to each other then return to a relaxed position. A hitch 50 is also provided extending from proximal half 220 of trial implant 200 to facilitate insertion and removal thereof form disc space 2.

Figure 10:
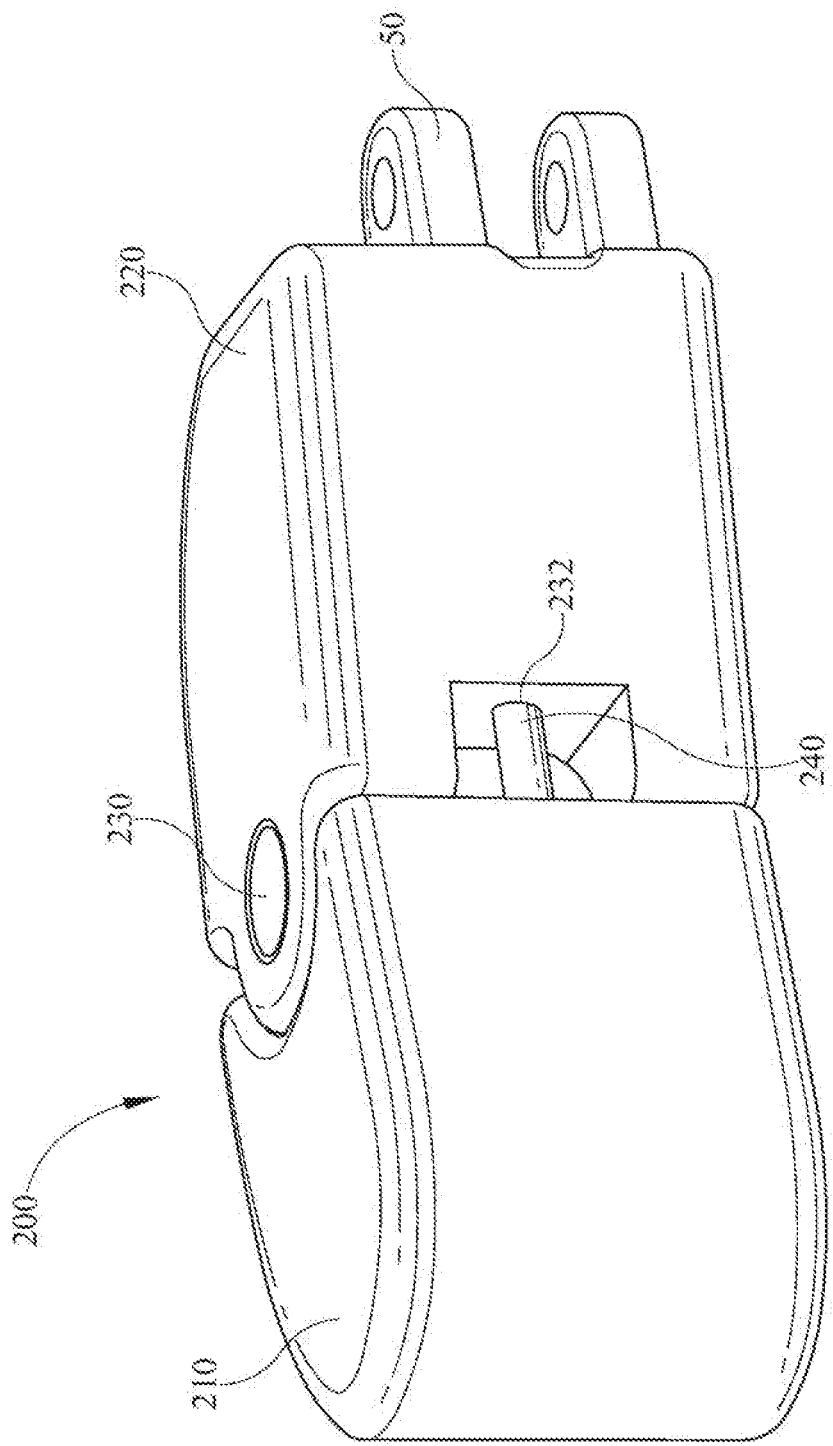
FIG. 10 is a perspective view of an inter-body device in accordance with one embodiment of the present invention.
Figure 11:
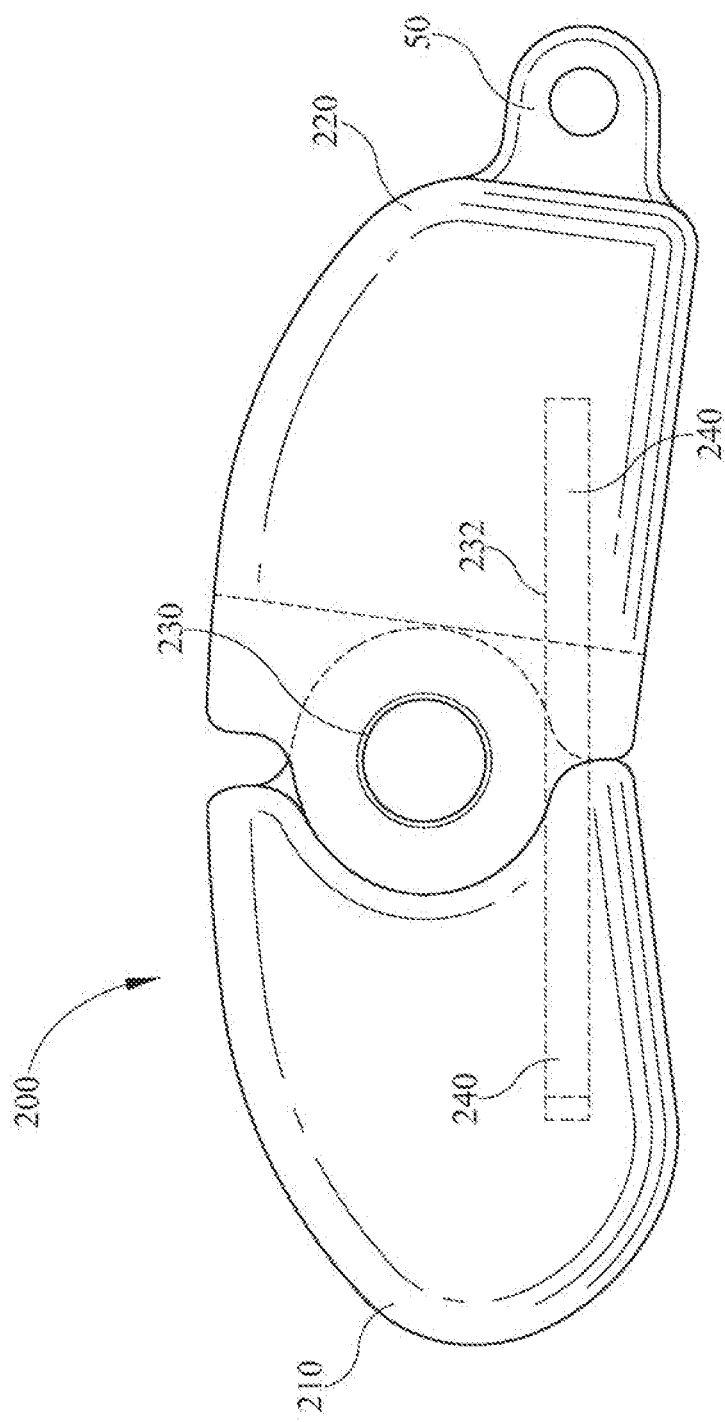
FIG. 11 is a top view of an inter-body device in accordance with one embodiment of the present invention.
Figure 12:
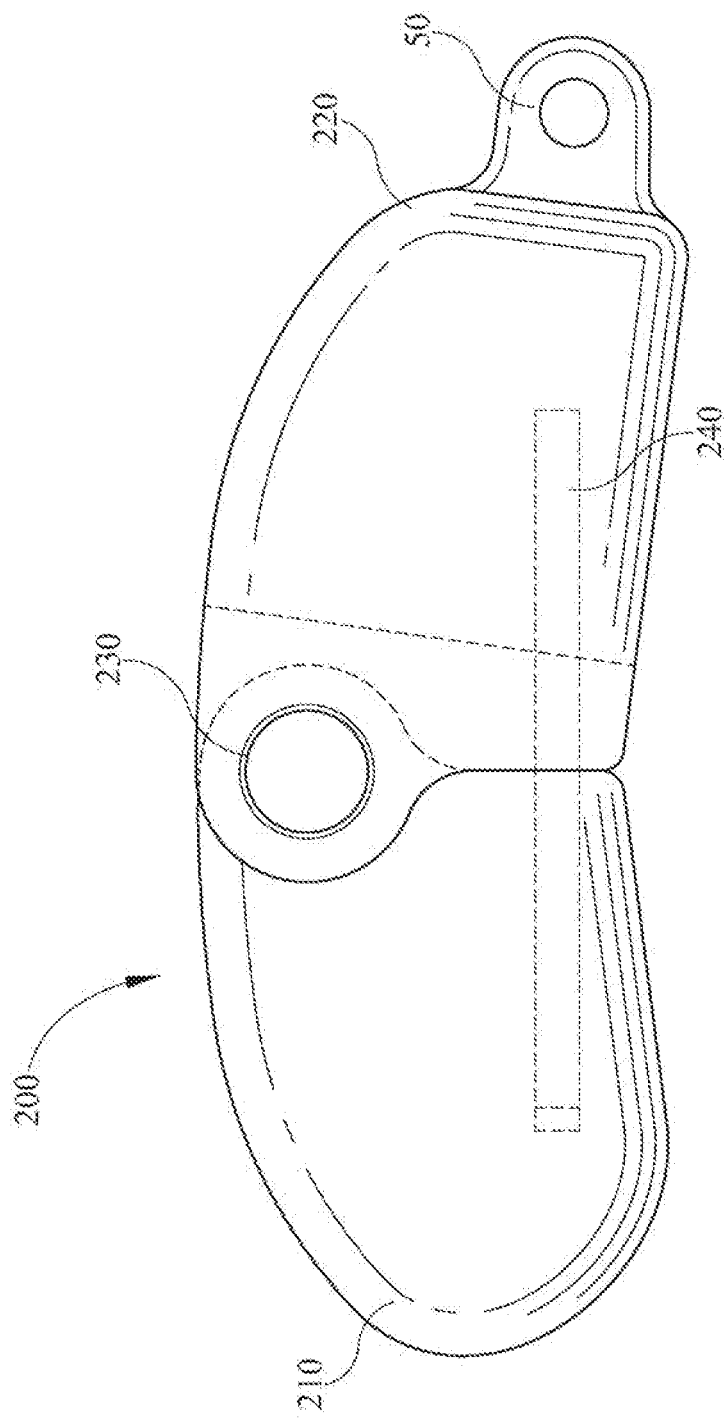
FIG. 12 is a top view of an inter-body device in accordance with one embodiment of the present invention.
Figure 13:
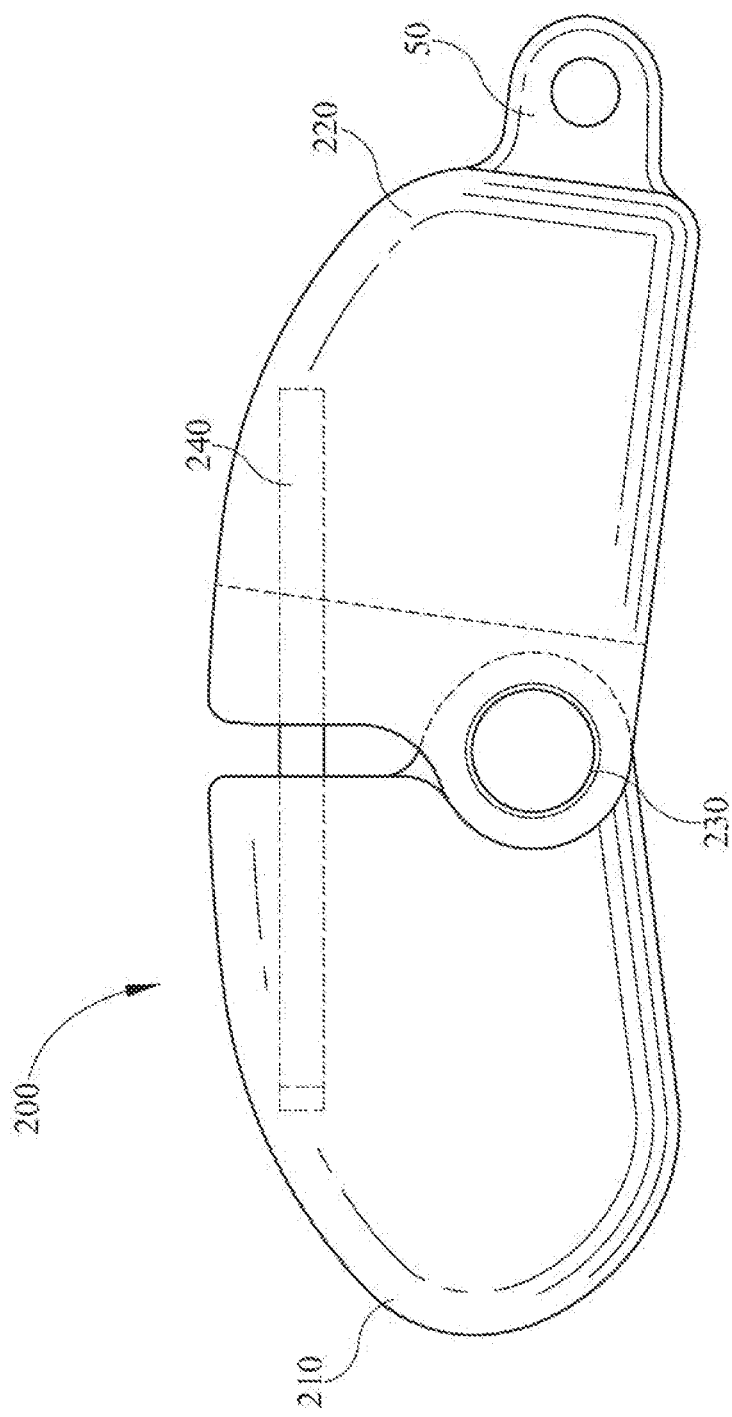
FIG. 13 is a top view of an inter-body device in accordance with one embodiment of the present invention.
Figure 14:
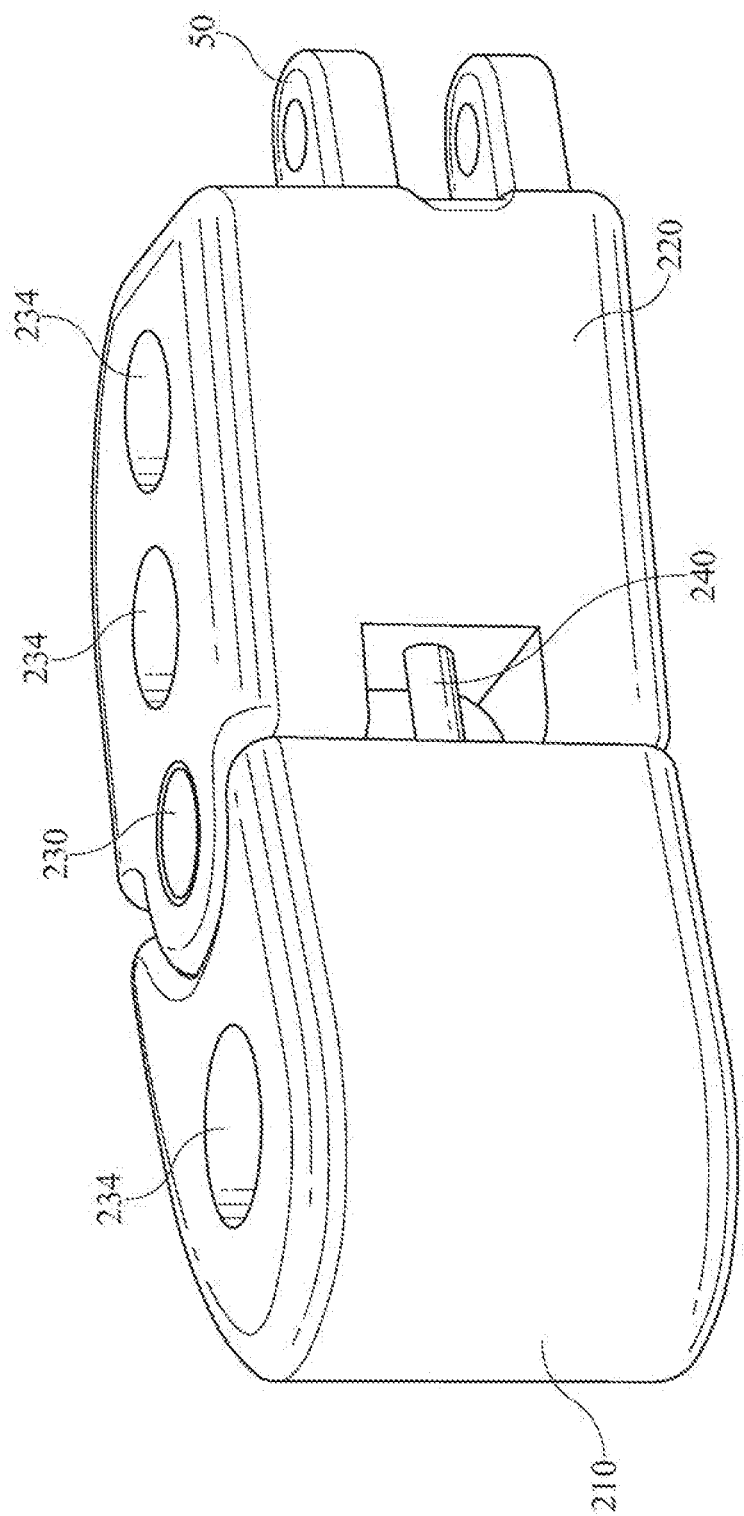
FIG. 14 is a perspective view of an inter-body device in accordance with one embodiment of the present invention.

FIGS. 10 and 11 depict central hinge 230 disposed approximately in the center of distal and proximal halves 210, 220, while FIG. 12 depicts hinge 230 disposed on the anterior edges of distal and proximal halves 210, 220 to permit flexure in the anterior direction. FIG. 13 depicts hinge 230 disposed on the posterior edges of distal and proximal halves 210, 220 to permit flexure in the posterior direction. Finally, FIG. 14 depicts a further embodiment of the invention having a plurality of apertures 234 therein to accept bone graft material to aid in vertebral fusion.

It should be noted that the embodiments of inter-body device 20 depicted in FIGS. 10-14 may also be employed as trial implants, whereby they are inserted into disc space 2 prior to insertion of a permanent implant to test fit disc space 2 for proper size and positioning, and to determine that disc space 2 is properly prepared to receive inter-body device 20. Where inter-body devices 20 are employed as trials, they may be manufactured of a suitable material capable of reuse after proper sterilization, as is well known in the surgical arts.

Figure 15:
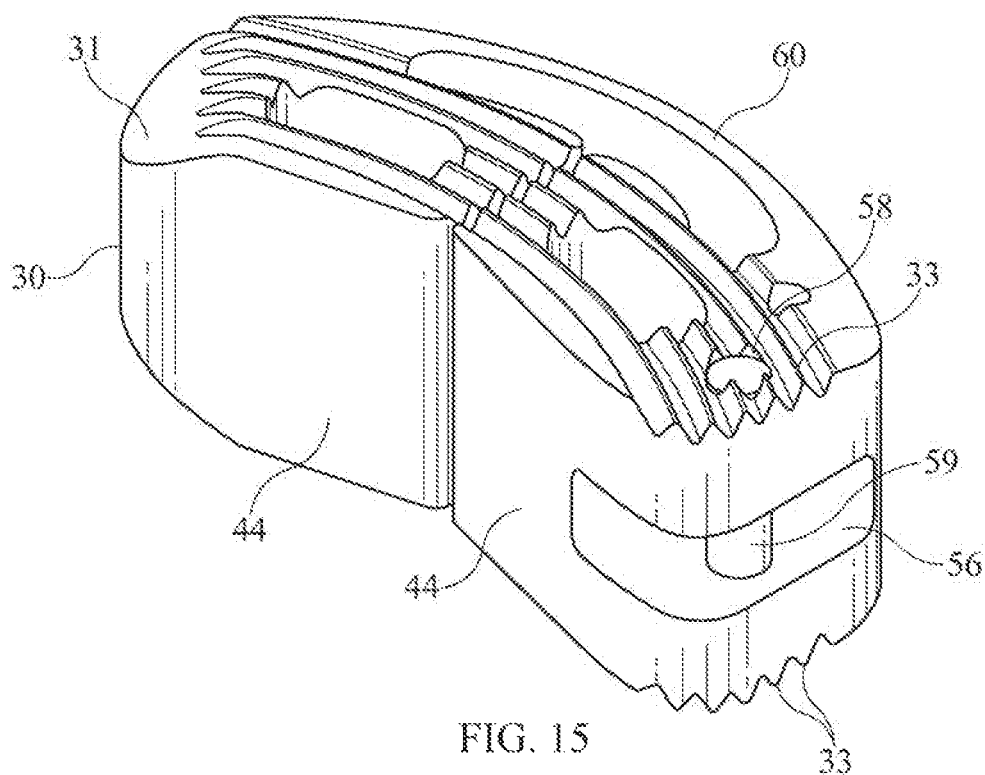
FIG. 15 is a perspective view of an inter-body device in accordance with one embodiment of the present invention.
Figure 16:
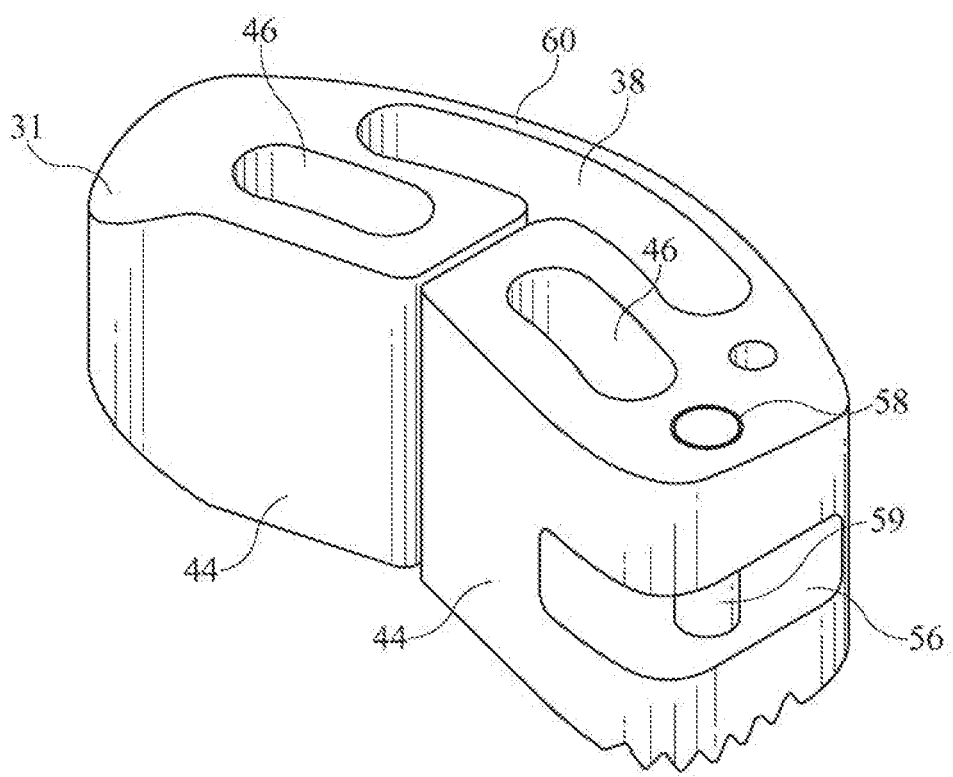
FIG. 16 is a perspective view of an inter-body device in accordance with one embodiment of the present invention.
Figure 17:
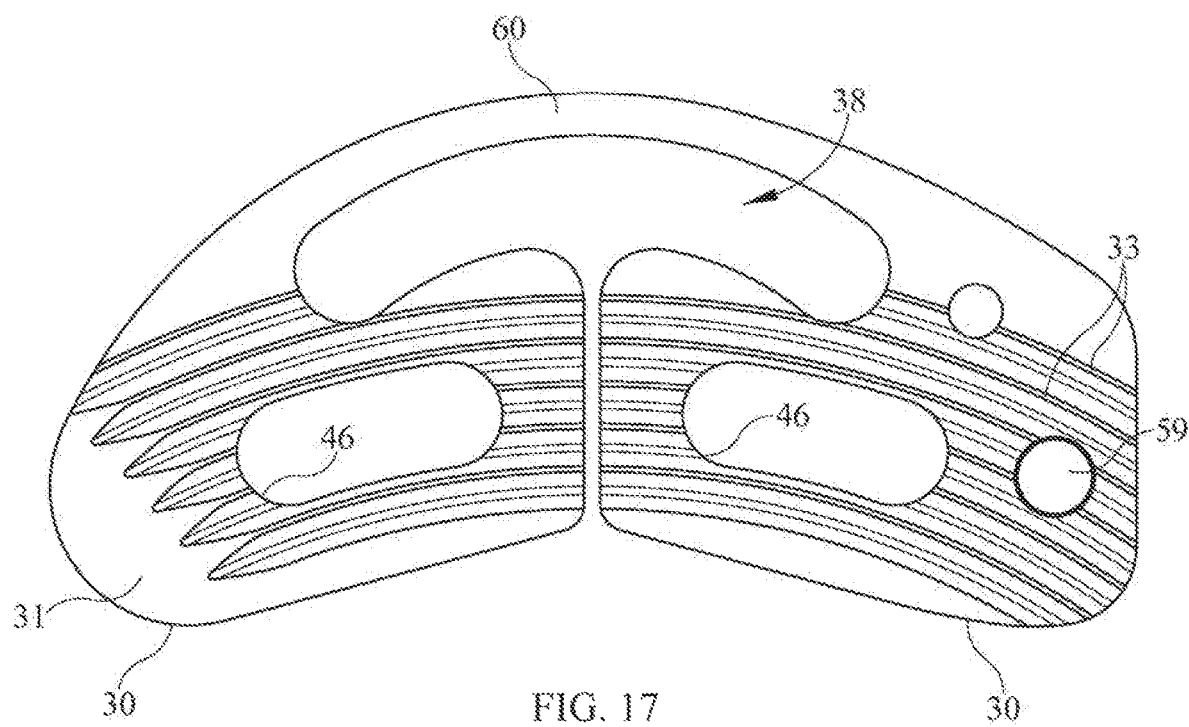
FIG. 17 is top view of an inter-body device in accordance with one embodiment of the present invention.
Figure 18:
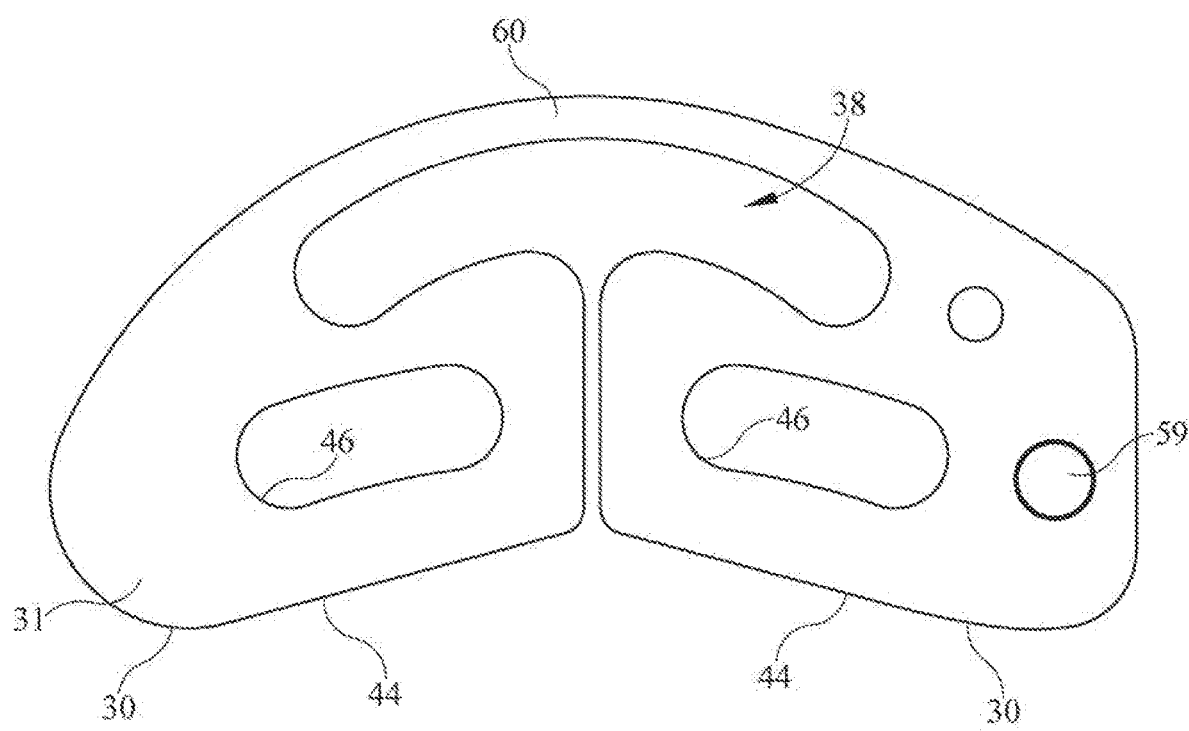
FIG. 18 is a top view of an inter-body device in accordance with one embodiment of the present invention.

Referring now to FIGS. 15-17, an exemplary embodiment of inter-body device 20 is shown formed of a single piece of material, whereby flexible bridge 60 is integral with a pair of spaced elongated cans 30, each having upper 34 and lower 36 surfaces with an aperture 46 therein for accepting bone graft material. The embodiment of the present invention depicted in FIGS. 15 and 17 further comprises a plurality of ridges 33 on upper 34 and lower 36 surfaces to facilitate vertebral engagement of device 20. Additionally, in this embodiment of the invention a portion of one can 30 comprises a void or slot 56 therein, that extends around an end of said can 30 and into posterior wall 44 thereof. Additionally, a pair of opposed apertures 58 communicate with slot 56 to accept a pin 59 that is secured in apertures 58. Pin 59 can then easily be accessed by an insertion and removal tool as discussed below.

Furthermore, in this embodiment of the invention flexible bridge 60 extends outwardly towards the distal and proximal ends, respectively, of cans 30 to define a relief area 38 that permits considerable flexure and straightening of device 20 as it is deployed through inserter tube 100. In a yet further embodiment of the invention, distal can 30 may comprise a beveled distal edge portion 31, best seen in FIGS. 15 and 16, that facilitates smooth entry of device 20 into disc space 2 since the height of distal can 30 is slightly less than the height of inter-body device 20 along the remainder of its length.

It is to be understood from the teachings of this specification that the embodiments of inter-body device 20 shown and described herein may be produced in a wide variety of sizes, varying in both overall length and height, as well as varying in spacing between cans 30 and bridge 60 such that the invention may be adapted for use in nearly any size disc space as required by a surgeon. Furthermore, it is to be understood that the inter-body devices 20 described herein may include a plurality of radiographic markers disposed at a plurality of points in or on said inter-body devices 20, to enable a surgeon to ensure proper placement of said devices 20 by conventional radiographic techniques.

Figure 19:
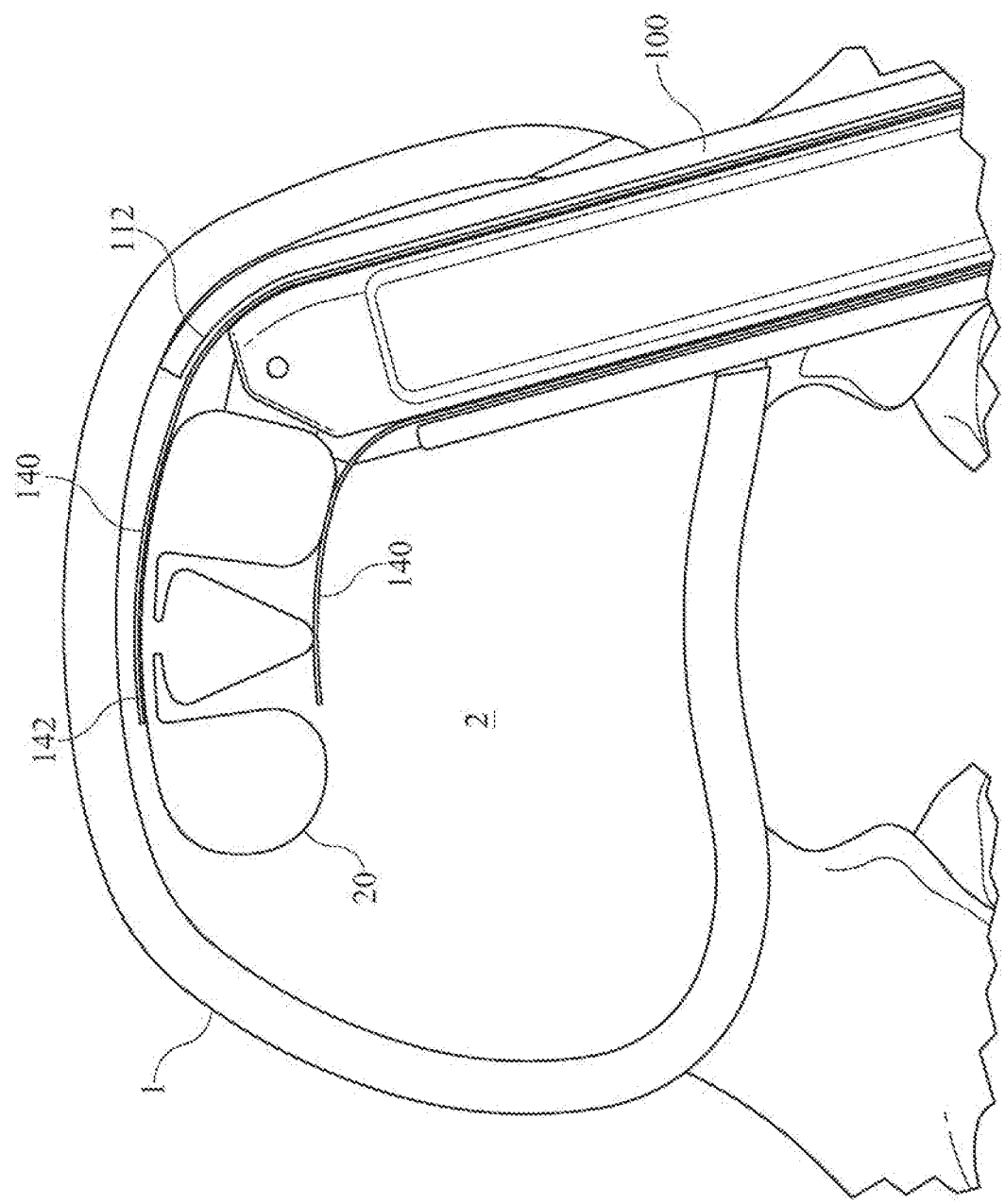
FIG. 19 is a top view of an inter-body device being advanced into a disc space in accordance with one embodiment of the present invention.

Referring now to FIG. 19 there is shown a flexible implant guide sleeve 140 that is sized to be inserted through inserter tube 100 into disc space 2. In this embodiment of the invention inter-body device 20 is carried by a distal end 142 of guide sleeve 140 until it is properly positioned in disc space 2 then guide sleeve 140 is retracted back into inserter tube 100. Guide sleeve 140 may advantageously be formed of a thin memory metal or equivalent flexible material capable of curving into disc space 2. Furthermore, in one embodiment of the invention the relaxed shape of guide sleeve 140 distal end 142 approximates that of inter-body device 20 and disc space 2 to facilitate placement of device 20 therein.

Figure 20:
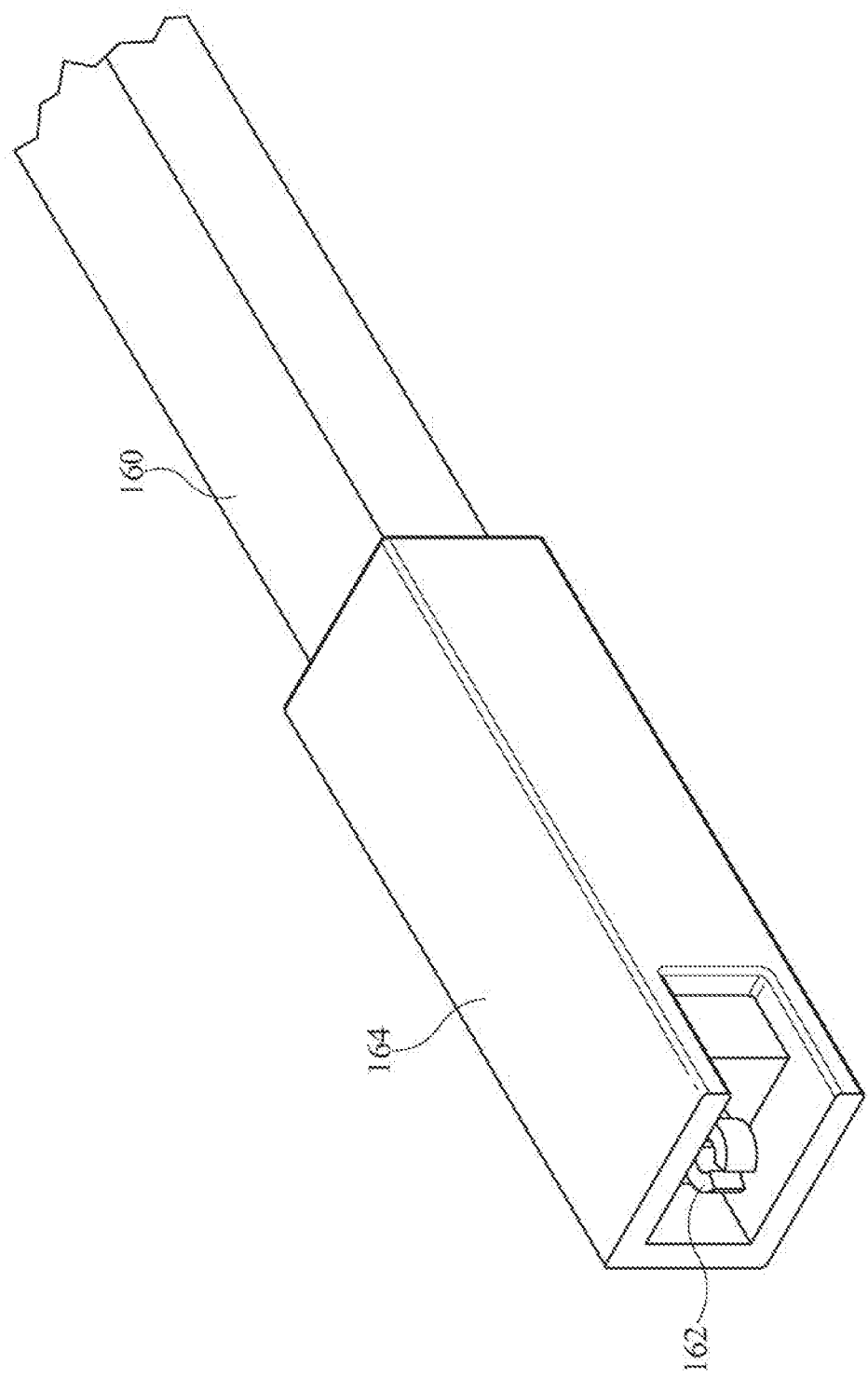
FIG. 20 is a perspective view of an inter-body device push rod in accordance with one embodiment of the present invention.

FIG. 20 depicts an inter-body device push rod 160 adapted to be inserted into the interior of inserter tube 100, having a clasp 162 at a distal end 164 thereof. Clasp 162 may be actuated by known-in-the art means to engage and release a pin 59 of an inter-body device 20, for example the device 20 depicted in FIG. 15. Distal end 164 of push rod 160 may be sized to fit into slot 56 of inter-body device 20, thereby enabling device 20 to rotate into disc space 2 before being release by disengagement of clasp 162.

Figure 21:
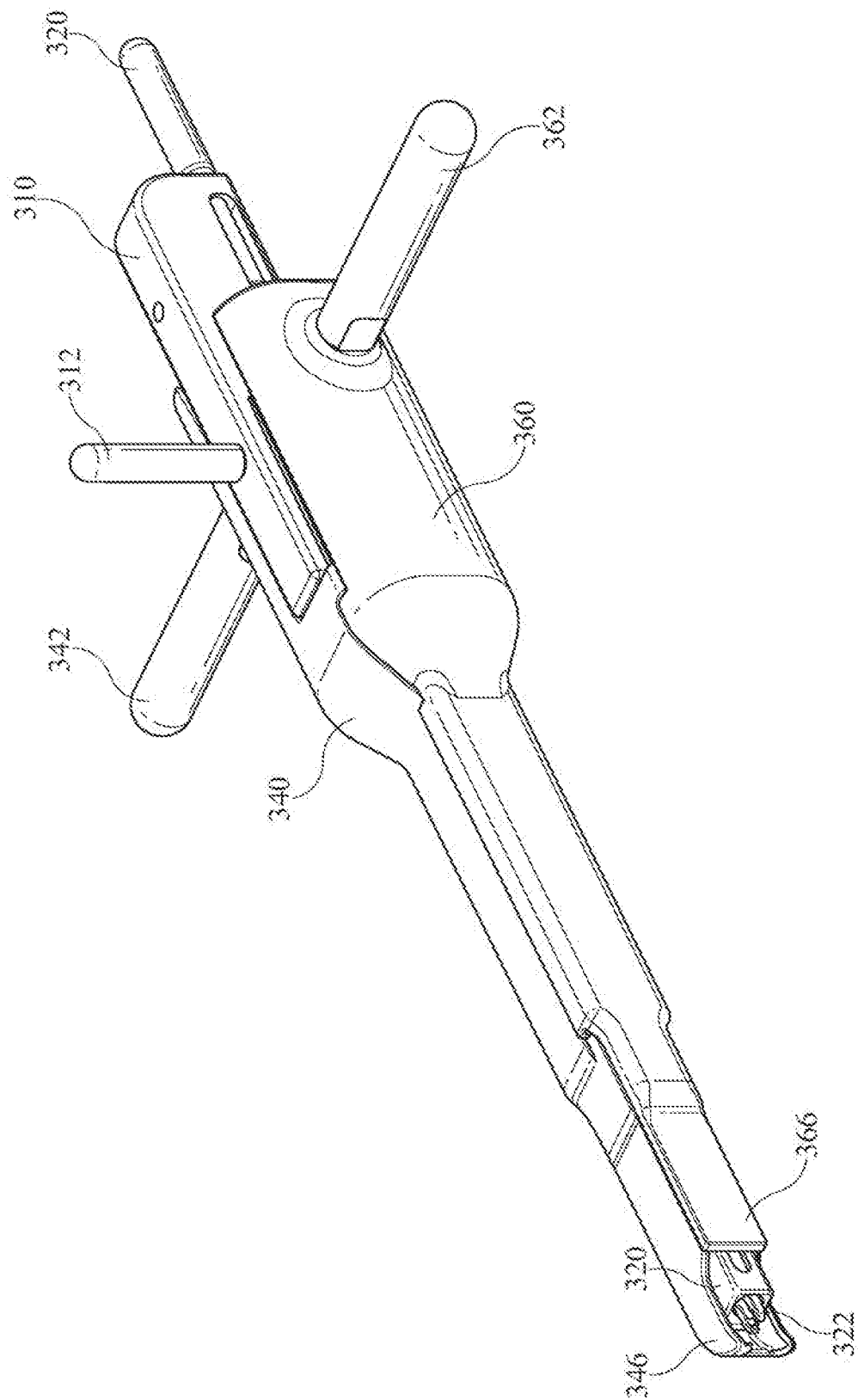
FIG. 21 is a perspective view of an insertion tool in accordance with one embodiment of the present invention.
Figure 22:
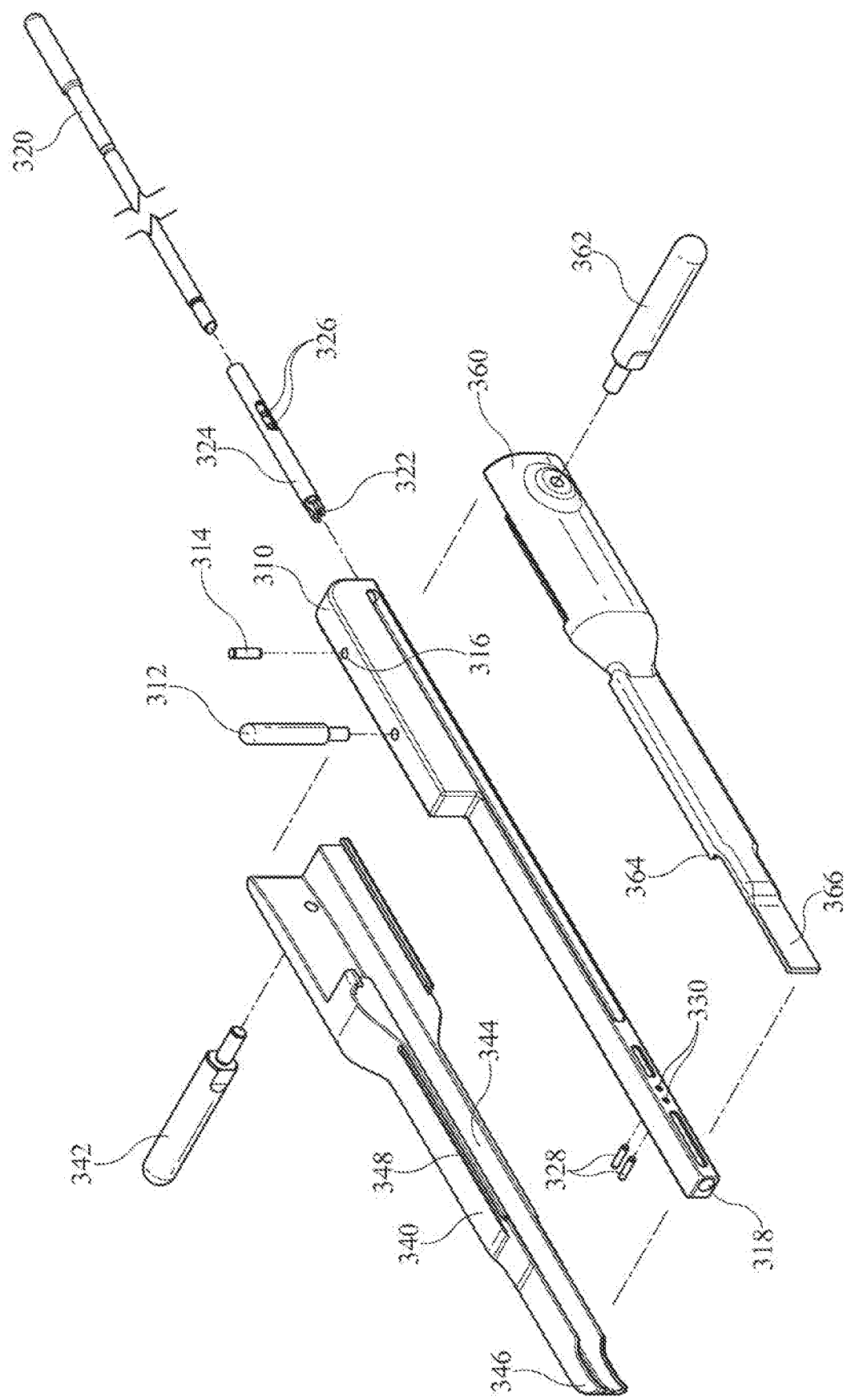
FIG. 22 is an exploded view of an insertion tool in accordance with one embodiment of the present invention.
Figure 23:
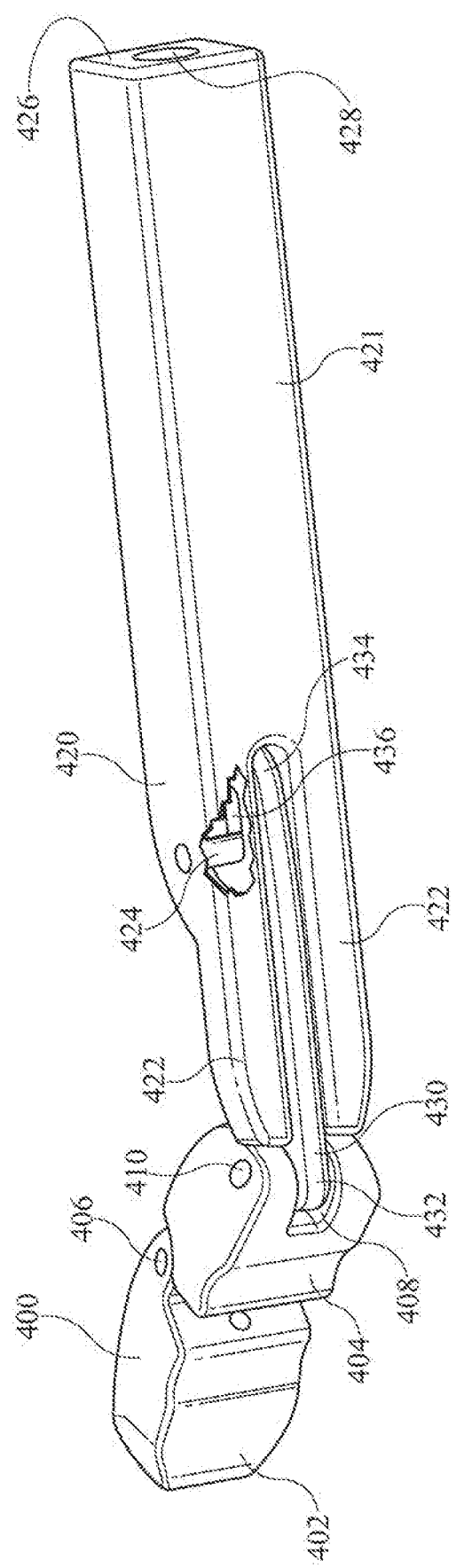
FIG. 23 is a perspective view of a trial implant in accordance with one embodiment of the present invention.

Referring now to FIGS. 21 and 22, there is depicted an alternative inter-body insertion tool 300 in accordance with one embodiment of the present invention. Insertion tool 300 comprises an elongated central body 310 having a handle 312 secured thereto and extending upwardly therefrom, and a lock button 314 that is inserted through an aperture 316 in an upper surface of central body 310. Central body 310 further includes a channel 318 that extends longitudinally through central body 310, shaped to accept an elongated shaft 320 having a clasp 322 at a distal end 324 thereof for engaging an inter-body device 20. Shaft 320 further comprises a pair of spaced apertures 326 therethrough that align with a complementary pair of spaced apertures 330 in central body 310, and into which a pair of locking pins 328 are inserted to secure shaft 320 into central body 310.

Insertion tool 300 further comprises a stationary member 340 that includes a handle 342 secured thereto and extending outwardly therefrom, and an elongated slot 344 that is shaped to engage elongated central body 310. Stationary member 340 comprises a distal tip 346 shaped to direct an inter-body device 20 into a disc space, as well as an elongated groove 348 in a portion thereof. Central body 310 fits closely into slot 344 of stationary member 340, and is slidable therein to enable central body 310 to be advanced forward such that clasp 22 extends into disc space 2 to position inter-body device 2.

Insertion tool 300 further comprises a sliding member 360, having a handle 362 extending therefrom and including a tongue 364 extending longitudinally on a portion of sliding member 360 that engages groove 348 of stationary member 340. Sliding member 360 further comprises a distal tip 366 that is generally flat. When assembled, and as best seen in FIG. 21, sliding member 360 and stationary member 340 form a channel into which an inter-body device 20 may be inserted, secured by clasp 322 of central body 310 shaft 220. Sliding member 360 is capable of moving forward relative to stationary member 340, thereby enabling distal tip 366 to enter and distract disc space 2 to facilitate device 20 delivery. Once so inserted, stationary member 340 and central body 310 are also inserted into disc space 2 for delivery of inter-body device 20. This feature of the instant invention provides an insertion tool 300 that assists in disc space distraction for ease of implant insertion.

Referring now to FIGS. 23, 32, 33, 36, and 37 the present invention further comprises a trial implant 400 for determining the proper size of a permanent inter-body device 20 to be deployed, having a distal end 402 and a proximal end 404 secured together via a central hinge 406 that enables ends 402, 404 to rotate in a single plane relative to each other. Trial implant 400 is shaped to generally conform to the shape of inter-body device 20 that will be deployed for permanent use in disc space 2. Proximal end 404 of trial implant 400 includes a slot 408 therein, and a pin 410 secured transversely to slot 408 for securing trial implant 400 in an articulating fashion to a trial implant rod 420.

Trial implant rod 420 comprises an elongated body 421 terminating in a pair of spaced distal tips 422 that abut trial implant 400 at their distal ends. Trial implant rod further comprises a pin hinge 424 that extends through and is secured to both spaced distal tips 422 and a proximal end 426 having a threaded aperture therein for engagement with a trial implant insertion tool. An articulating arm 430 having an aperture at a distal end 432 thereof is rotatably secured to pin 410 of trial implant 400. Articulating arm 430 further comprises a proximal end 434 having a slot 436 therein that is engaged by hinge pin 424 of implant rod 420 so that articulating arm 430 is capable of both rotational and longitudinal movement with respect to implant rod 420. Furthermore, since trial implant 400 rotates around pin 410, both implant 400 and articulating arm 430 are capable of rotational motion with respect to implant rod 420.

Figure 32:
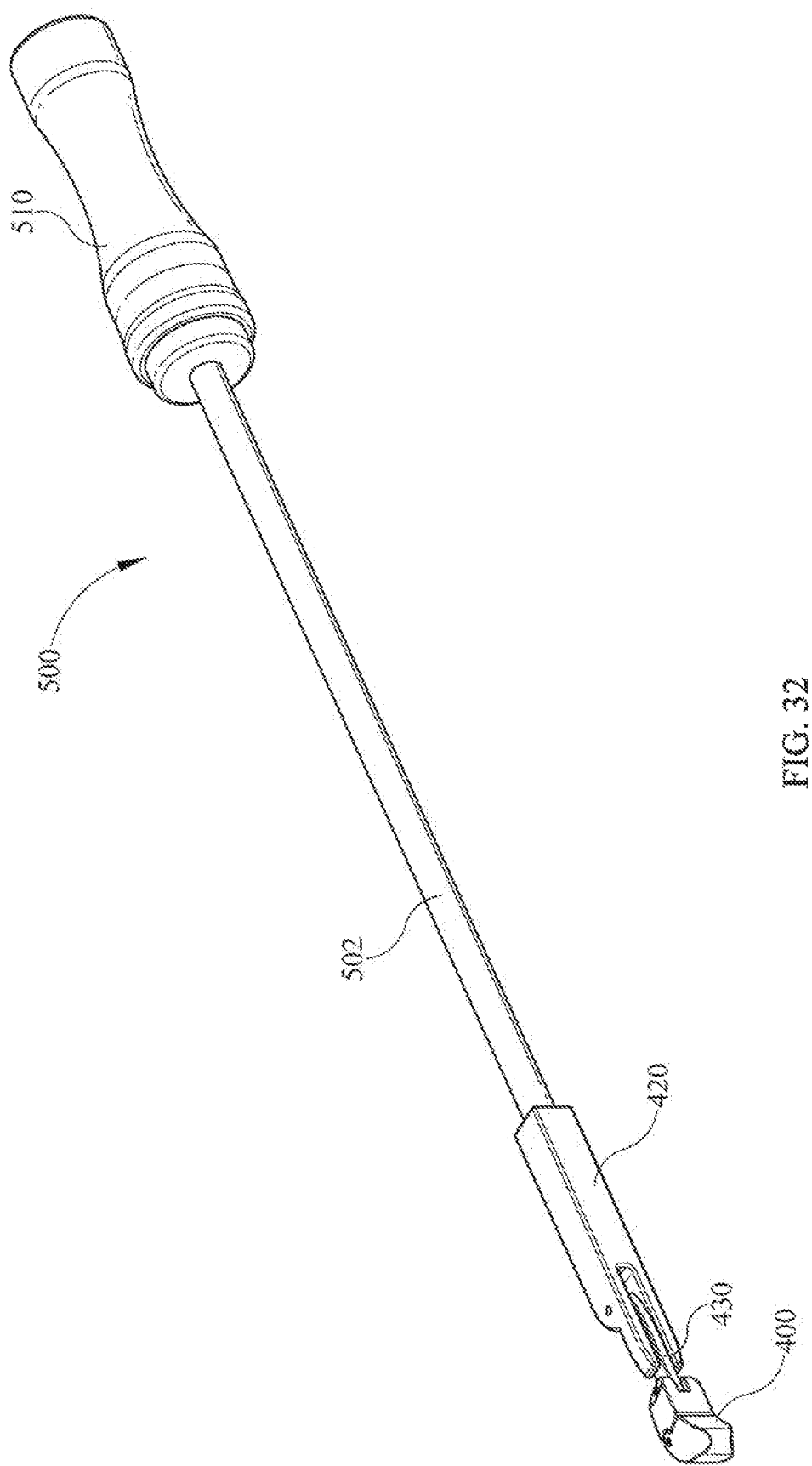
FIG. 32 is a perspective view of a trial implant and trial handle in accordance with one embodiment of the present invention.
Figure 33:
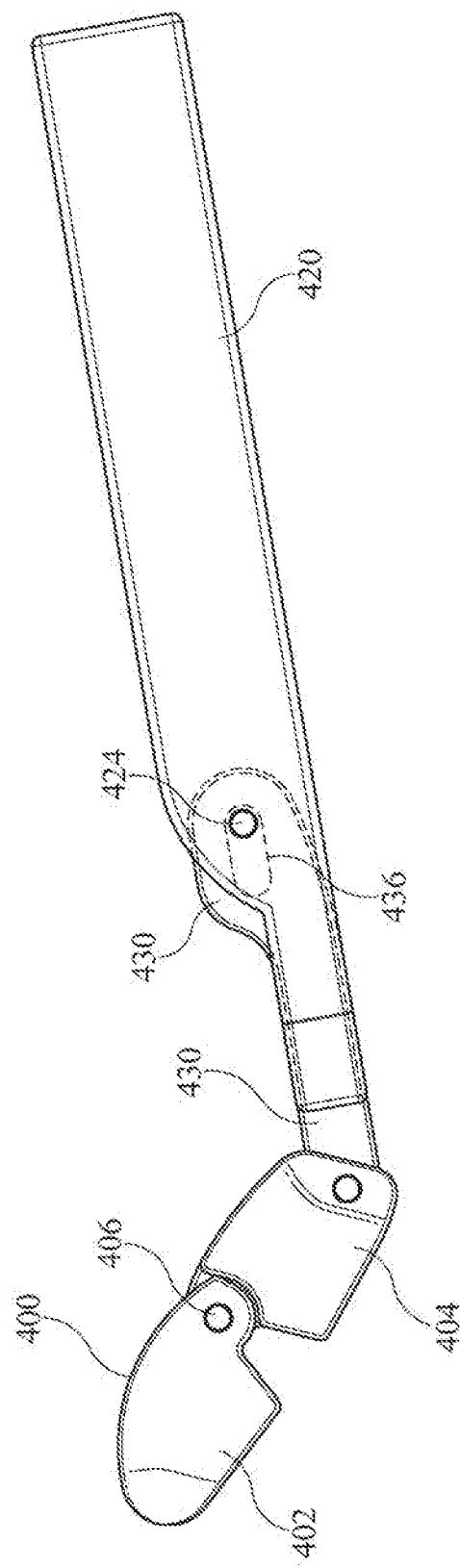
FIG. 33 is a side view of a trial implant in accordance with one embodiment of the present invention.
Figure 36:
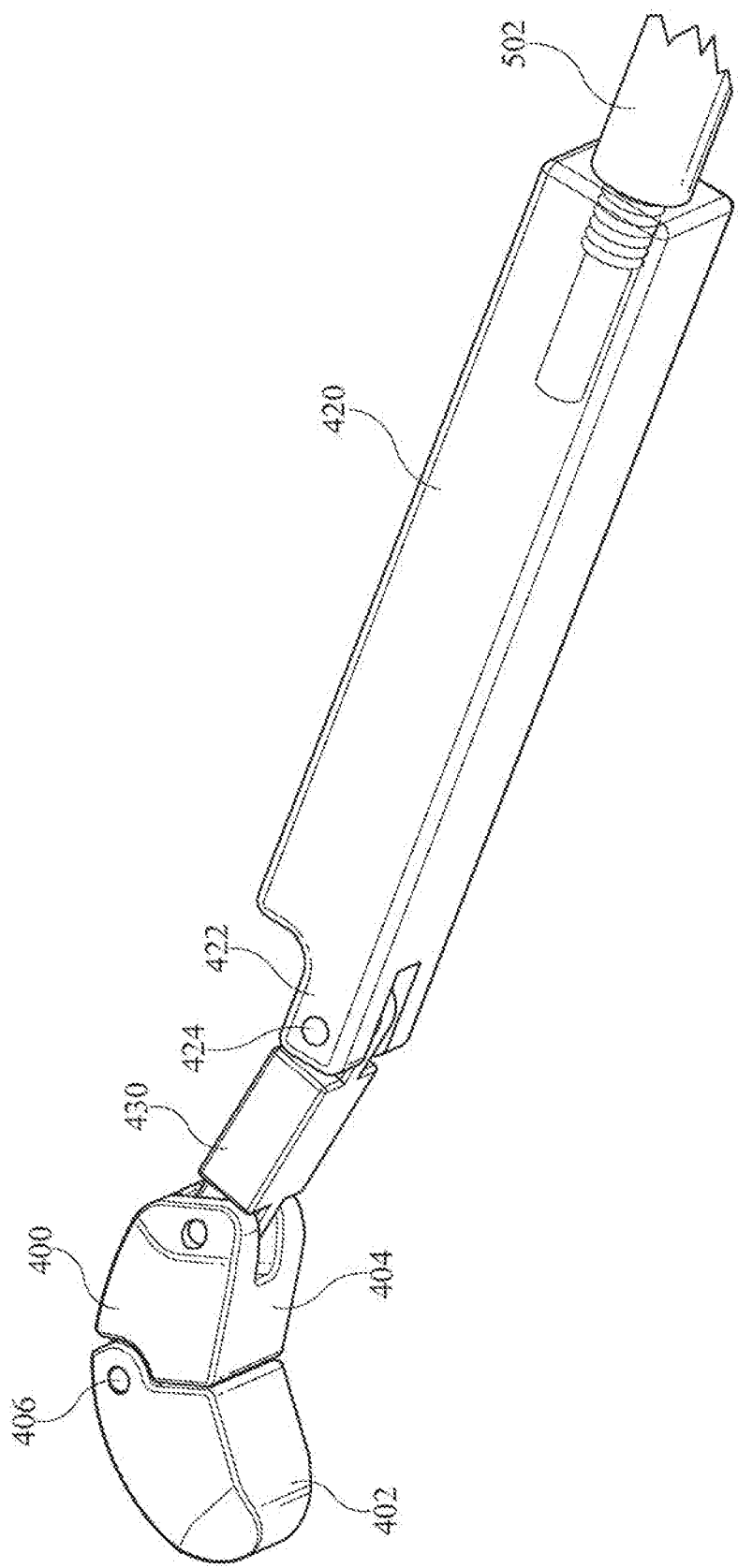
FIG. 36 is a perspective view of a trial implant and implant rod in accordance with one embodiment of the present invention.
Figure 37:
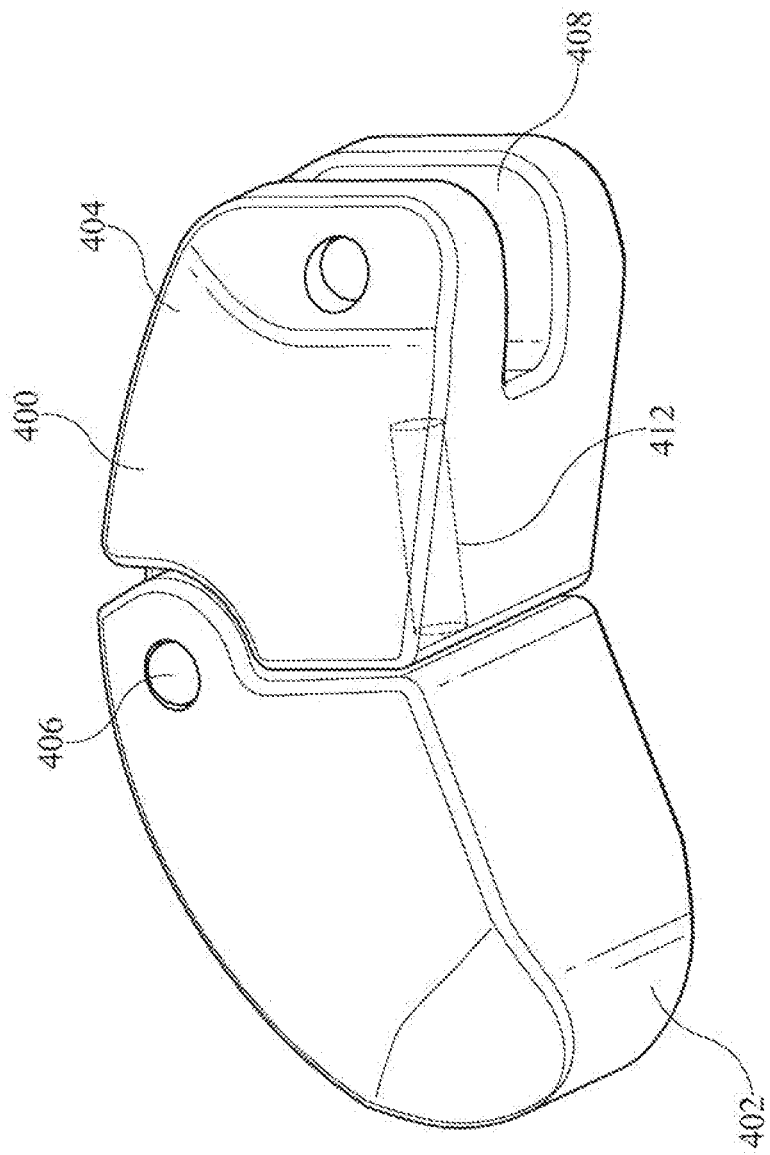
FIG. 37 is a perspective view of a trial implant in accordance with one embodiment of the present invention.
Figure 38:
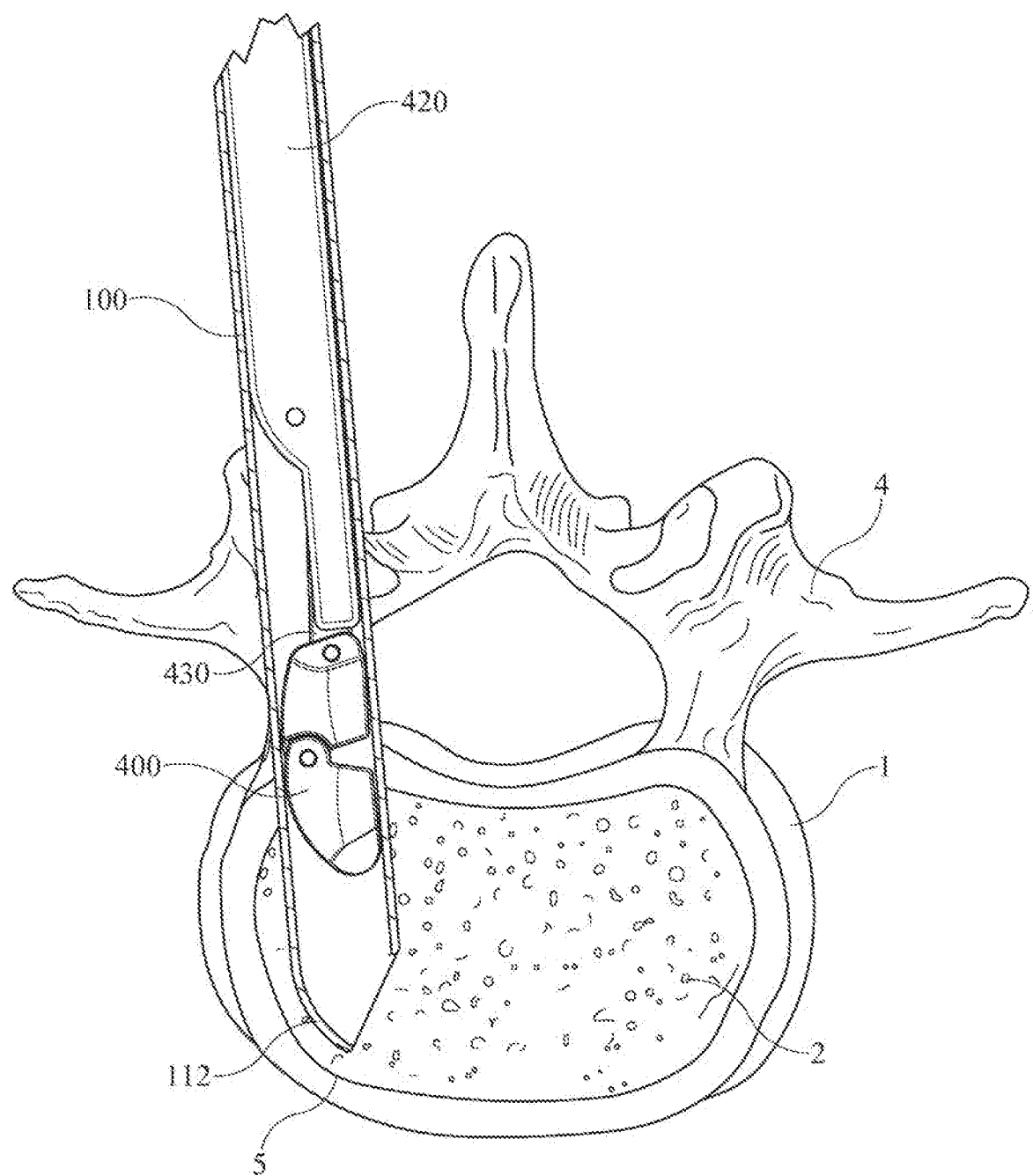
FIG. 38 is a top view of an inserter tube and trial implant advancing into a disc space in accordance with one embodiment of the present invention.
Figure 39:
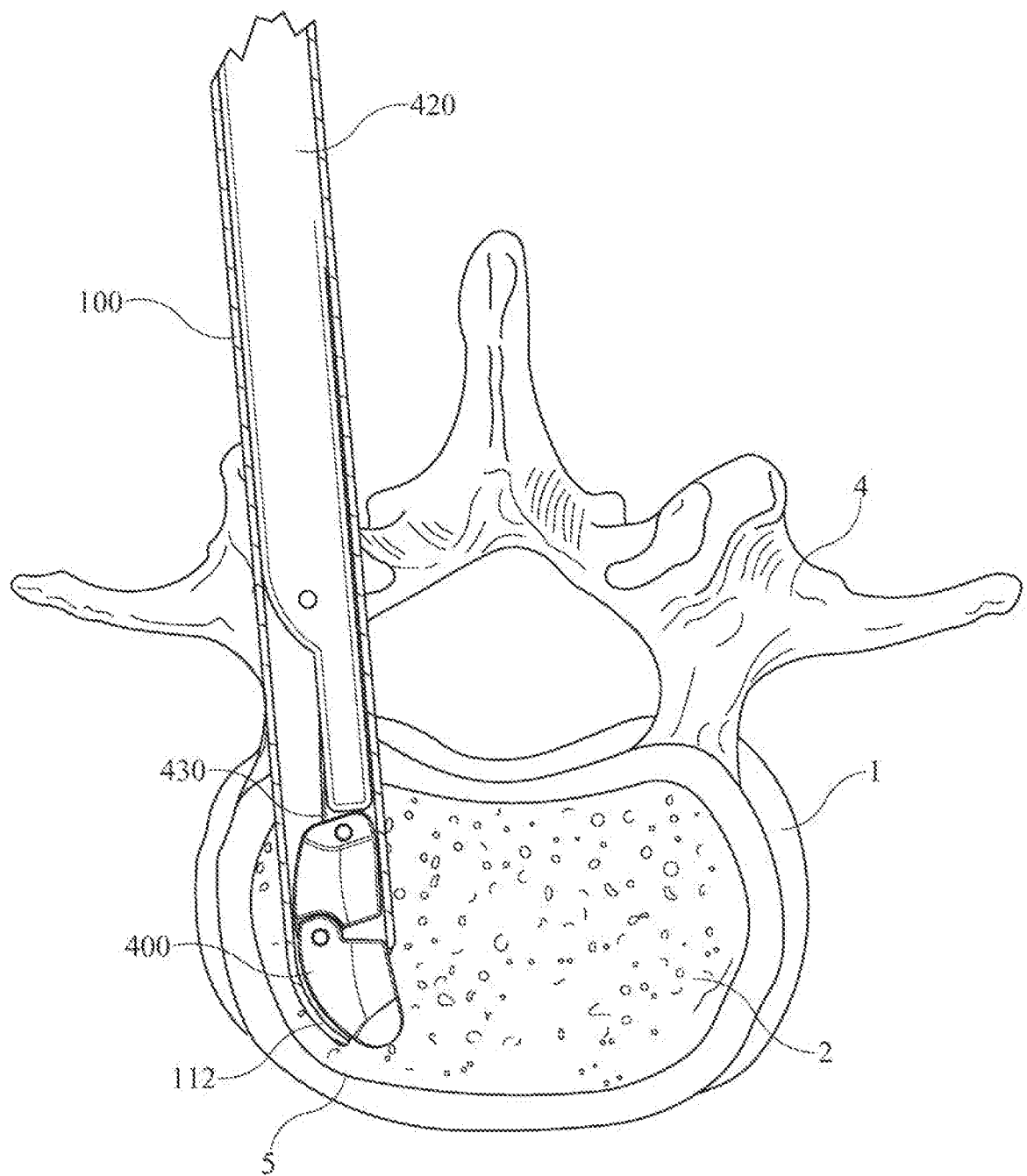
FIG. 39 is a top view of an inserter tube and trial implant advancing into a disc space in accordance with one embodiment of the present invention.
Figure 40:
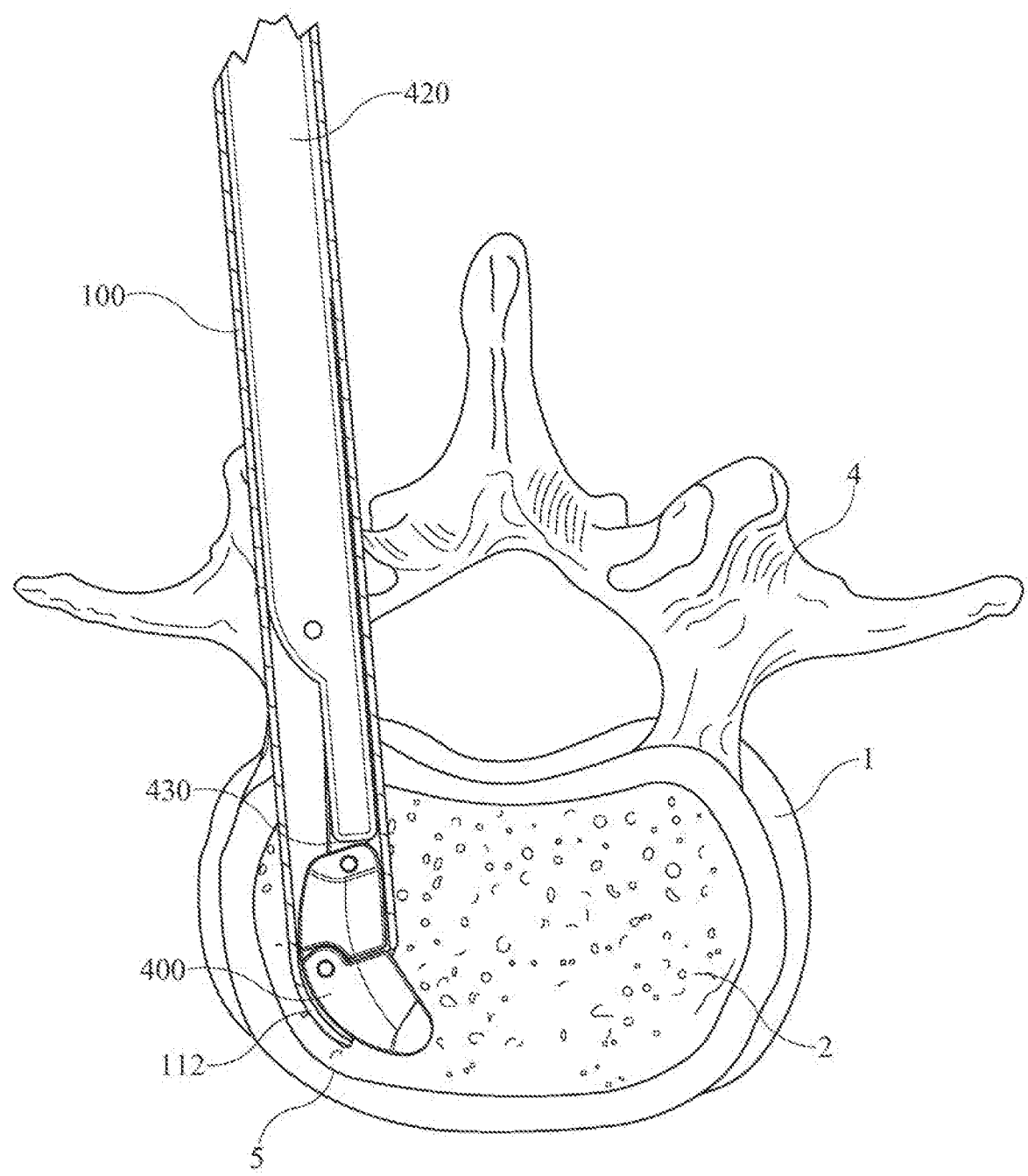
FIG. 40 is a top view of an inserter tube and trial implant advancing into a disc space in accordance with one embodiment of the present invention.
Figure 41:
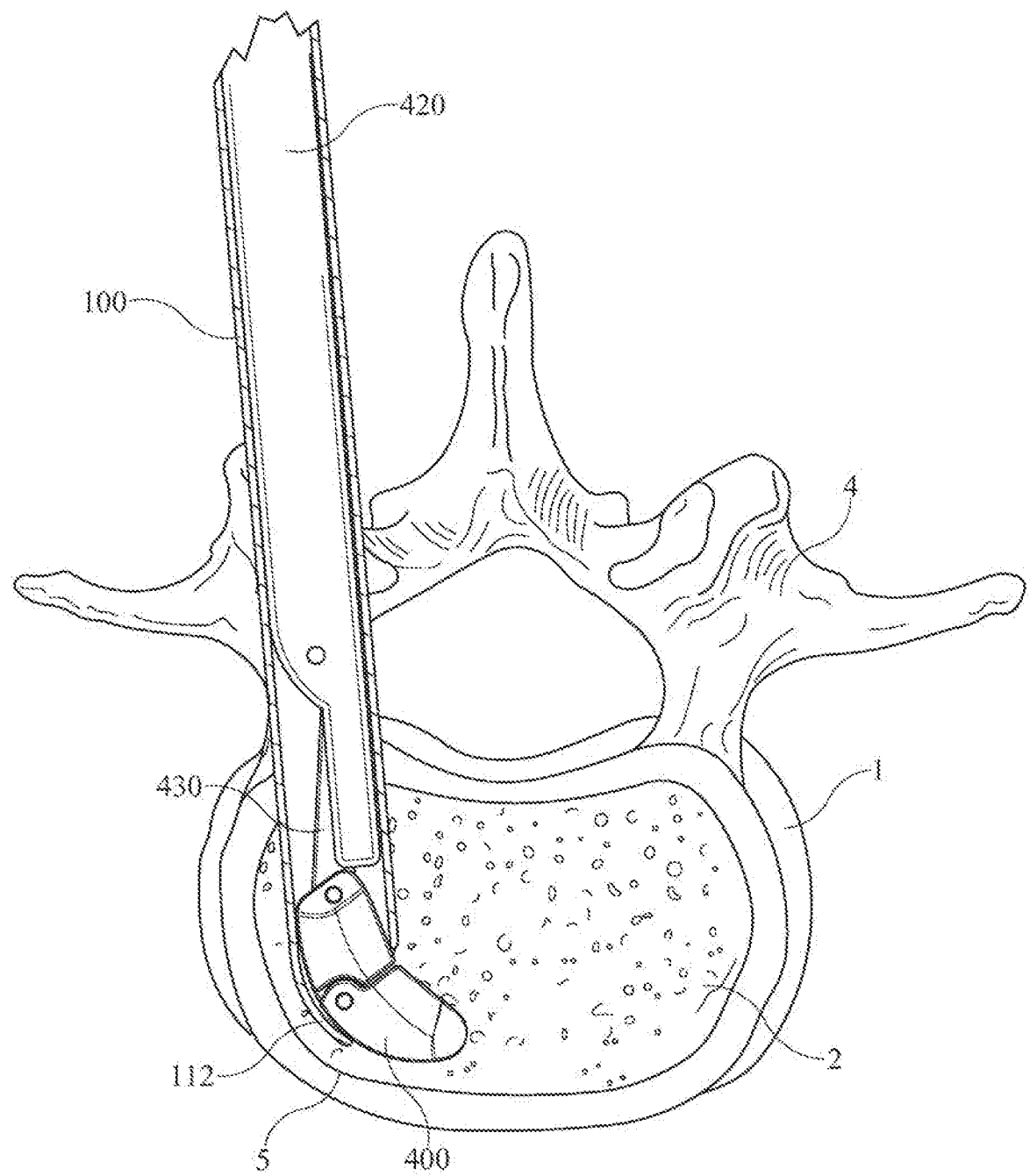
FIG. 41 is a top view of an inserter tube and trial implant advancing into a disc space in accordance with one embodiment of the present invention.
Figure 42:
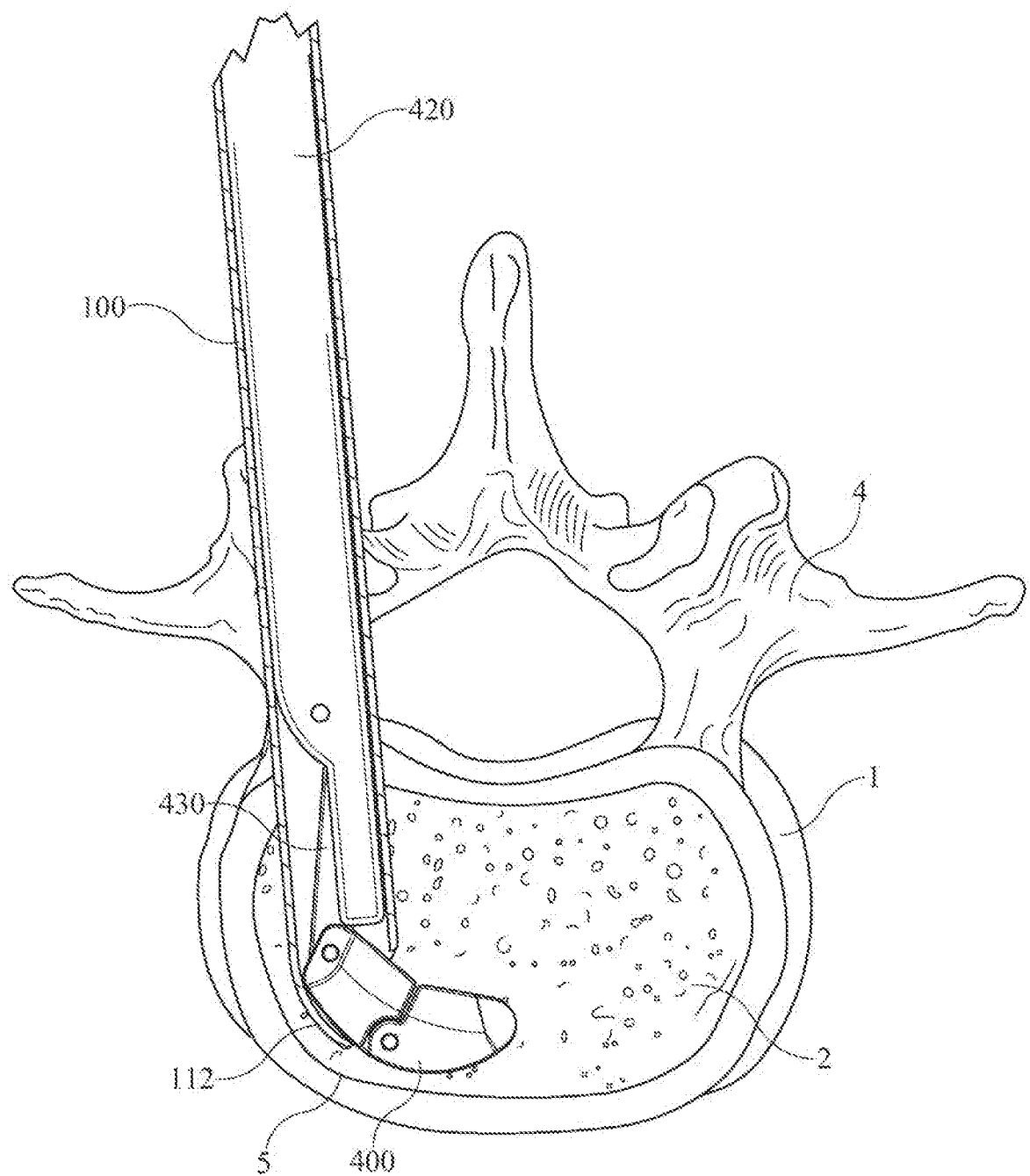
FIG. 42 is a top view of an inserter tube and trial implant advancing into a disc space in accordance with one embodiment of the present invention.
Figure 43:
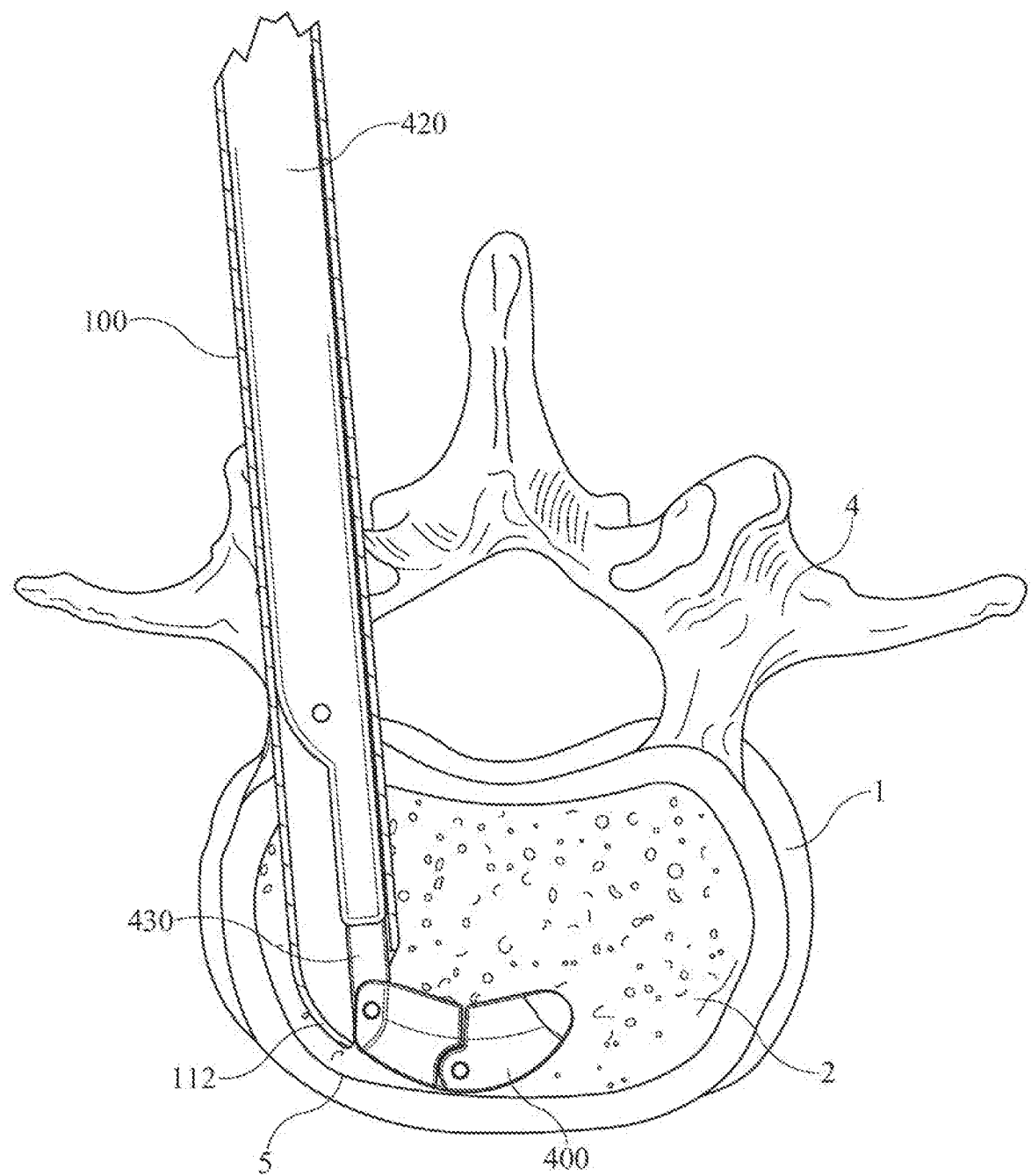
FIG. 43 is a top view of an inserter tube and trial implant advancing into a disc space in accordance with one embodiment of the present invention.

FIG. 32 depicts trial implant 400 and implant rod 420 secured to an insertion tool 500 having a trial handle 510 secured to a threaded shaft 502. It should be noted that trial handle 510 is designed to connect to a plurality of components of the present invention, as will be discussed further herein below. FIG. 36 depicts an alternative embodiment of trial implant rod 420 wherein distal tips 422 include hinge 424 at a distal portion thereof such that articulating arm 430 extends outwardly toward trial implant 400. As seen in FIG. 37 trial implants 400 may further include a flexible spine 412 inside distal and proximal ends 402, 404, similar to those embodiments shown in FIGS. 10-14.

Figure 24:
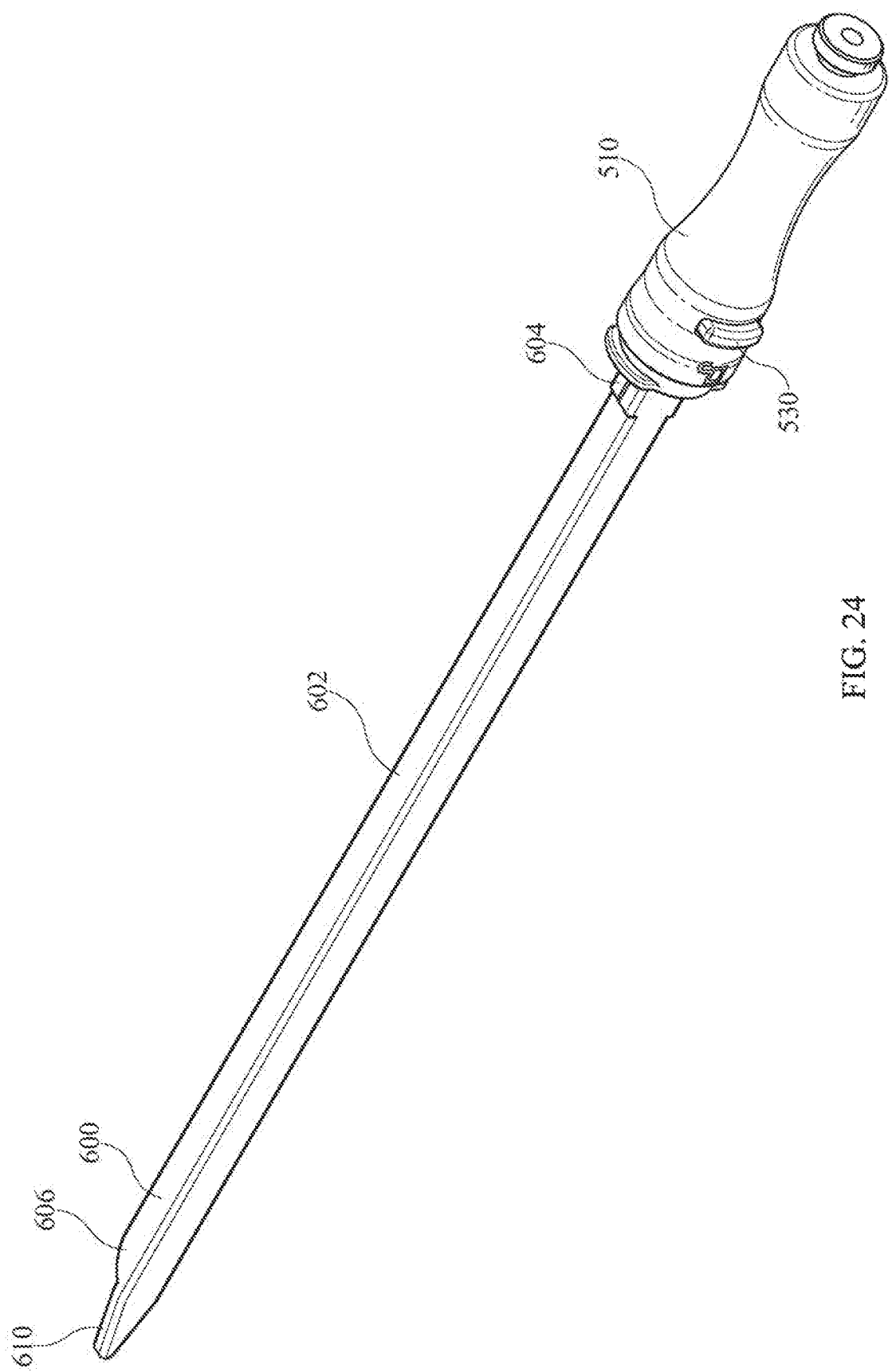
FIG. 24 is a perspective view of a bullnose and trial handle in accordance with one embodiment of the present invention.
Figure 25:
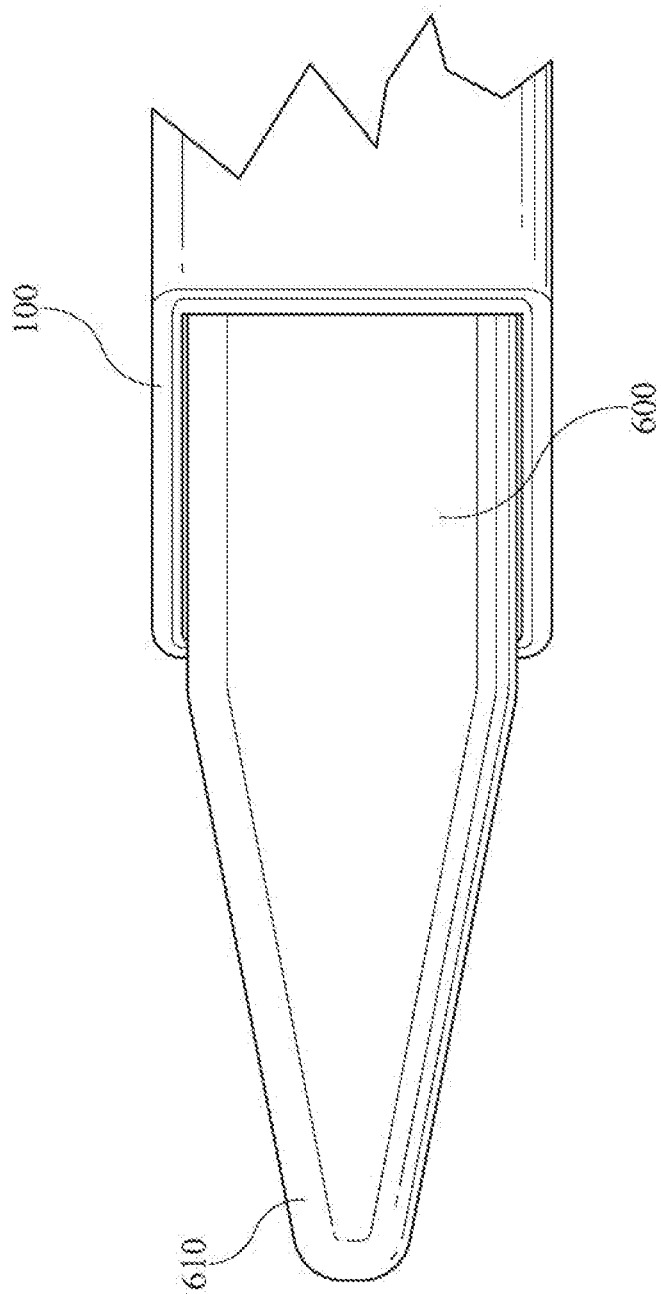
FIG. 25 is a partial view of a bullnose and inserter in accordance with one embodiment of the present invention.
Figure 26:
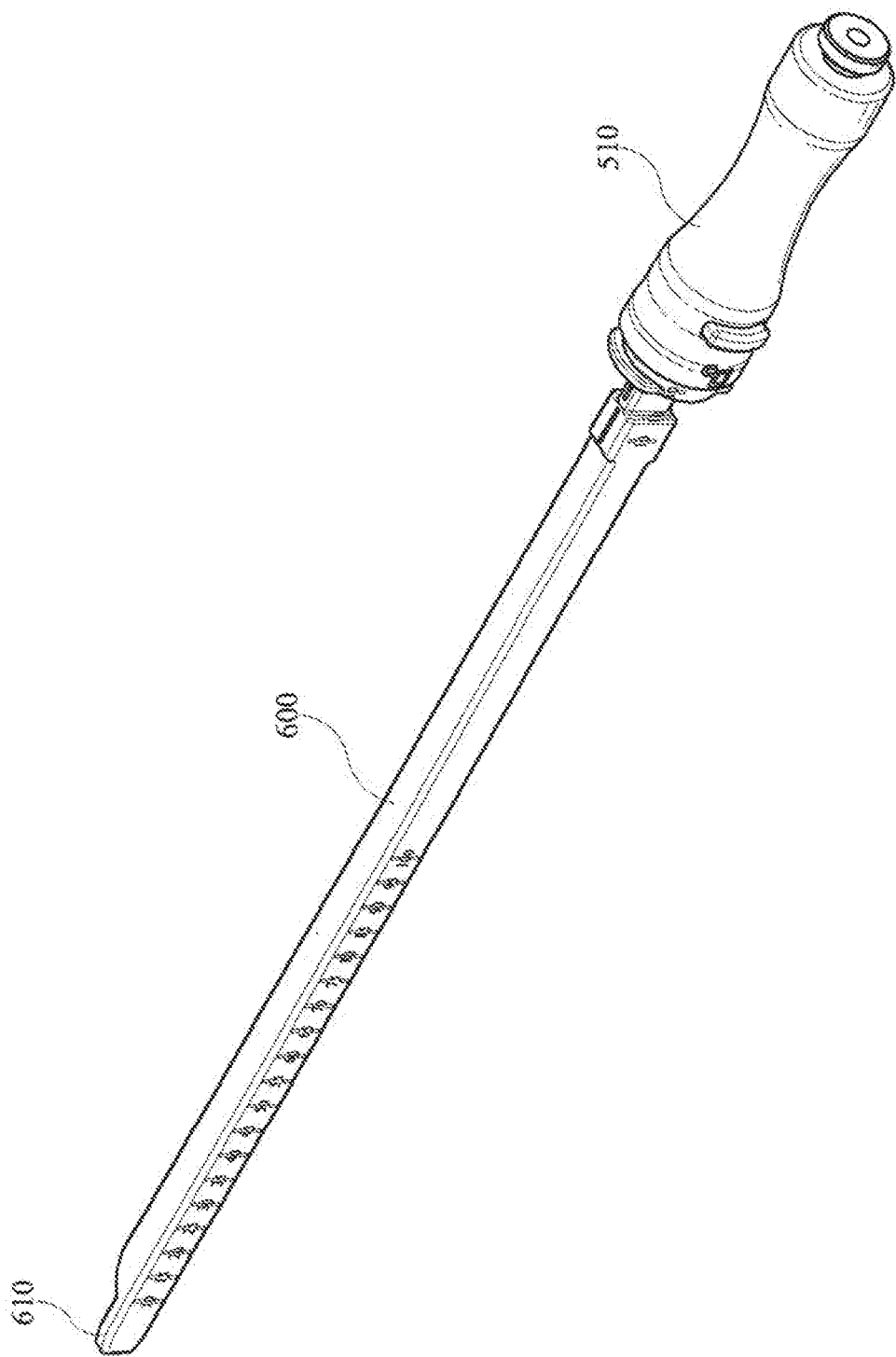
FIG. 26 is a perspective view of a trial implant in accordance with one embodiment of the present invention.
Figure 27:
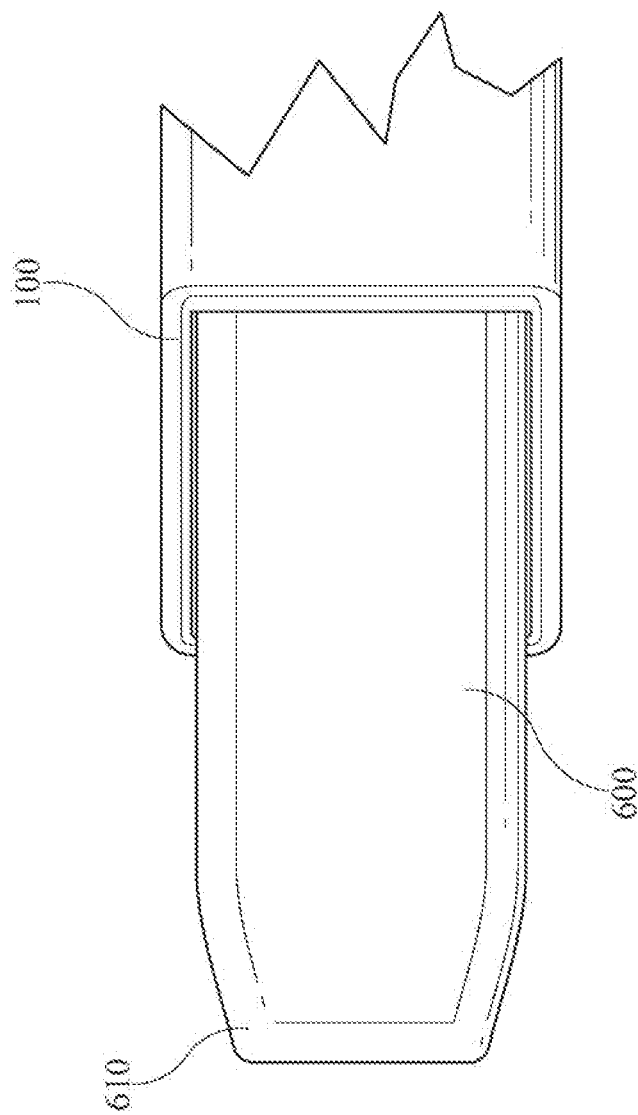
FIG. 27 is a partial view of a bullnose and inserter in accordance with one embodiment of the present invention.
Figure 28:
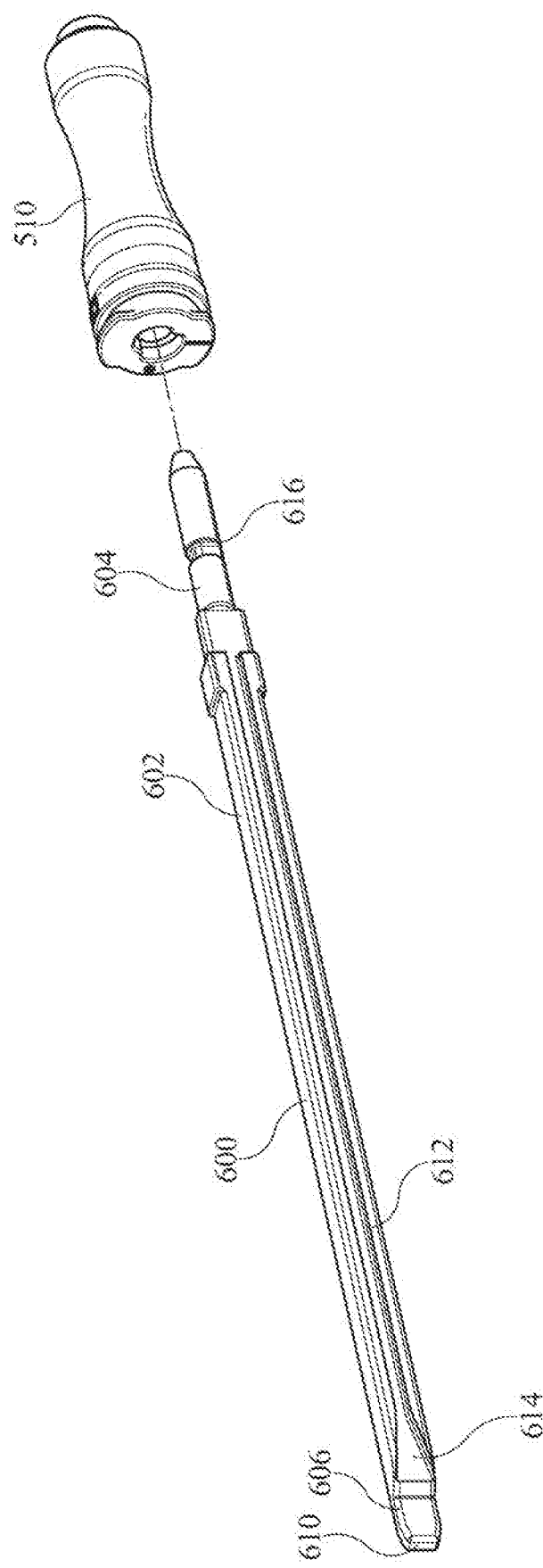
FIG. 28 is an exploded view of a bullnose and trial handle in accordance with one embodiment of the present invention.

FIG. 24 depicts a trial handle 510 secured to a bullnose 600 designed to aid in distraction of disc space 2 as well as insertion of inter-body devices 20 therein. Bullnose 600 comprises an elongated shaft 602 capable of engaging and being secured to handle 510 at a proximal end 604 thereof, and a distal end 606 having a tapered distal tip 610 thereon, for inserting into and distracting disc space 2. FIG. 25 depicts bullnose 600 distal tip 610 exiting distal end 110 of inserter tube 100.

Figure 29:
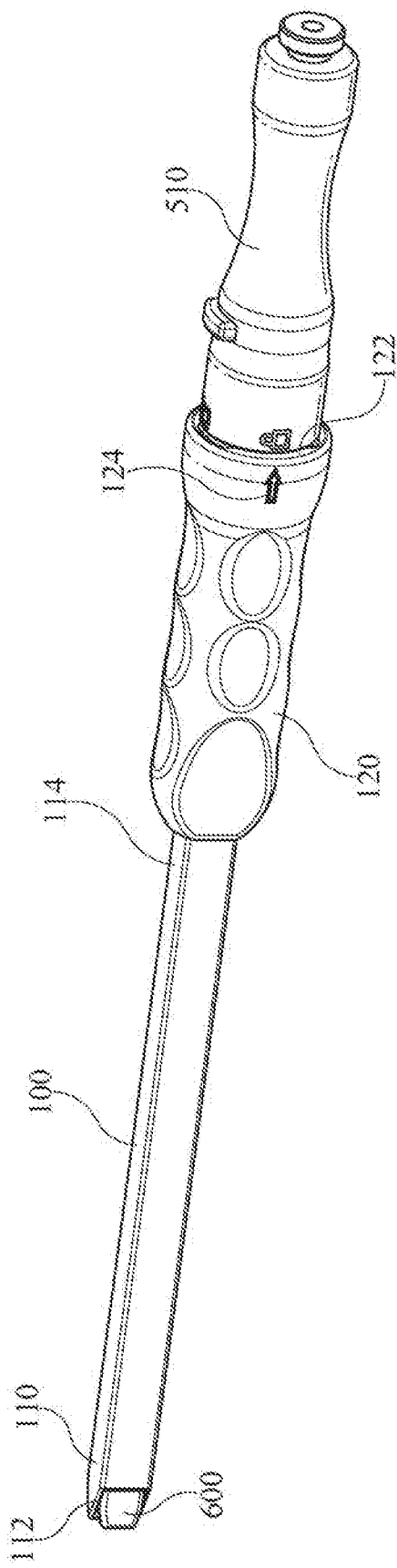
FIG. 29 is a perspective view of an assembled bullnose and trial handle in an inserter tube in accordance with one embodiment of the present invention.

FIGS. 26-29 depict an alternative embodiment of bullnose 600 utilized for inter-body device 20 insertion having a blunt distal tip 610 at distal end 606. Shaft 602 includes a suture 3 guide groove 612 along a substantial portion thereof that terminates in a wide groove end 614 proximate distal end 606 of bullnose 600. Guide groove 612 provides a space in which suture 3 is disposed when bullnose 600 is inserted through inserter tube 100, as shown in FIG. 29. Bullnose 600 proximal end 604 further includes an annular groove 616 that is engaged by a latch (such as a pin or spring-loaded ball, not shown) interior to handle 510. In operation, suture 3 may be secured to inter-body device 20 as shown in FIGS. 1-3 and may ride in groove 612 of bullnose 600 as it is advanced through inserter tube 100 into disc space 2.

Figure 34:
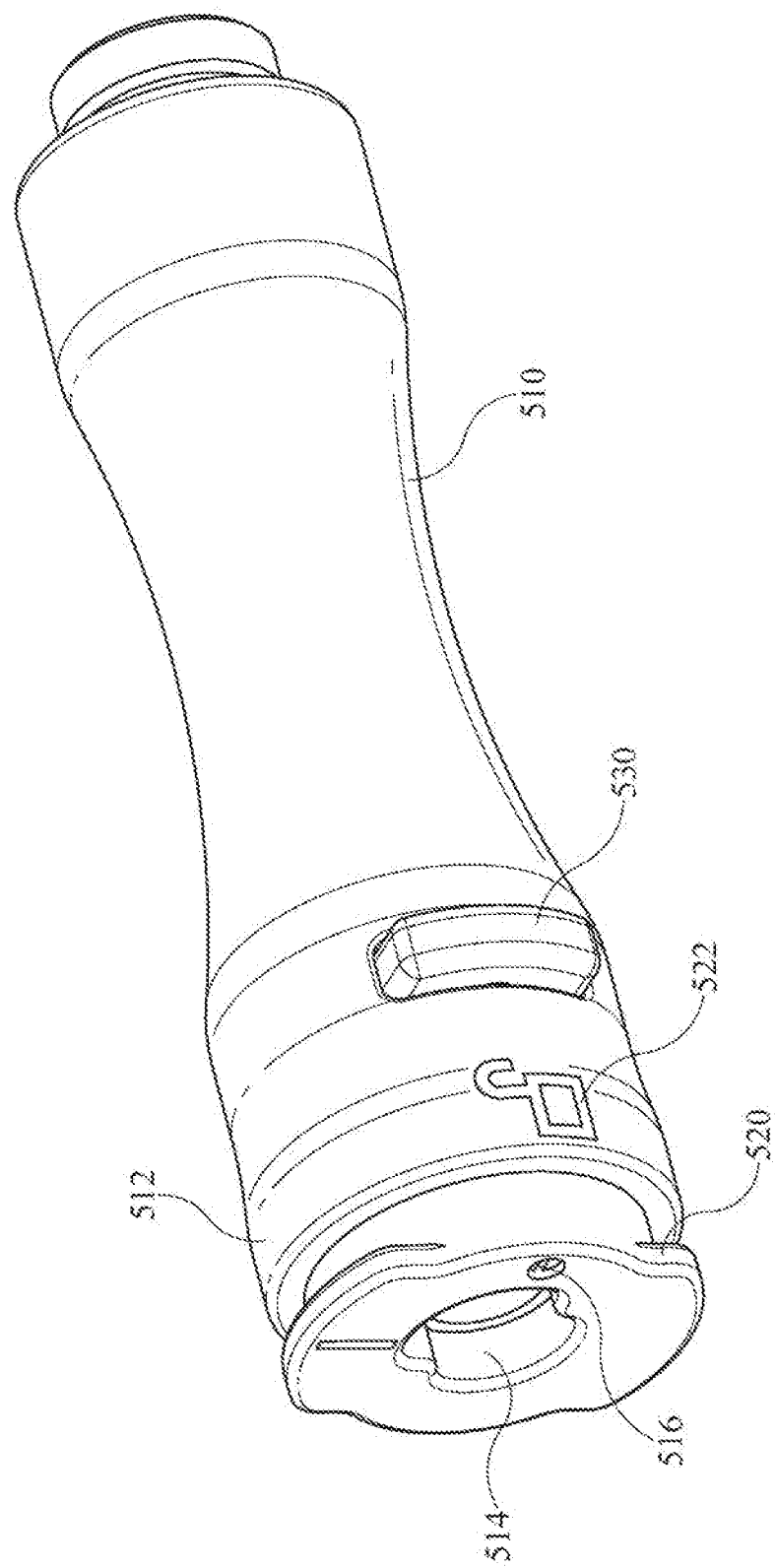
FIG. 34 is a perspective view of a trial handle in accordance with one embodiment of the present invention.
Figure 35:
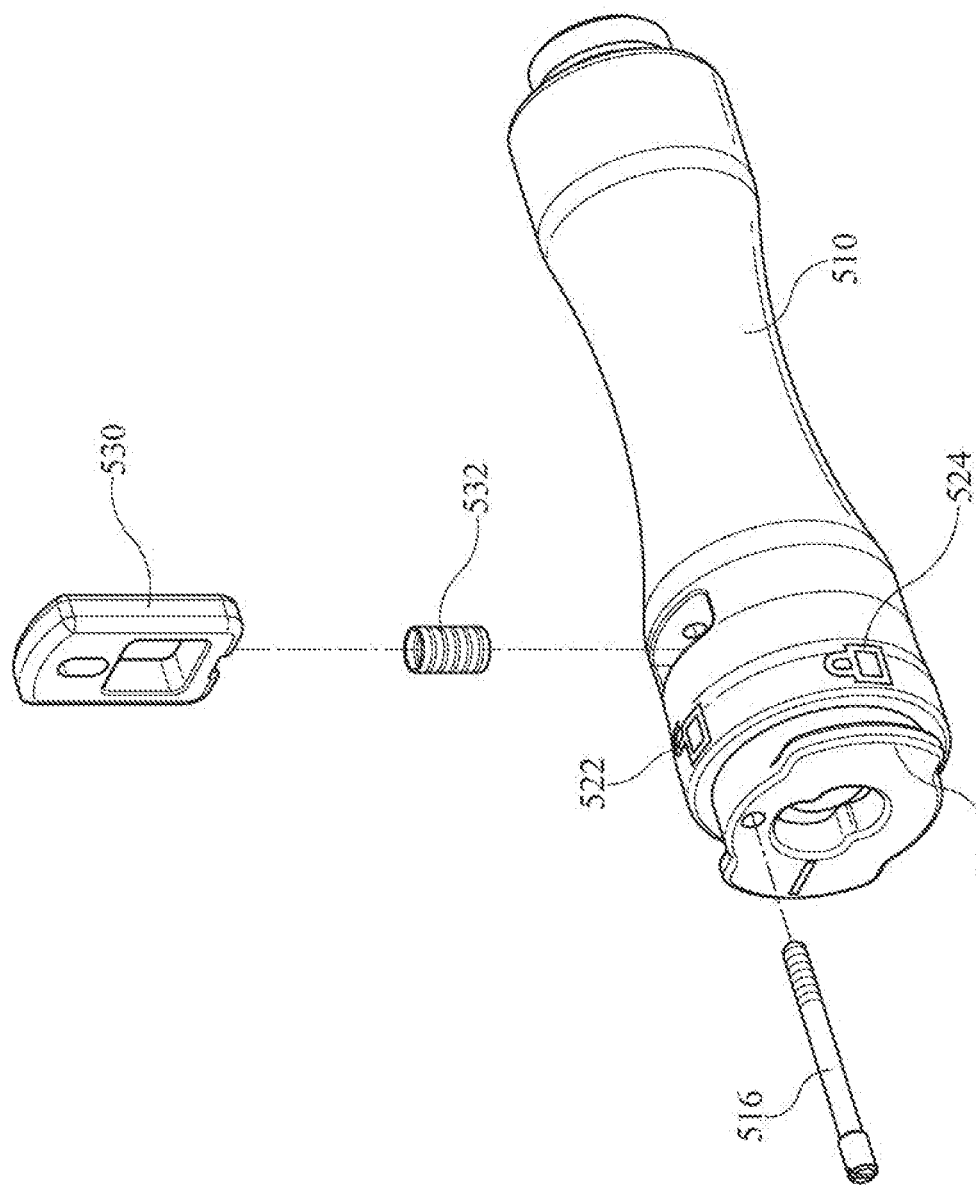
FIG. 35 is an exploded view of a trial handle in accordance with one embodiment of the present invention.

Referring again to FIG. 28 and to FIGS. 34 and 35, trial handle 510 is shown in further detail. Handle 510 includes a distal end 512 having an aperture 514 therein for engaging a proximal end 604 of bullnose 600. A locking flange 520 is also disposed on distal end 512 of handle 510 for engaging a complementary flange of, for example, inserter tube 100. Handle 510 may also include lock 524 and unlock 522 marks on an exterior surface thereof indicating that inserter tube 100 is locked onto handle 512 when a corresponding mark on tube 100 is aligned with lock mark 524, and alternatively unlocked with a corresponding mark on tube 100 is aligned with unlock mark 522. Handle 522 may include a release button 530 that is biased by spring 532 to engage (or disengage) a locking pin 516 extending through the distal end 512 thereof, for releasing bullnose 600 from engagement with handle 510.

Figure 30:
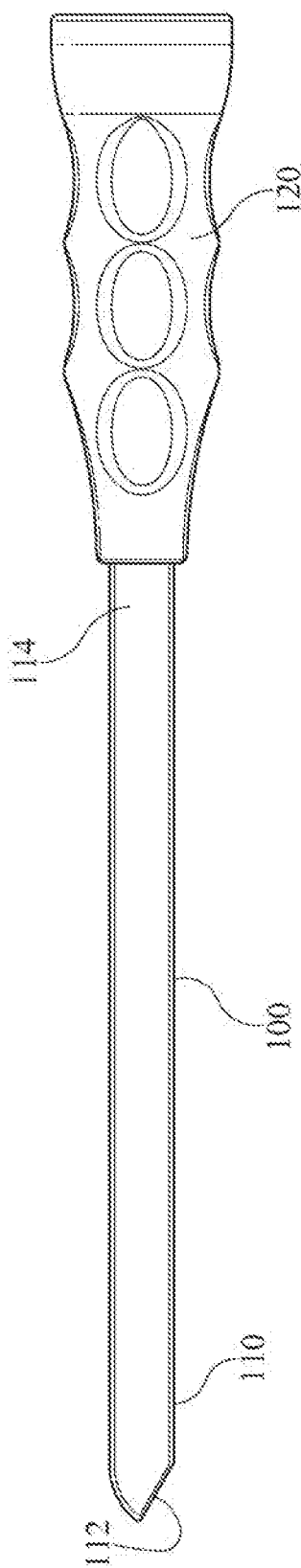
FIG. 30 is a side view of an inserter tube in accordance with one embodiment of the present invention.
Figure 31:
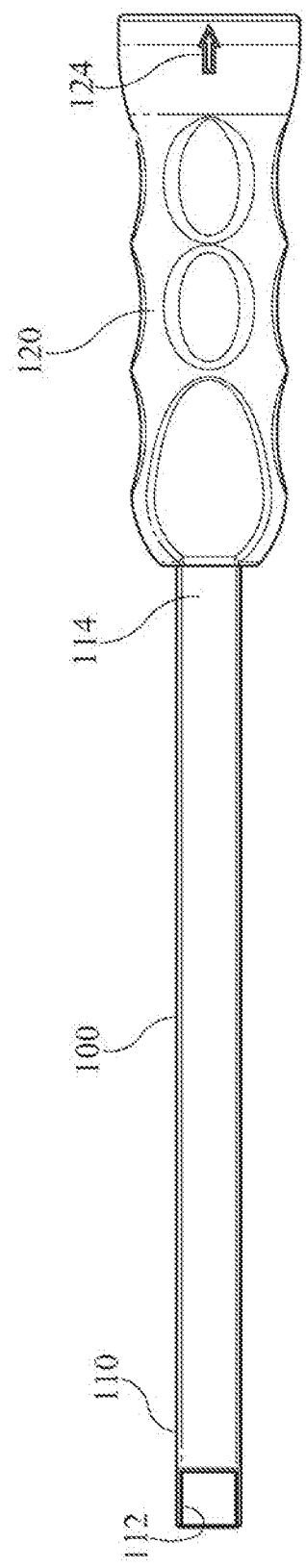
FIG. 31 is a side view of an inserter tube in accordance with one embodiment of the present invention.

FIGS. 29-31 depict one exemplary embodiment of inserter tube 100 and its engagement with handle 510. Inserter tube 100 includes a distal end 100 terminating in a curved portion 112 and a proximal end 114 terminating in a hollow handle 120 that communicates with tube 100, said handle 120 having a locking flange 122 on an interior circumference thereof that engages complementary locking flange 520 of trial handle 510. Inserter tube 100 handle 120 may also include an alignment arrow 124 that, when aligned with one of the lock/unlock markings 524, 522 of handle 510 indicate that locking flange 122 of inserter tube 100 is engaged or disengaged with locking flange 520 of handle 110. In a further embodiment of the invention, inserter tube handle 120 may comprise a small groove in a proximal edge thereof to accommodate suture 3 as it exits handle 120 when inter-body device 20 is being deployed.

FIG. 29 additionally shows bullnose 600 inserted into inserter tube 100 and extending through distal end 110 thereof. As can be seen from this drawing Figure, bullnose 600 may be secured to handle 510 thence inserted into inserter tube 100, which is then locked onto handle 510. By carefully positioning inserter tube 100 into disc space 100, bullnose 600 may then be inserted to an exact depth into disc space 2 necessary for suitable placement of inter-body device 2. Accordingly, inserter tube 100 may be provided with a plurality of depth markings along the exterior surfaces thereof (for example on upper and lower walls 102, 104 and on medial and lateral walls 106, 108) to assist a surgeon in proper placement of inserter tube 100, as will be discussed in further detail herein below.

FIGS. 38-43 depict the deployment of trial implant 400 through inserter tube 100 into disc space 2. Firstly, inserter tube 100 and concomitant bullnose 600 are inserted into disc space 2 through an annulotomy as far laterally in the disc space as possible. This first step is typically practiced with bullnose 600 having a tapered tip 610 to aid in disc space distraction. In one embodiment of the present invention, the tapered tip 610 extends approximately 15 mm past beyond the distal end 110 curved tip 112 of inserter tube 100. A surgeon may note the depth of the inserter tube in the annulotomy at this stage of the procedure.

Secondly, a blunt tip 610 bullnose is assembled to trail handle 510 and inserter tube 100 and reinserted in disc space 2 In one embodiment of the present invention, the blunt tip 610 extends approximately 10 mm past beyond the distal end 110 curved tip 112 of inserter tube 100. The blunt tip 610 and concomitant inserter tube 100 are advanced into disc space 2 until distal tip 610 of bullnose 600 touches the anterior annulus 5 of disc space 2. At this point, bullnose 600 may be withdrawn and inserter tube 100 locked into place, as will be discussed further herein below.

A trial implant 400 is now secured to trial handle 510 and is advanced into disc space 2, as shown sequentially in FIGS. 38-43. The ability of trial implant 400 to articulate coupled with the curved portion 112 of inserter tube 100 enable accurate and easy placement of trial implant 400 in disc space 2. Furthermore, differing lengths and heights of trial implants 400 may be employed to determine the proper size inter-body device 20 to be used. The longest trial implant 400 that can be successfully deployed in disc space 2 will determine the length of inter-body device 20 to be used. Typically, the height of a distractor used to distract the disc space will determine the height of the inter-body device 20 to be deployed.

Figure 47:
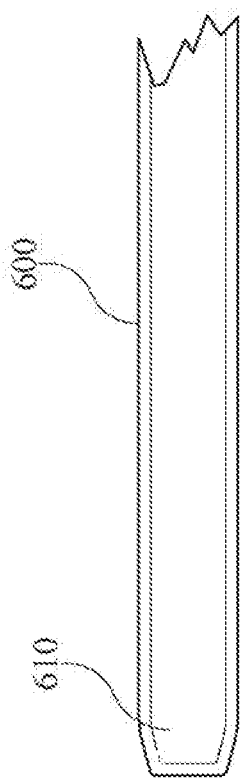
FIG. 47 is a partial bottom view of a bullnose in accordance with one embodiment of the present invention.
Figure 46:
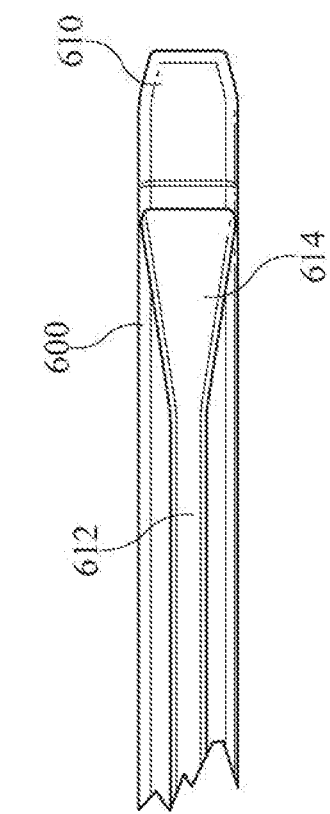
FIG. 46 is a partial top view of a bullnose in accordance with one embodiment of the present invention.

Referring now to FIGS. 44, 46 and 47, an exemplary deployment of inter-body device 20 through inserter tube 100 utilizing suture 3 to secure device 20. In this embodiment of the invention, bullnose 600 comprises a single longitudinal suture guide groove 612 and wide groove end on one side of bullnose 600. FIG. 44 depicts distal tip 610 advancing device 20 through inserter tube 100 until it is properly positioned in disc space 2.

Figure 49:
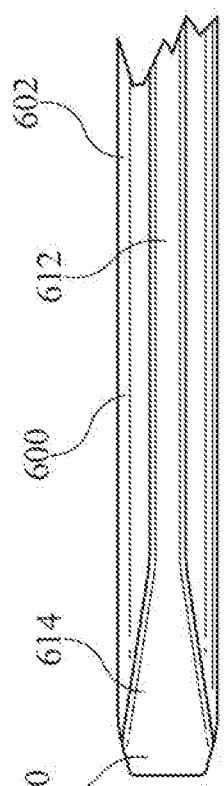
FIG. 49 is a partial bottom view of a bullnose in accordance with one embodiment of the present invention.
Figure 48:
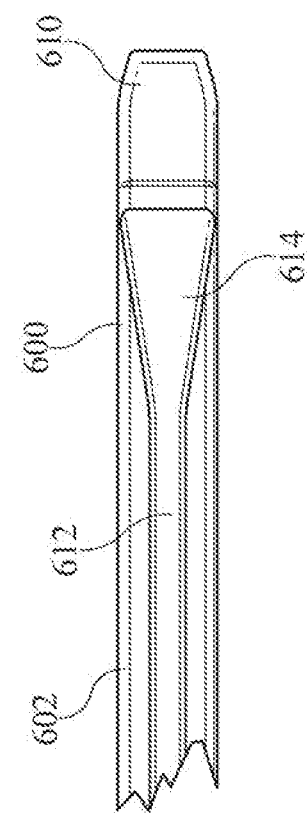
FIG. 48 is a partial top view of a bullnose in accordance with one embodiment of the present invention.

In contradistinction, FIGS. 45, 48 and 49 depict a bullnose 600 having a longitudinal suture guide groove 612 and wide groove end on two sides of bullnose 600, whereby suture 3 is routed both above and below bullnose 600 shaft 602, as best seen in FIG. 45. This embodiment of the invention facilitates manipulation and placement of inter-body device 20 in disc space 2.

Figure 51:
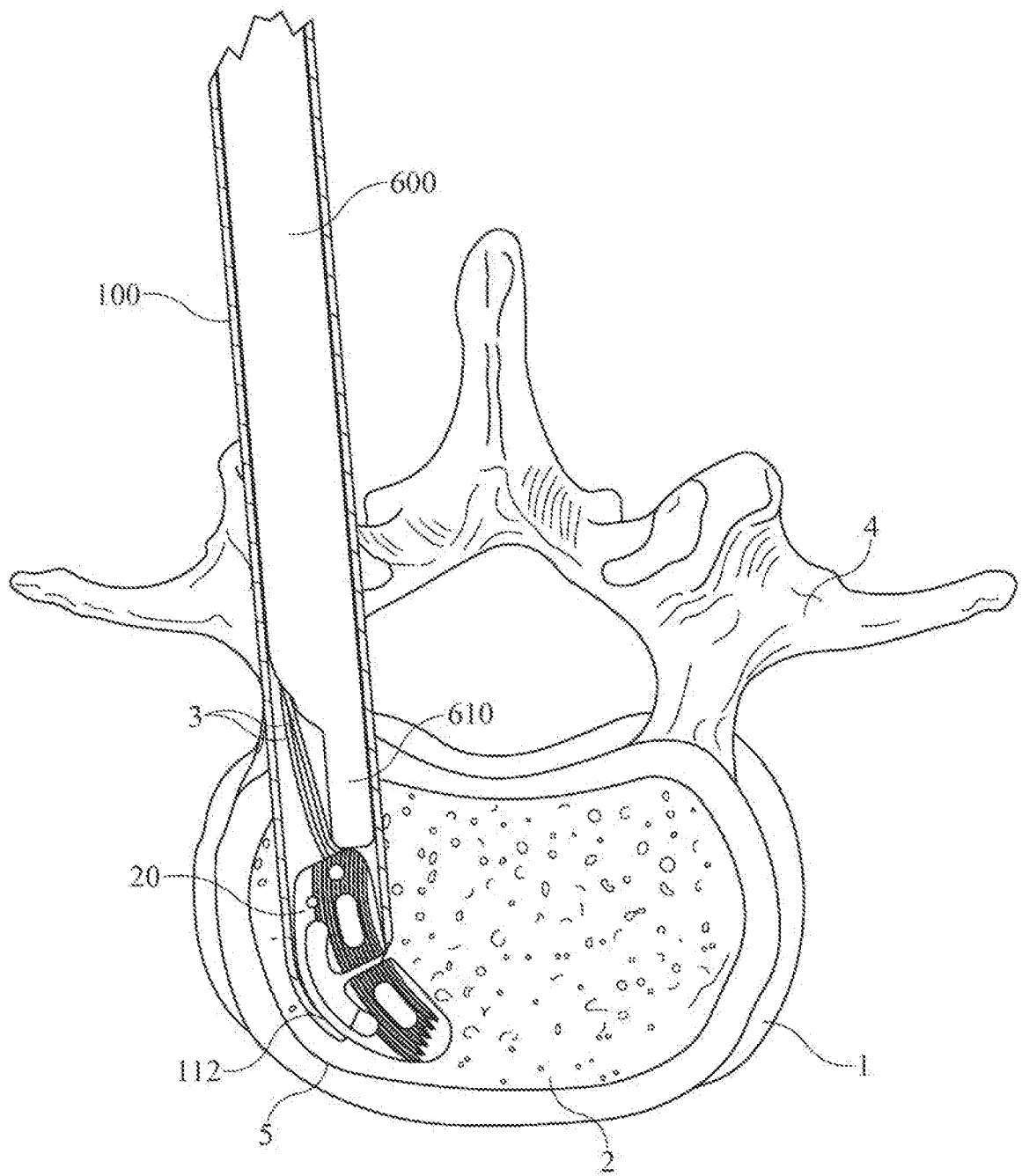
FIG. 51 is a top view of an inserter tube in a disc space, with an inter-body device and bullnose advancing into said disc space in accordance with one embodiment of the present invention.
Figure 52:
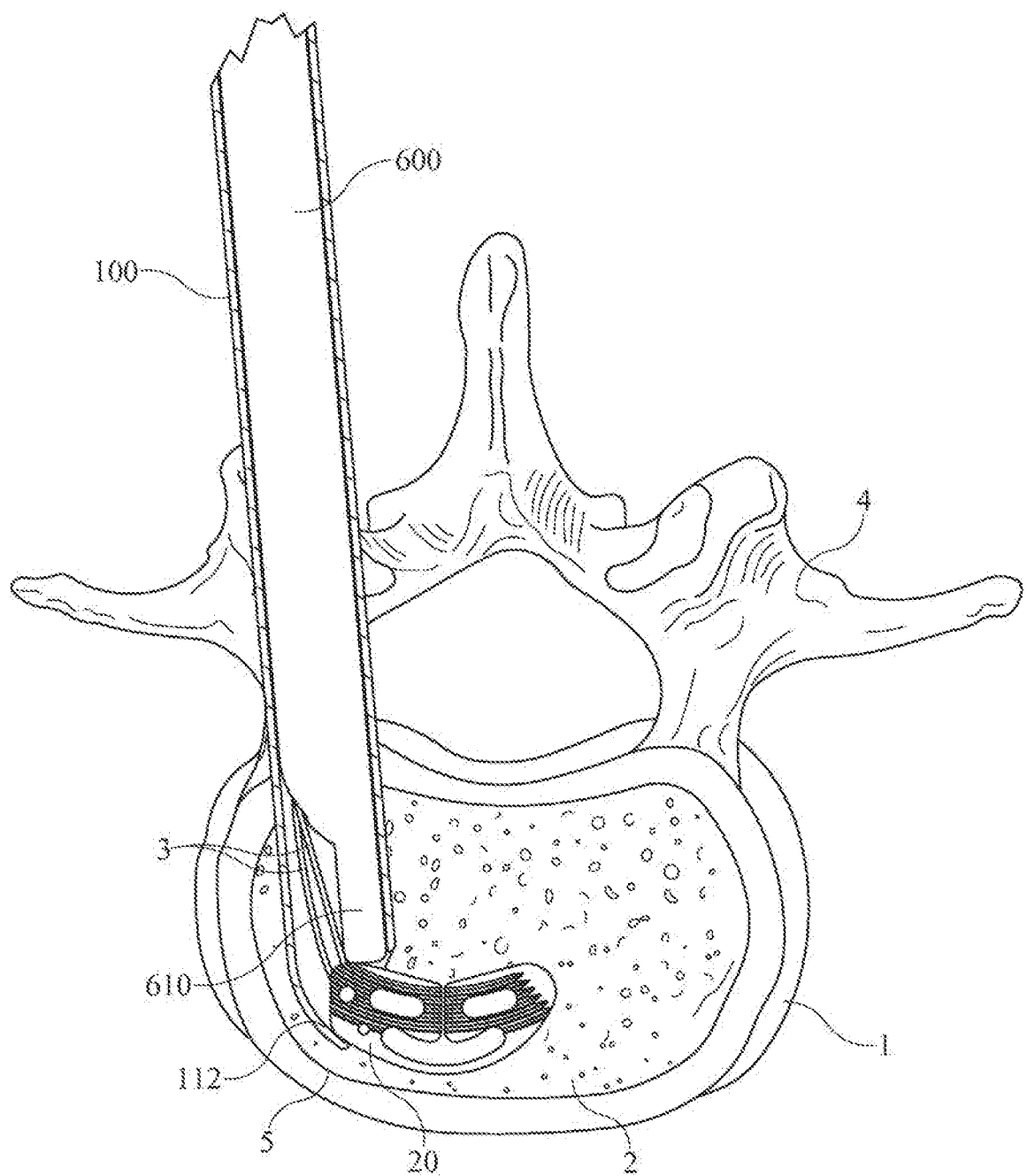
FIG. 52 is a top view of an inserter tube in a disc space, with an inter-body device and bullnose advancing into said disc space in accordance with one embodiment of the present invention.

Referring now to FIGS. 50-52, there is depicted the deployment of inter-body device 2 through inserter tube 100 into disc space 2. Apertures 46 of cans 30 may be filled with morselized bone graft material prior to inserting inter-body device 20 into inserter tube 100. A suture 3 is secured to hitch 50 of device 20 prior to insertion in inserter tube 100 as well. The suture guide groove 612 of bullnose 600 may also be aligned with the groove in inserter tube handle 120 to provide clearance for suture 3. The looped suture 3 shown in FIGS. 50-52 is disposed in groove 612 and bullnose 600 is then inserted into inserter tube 100, pushing inter-body device 20 into place as it advances into tube. It should be noted that blunt distal tip 610 bullnose 600 is used for insertion of inter-body device 20. Once properly positioned, radiographical techniques may be used to verify the positioning of inter-body device 20, whereupon suture 3 is removed, as is bullnose 600 and concomitant handle 510. Inserter tube 100 may remain in place in disc space 2 for application of bone graft material as described below.

Figure 53:
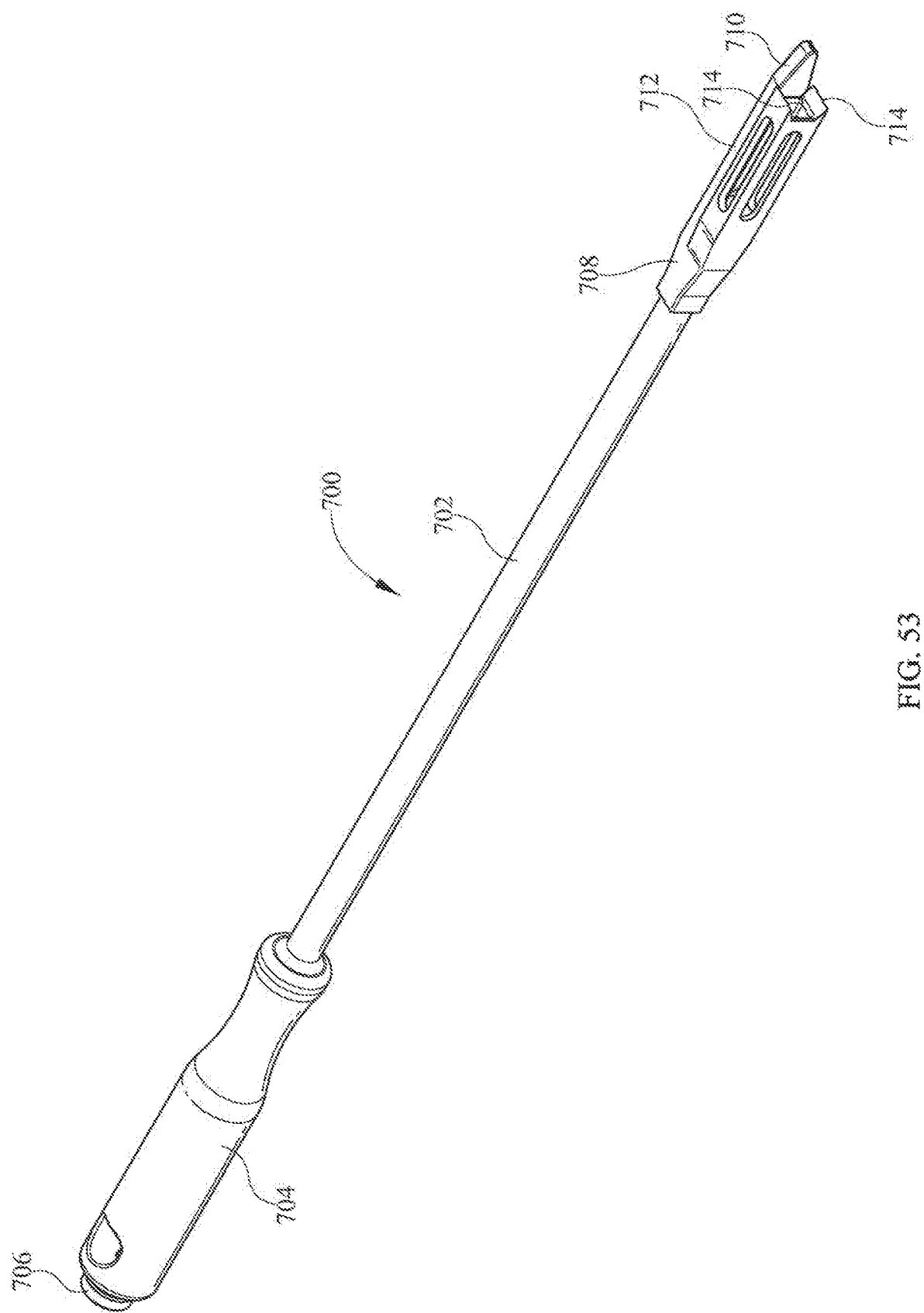
FIG. 53 is a perspective view of a box cutter in accordance with one embodiment of the present invention.
Figure 54:
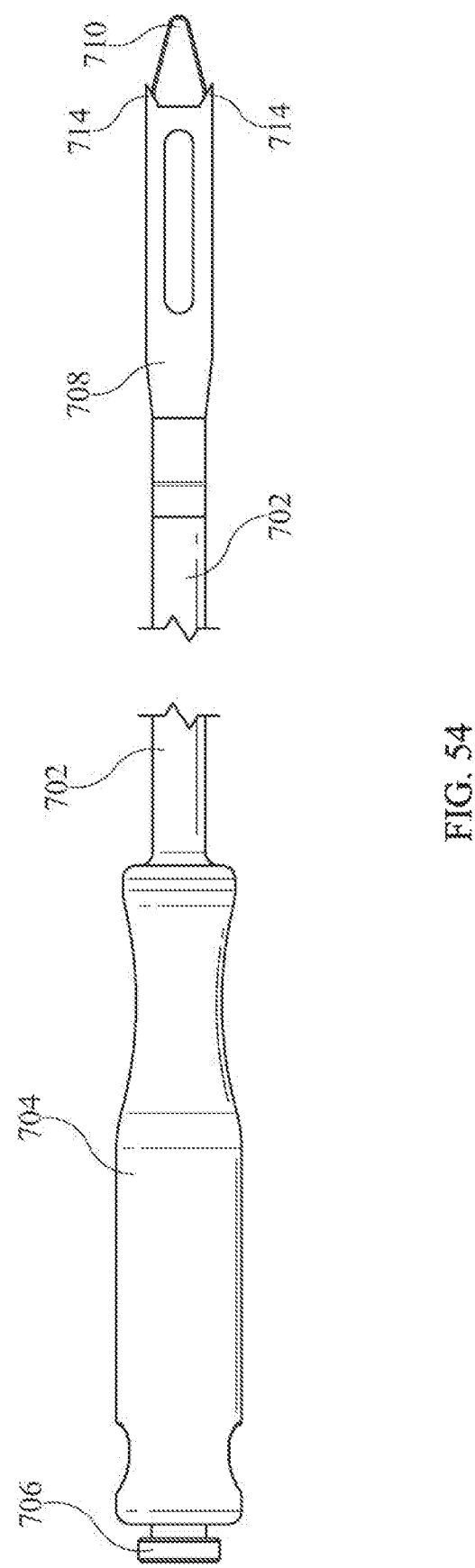
FIG. 54 is a side view of a box cutter in accordance with one embodiment of the present invention.

FIGS. 53 and 54 depict a box cutter 300 used to shave posterior endplates of adjacent vertebrae 4 in preparation for inter-body device 20 deployment. Box cutter 700 comprises a central shaft 702 secured to a handle 704 at a proximal end thereof. Handle 704 may have an option slap hammer flange 706 at a proximal end thereof for attaching a known-in-the art slap-hammer device to aid in use of box cutter 700. A detachable head 708 is secured to shaft 702 at a distal end thereof, having a tapered distal tip 710 to facilitate distraction as head 708 enters the disc space 2. Head 708 may be provided in varying widths and heights to accommodate variable spinal geometry, and further may be provided with depth markers (not shown) along the exterior surfaces thereof to enable a surgeon to determine how far distal tip 710 advances into disc space 2. In one embodiment of the present invention box cutter head 708 height may be provided by a marking on the surface thereof. Additionally, box cutter head 708 may include exterior markings indicating the distance from distal tip 710.

Box cutter 700 further comprises a pair of spaced cutting edges 714 that facilitate the shaving of the posterior endplates with box cutter 700. In operation, box cutter 700 head 708 is selected having an appropriate width for a given application, and the posterior endplates of adjacent vertebrae 4 are shaved by advancing cutting edges 714 into disc space 2, utilizing a slap-hammer attachment if necessary.

Figure 56:
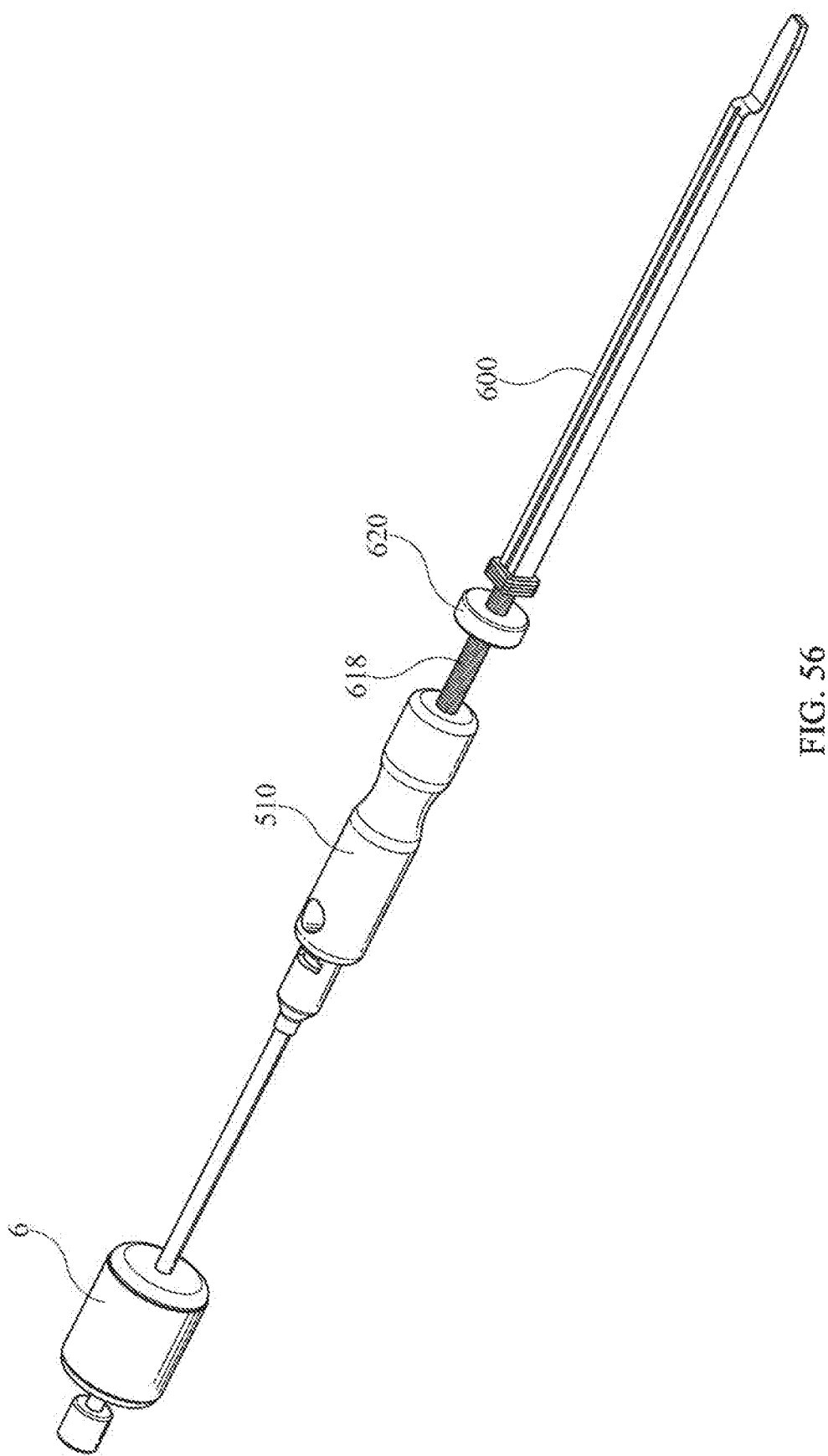
FIG. 56 is a perspective view of a trial handle and a bullnose in accordance with one embodiment of the present invention.

FIGS. 55-58 depict an alternative embodiment of the inserter tube 100 of the instant invention wherein the proximal end 114 is slightly wider than distal end 110 and wherein no handle is present. FIG. 56 depicts an alternative embodiment of bullnose 600 having a proximal end 604 that includes a threaded shaft 618 for engaging a handle 510, as well as a threaded stop 620 that is rotatable along threaded shaft 618 that abuts distal end 114 of inserter tube 100 when bullnose 600 is inserted therein. FIG. 56 further depicts a conventional "slap-hammer" 6 device secured to handle 510 to apply additional longitudinal force to bullnose 600 where necessary.

Figure 57:
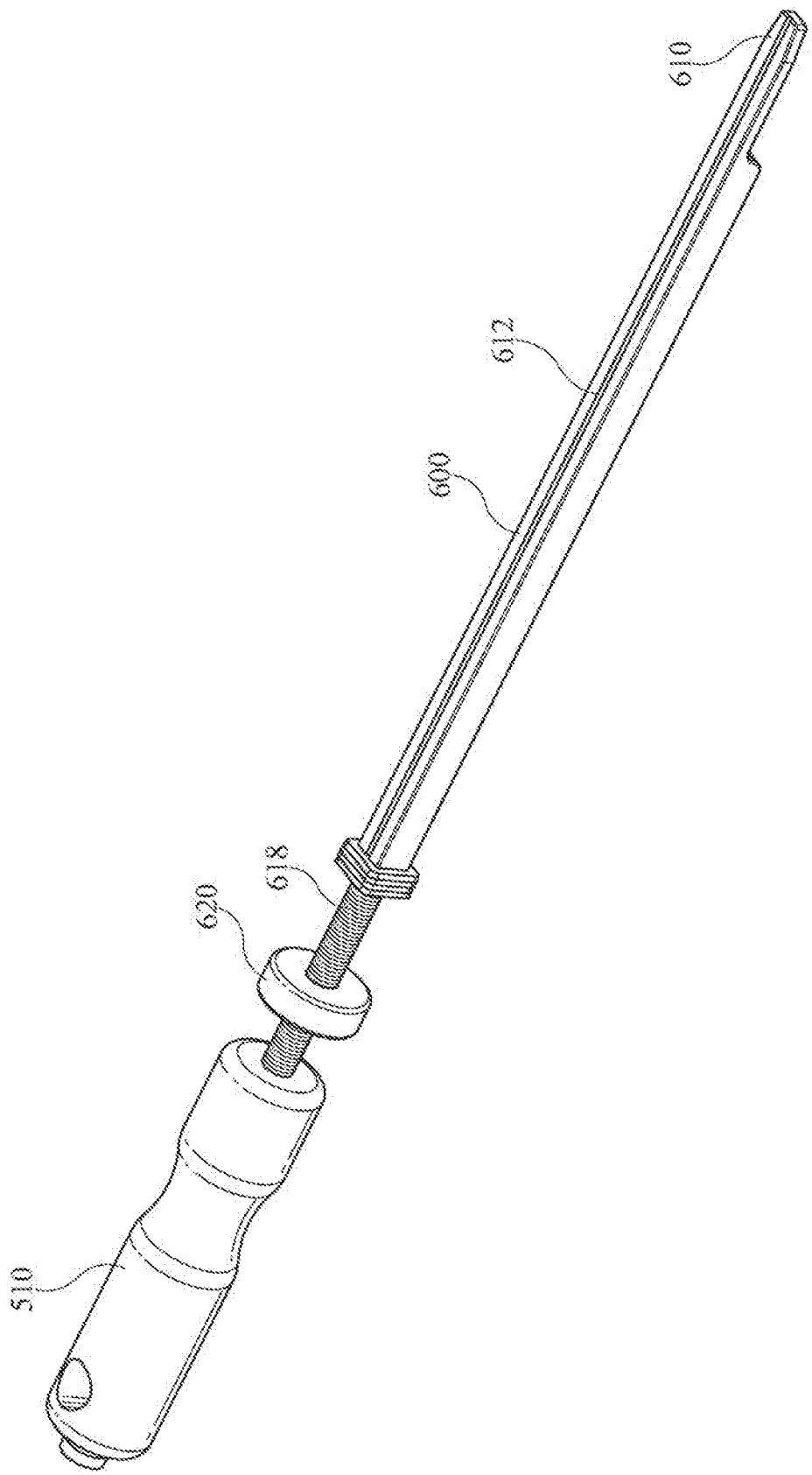
FIG. 57 is a perspective view of a trial handle and a bullnose in accordance with one embodiment of the present invention.
Figure 58:
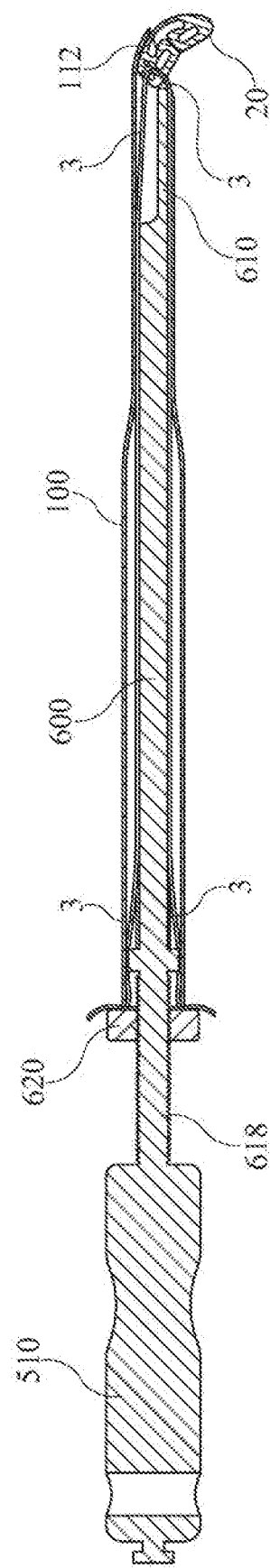
FIG. 58 is a cross-sectional side view of a bullnose and inter-body device being advanced through an inserter tube in accordance with one embodiment of the present invention.

FIG. 57 is a view of bullnose 600 from the opposite side as FIG. 56, depicting a second suture guide groove 612 extending longitudinally into distal tip 610 of bullnose 600 for positive placement of suture 3. FIG. 58 is a cross-sectional view of bullnose 600 deploying inter-body device 20 through inserter tube 100, wherein suture 3 is guided in grooves 112 both above and below bullnose 600, as suture 3 loops through hitch 50 of inter-body device 20. This feature of the invention further aids in positioning of implants as they are deployed into disc space 20.

Figure 59:
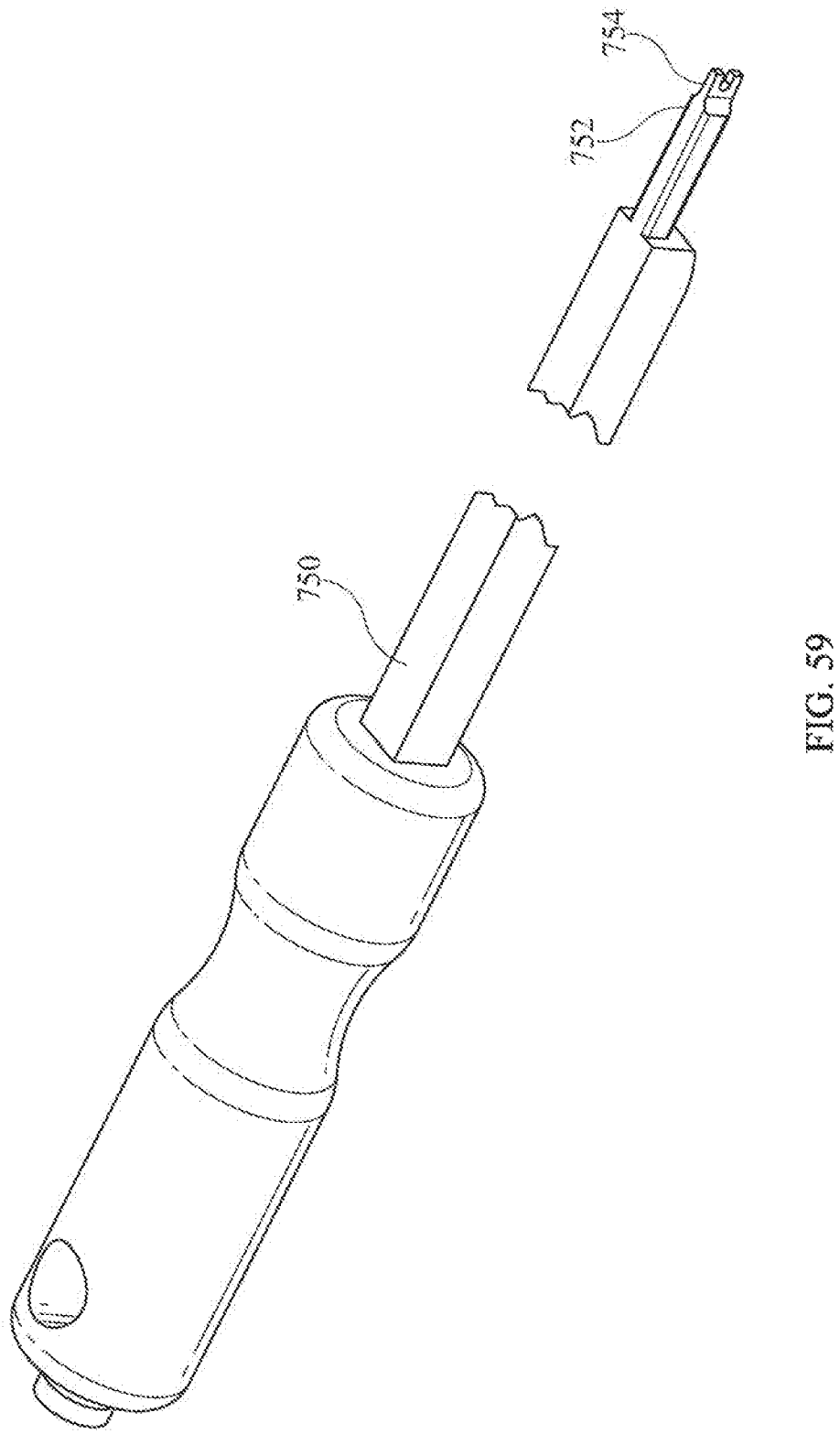
FIG. 59 is a perspective view of an inter-body device insertion tool in accordance with one embodiment of the present invention.
Figure 60:
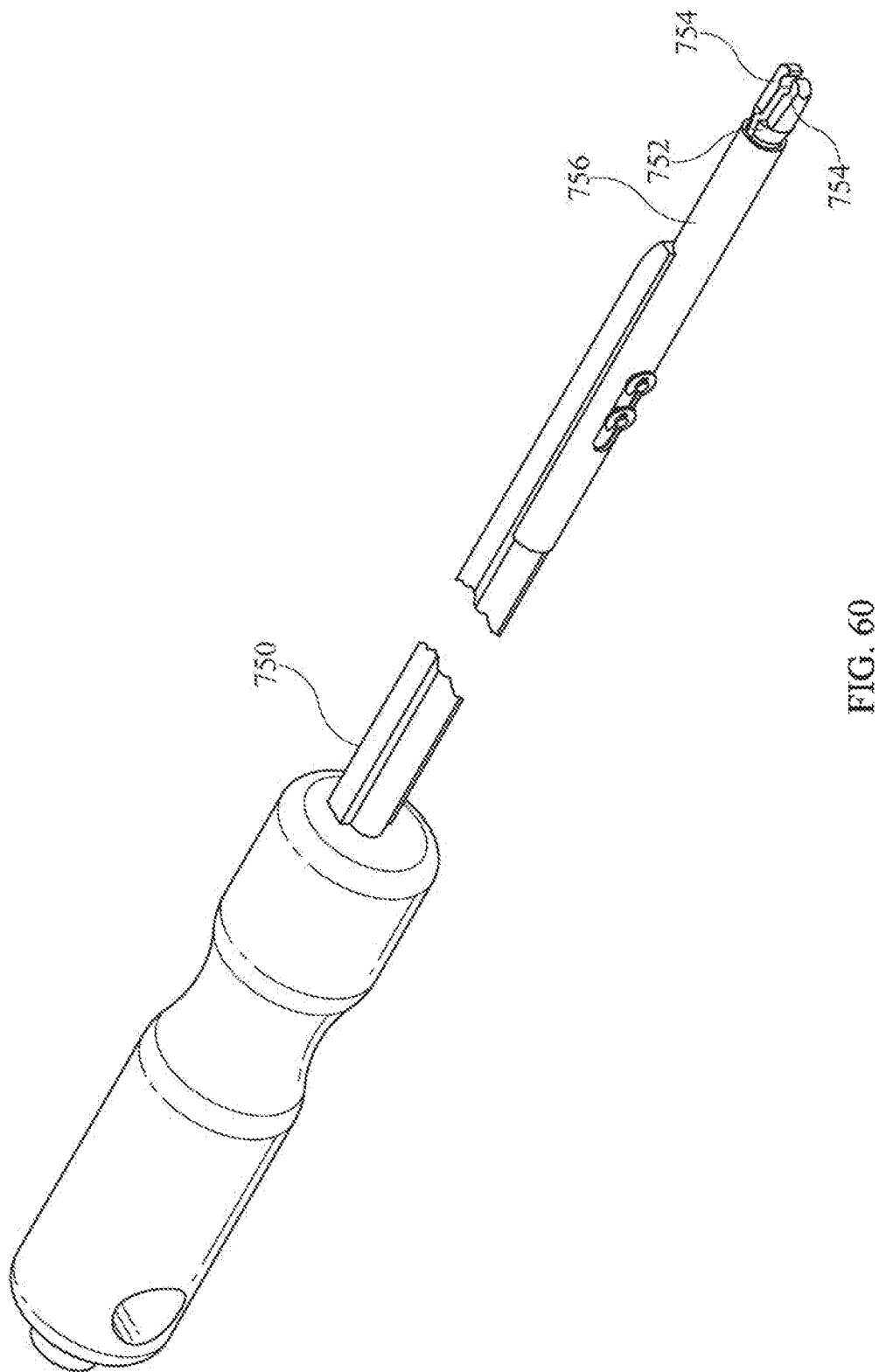
FIG. 60 is a perspective view of an inter-body device insertion tool in accordance with one embodiment of the present invention.

FIGS. 59 and 60 depict two inter-body device 20 insertion and retrieval tools 750, each having a distal end 752 having a pair of spaced furcations 754 extending therefrom to engage pin 59 of inter-body device 20, or a similar hitch 50. In the embodiment of FIG. 59, furcations 754 are spaced to snap-fit onto pin 59 of hitch 50. In the retrieval tool embodiment shown in FIG. 60, a longitudinally slidable sleeve 756 is provided over distal end 752 of tool 750 that forces furcations 754 together to grasp pin 59 as sleeve 756 is advanced toward distal end 752.

Figure 61:
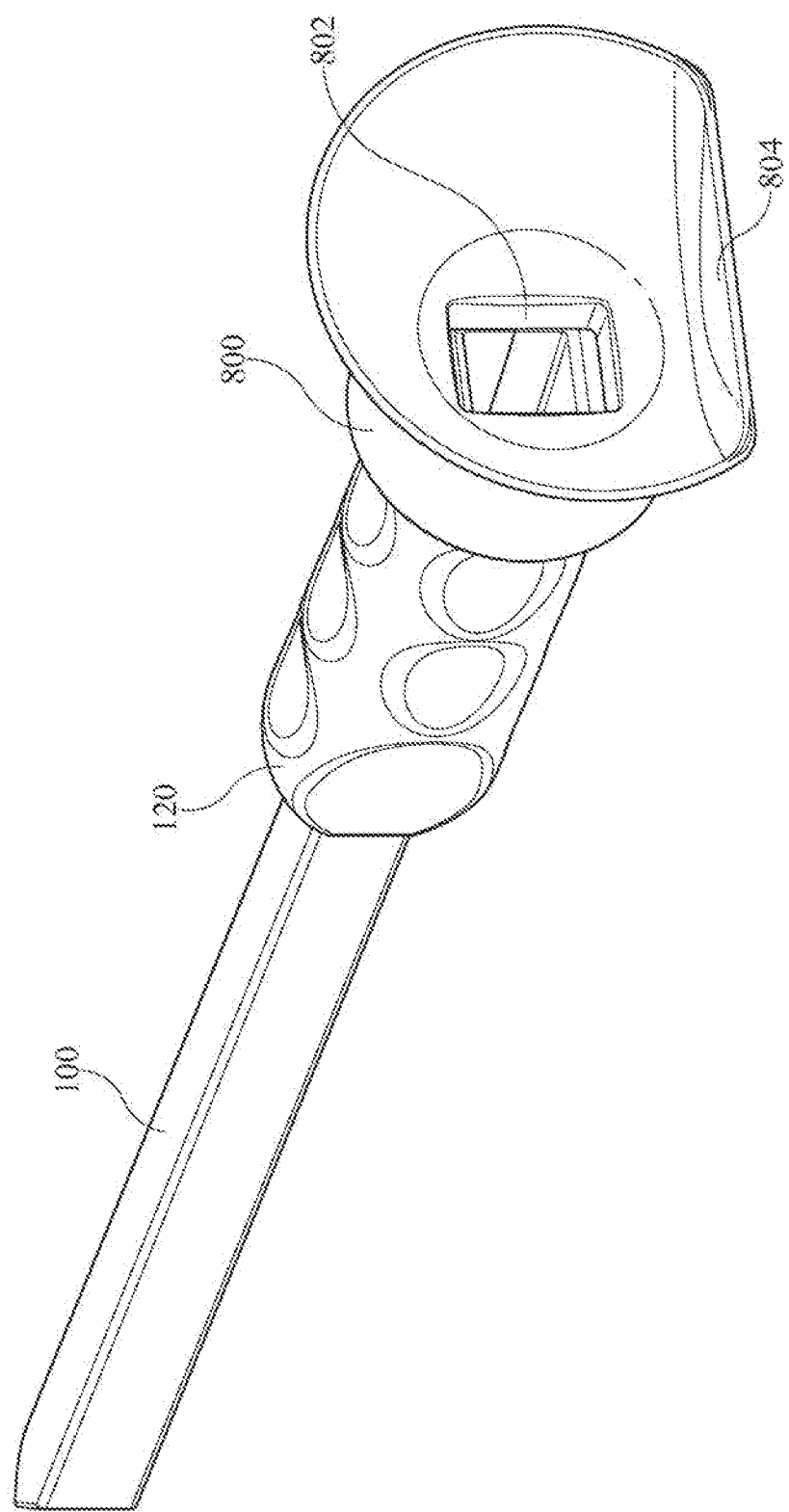
FIG. 61 is a perspective view of a bone graft funnel secured to an inserter tube in accordance with one embodiment of the present invention.
Figure 62:
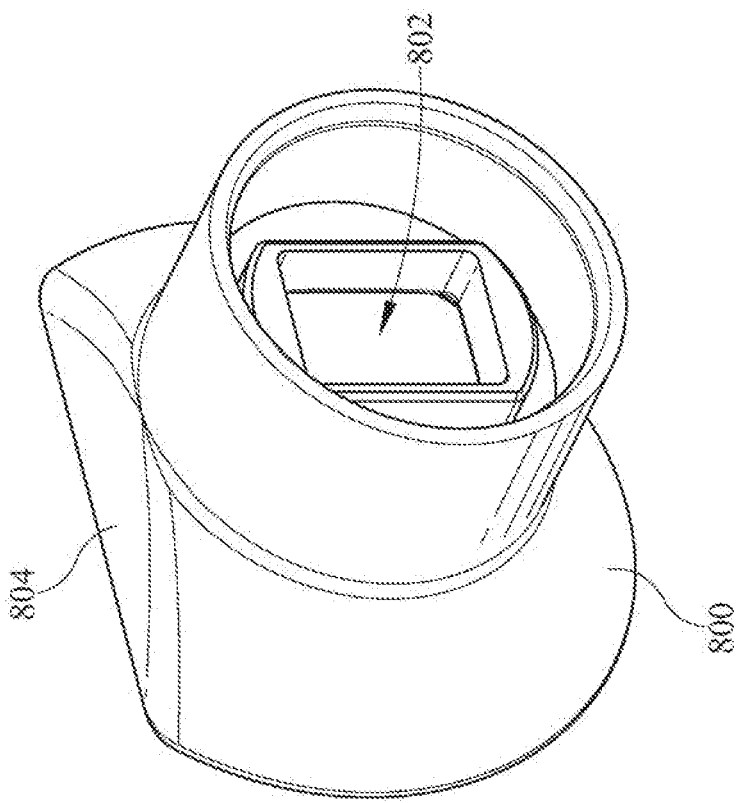
FIG. 62 is a perspective view of a bone graft funnel in accordance with one embodiment of the present invention.
Figure 63:
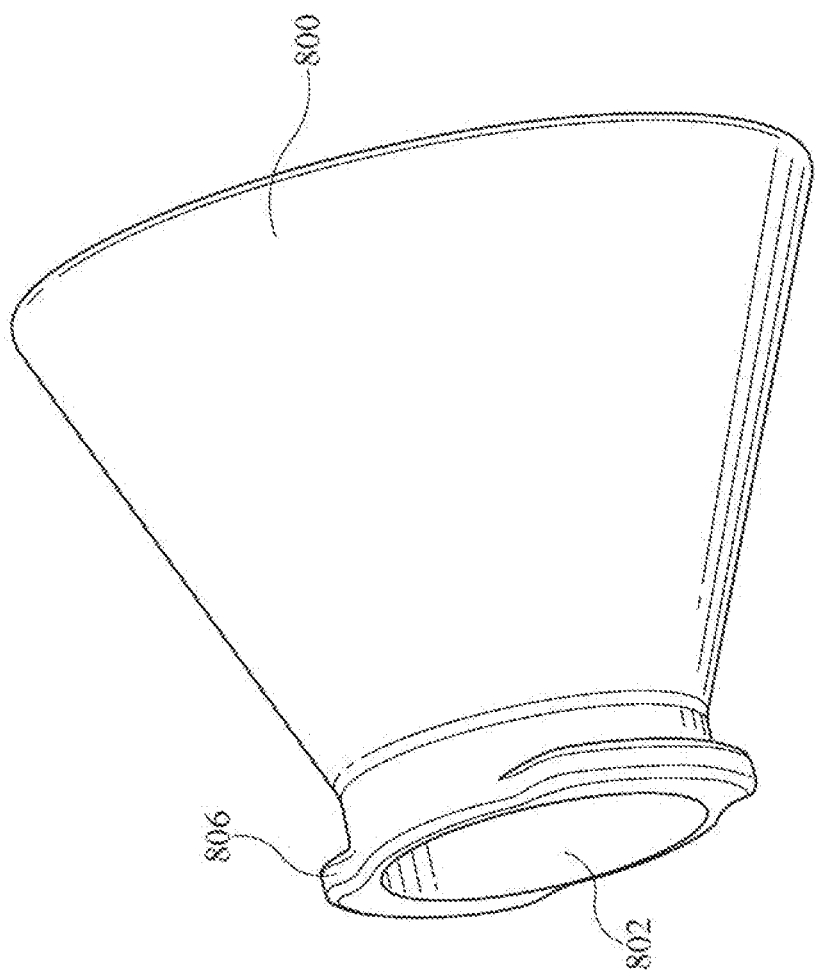
FIG. 63 is a perspective view of a bone graft funnel in accordance with one embodiment of the present invention.

FIGS. 61 and 62 depict a bone graft funnel 800 that is operatively secured to inserter tube 100 handle 100 having an aperture 802 therein for supplying bone graft material through inserter tube 100 to disc space 2, as well as a flat edge 804 for ease of use, thereby facilitating use of bone graft funnel with other instruments or structures employed in spinal surgery. As best seen in FIG. 63, and in an alternative embodiment of bone graft funnel 800, a locking flange 806 is provided on one edge thereof for engaging a complementary flange on inserter tube 100 handle 120.

Figure 64:
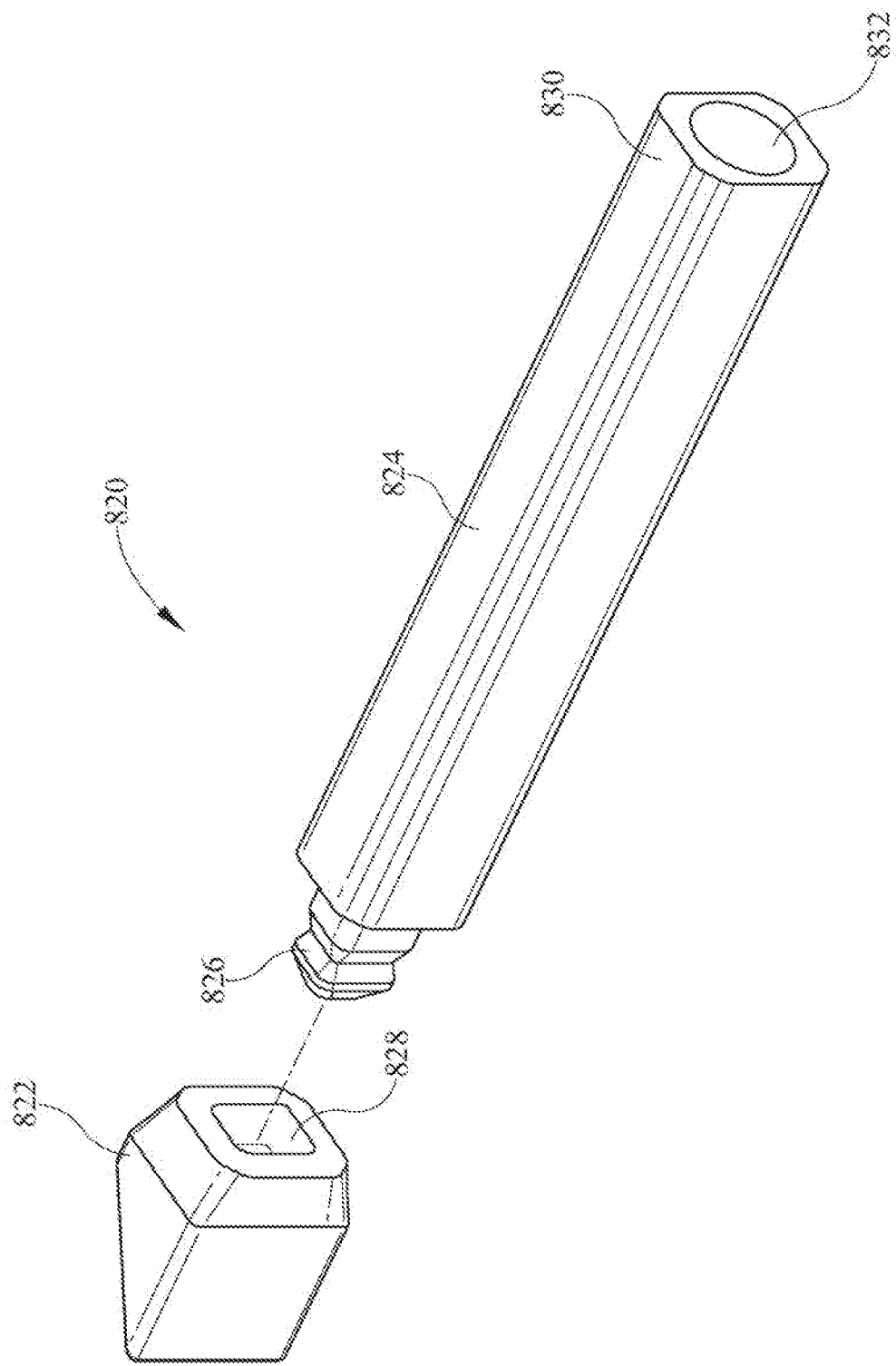
FIG. 64 is an exploded perspective view of a bone graft plunger in accordance with one embodiment of the present invention.
Figure 65:
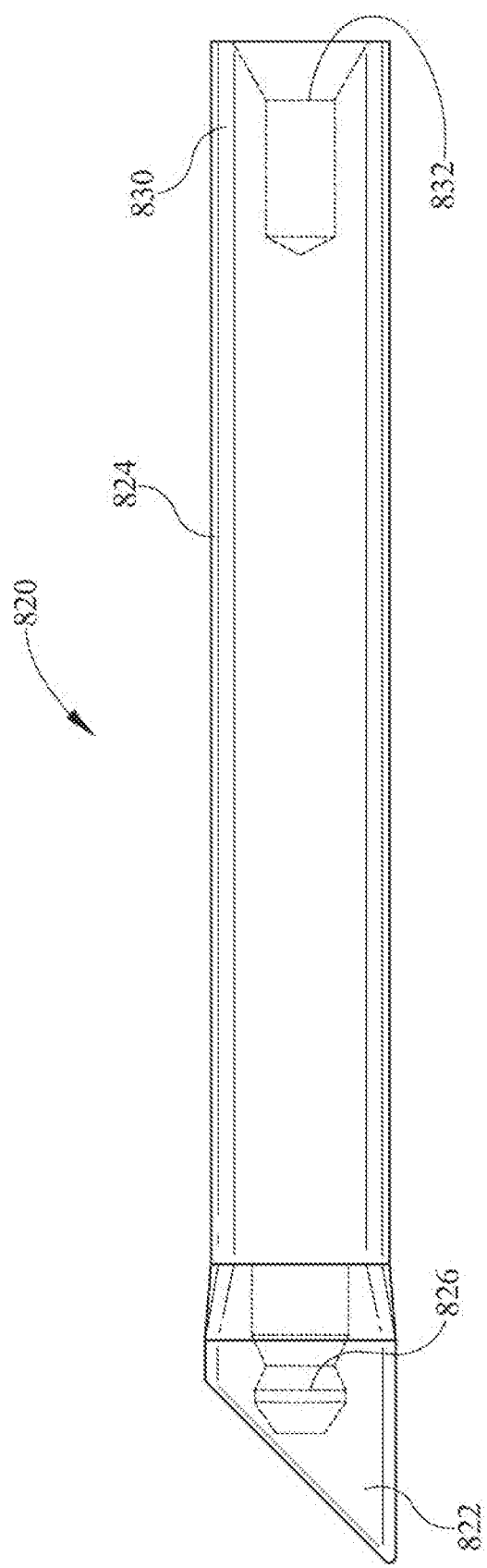
FIG. 65 is a perspective view of a bone graft plunger in accordance with one embodiment of the present invention.

FIG. 64 depicts a bone graft plunger 820 designed for use with bone graft funnel 800 and inserter tube 100, having an angled plunger tip 822 on a distal end thereof. Angled plunger tip 822 may be formed of, for example, a flexible material such as a silastic elastomer that enables plunger tip 822 to flex as it extends through inserter tube 100. In one embodiment of the present invention plunger tip 822 is disposable after each use. Furthermore, and in accordance with one embodiment of the invention, angled tip 822 is sized to be slightly larger than the interior profile of inserter tube 100 to tightly engage inserter tube 100 and enable angled tip 822 to force all the bone graft material deposited in inserter tube 100 into disc space 2. Bone graft plunger 820 further comprises a central shaft 824 having a distal end 826 that is shaped to snap-fit onto a complementary aperture 828 of angled tip 822, thereby securing tip 822 to shaft 824. A proximal end 830 of shaft 824 may include a threaded aperture 832 for securing bone graft plunger to a handle 510. While plunger tip 822 is be comprised of an elastomeric material, making it both flexible and disposable after use, plunger shaft 824 may be comprised of elastomer, but may also be produced from more durable alloys for repeated use after sterilization.

Figure 66:
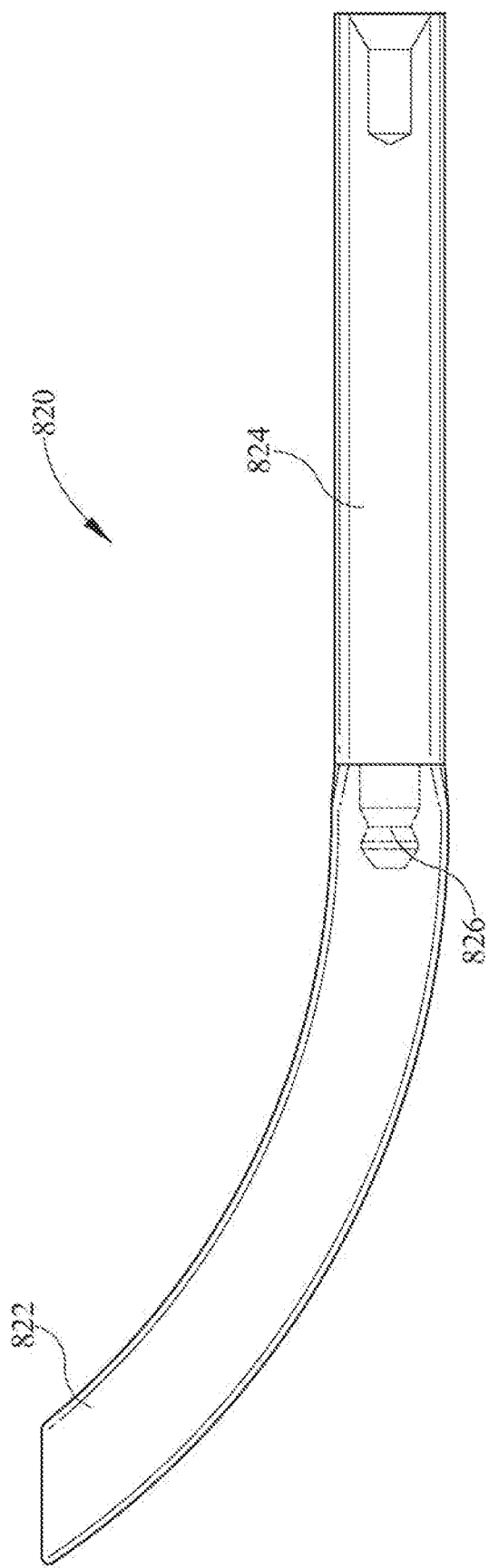
FIG. 66 is a perspective view of a bone graft plunger in accordance with one embodiment of the present invention.

FIG. 66 depicts an alternative embodiment of bone graft plunger 820 that includes an elongated angled flexible tip 822 (shown in its relaxed state) that is secured to a plunger shaft 824. This embodiment of the invention enables bone graft material to be deposited further into disc space 2 since plunger 820 assumes a relaxed shape that approximates that of anterior disc space 2.

Figure 67:
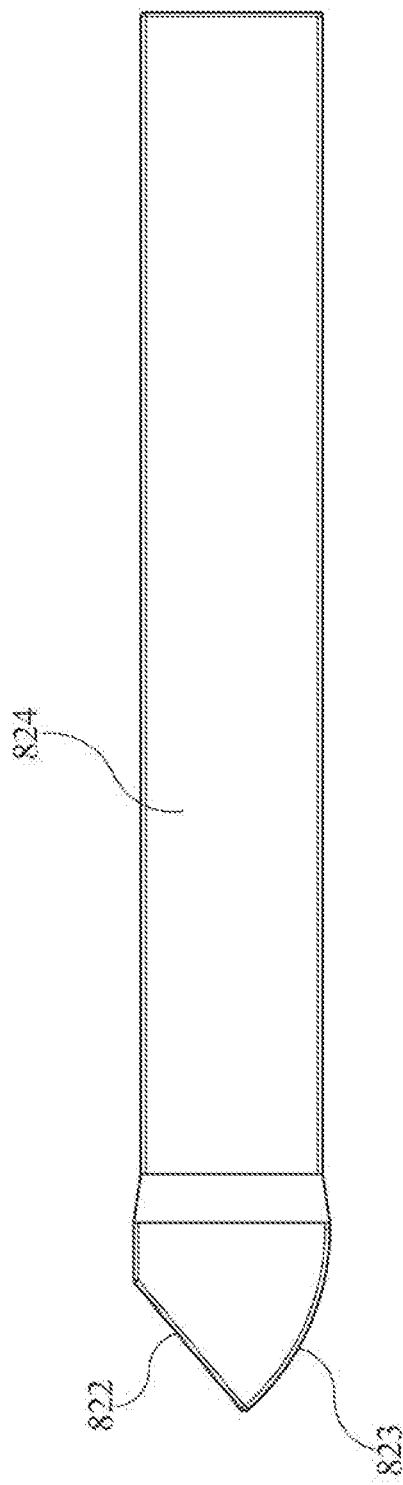
FIG. 67 is a side view of a bone graft plunger in accordance with one embodiment of the present invention.
Figure 68:
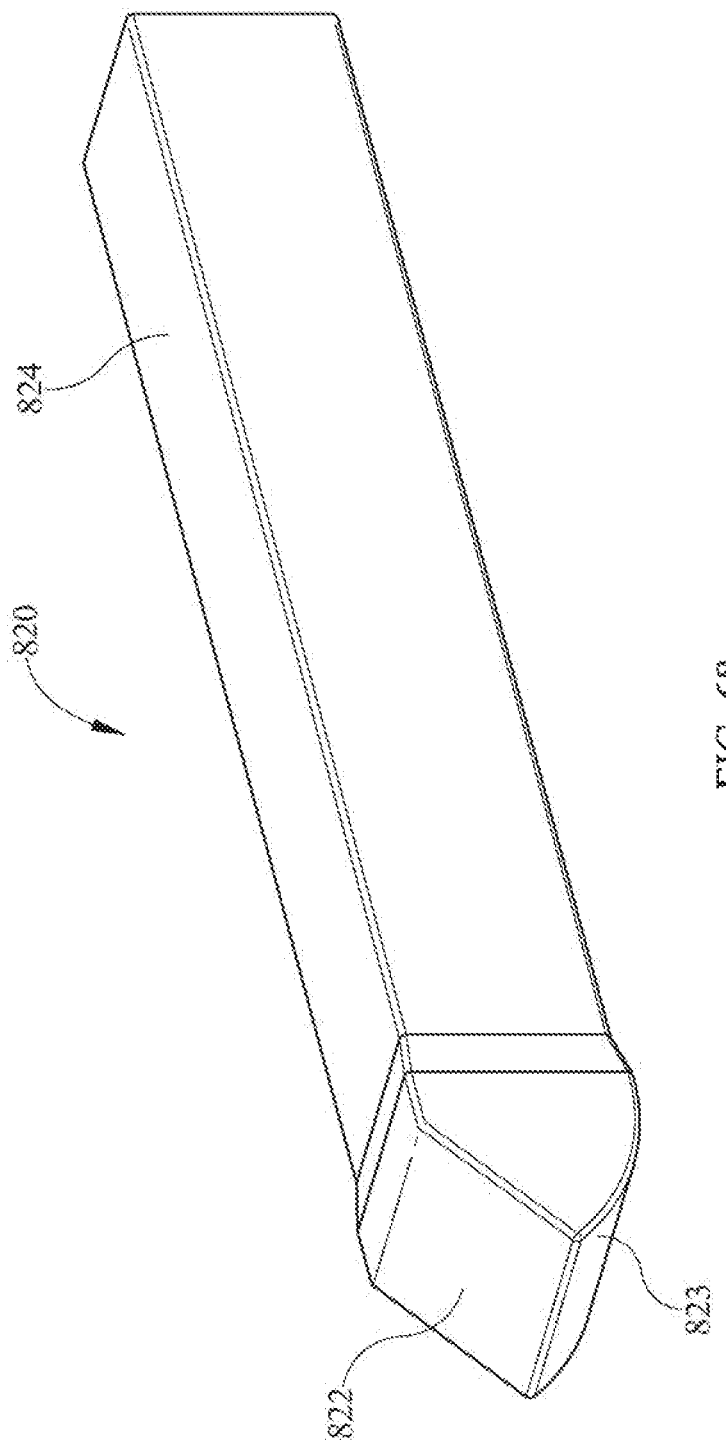
FIG. 68 is a perspective view of a bone graft plunger in accordance with one embodiment of the present invention.

FIGS. 67 and 68 show an alternative bone graft plunger 820 that is a single-piece plunger having an integral angled tip 822 and plunger shaft 824. Bone graft plunger 820 angled tip 822 may include a curved surface 823 designed to push bone graft material through complementary curved portion 112 of inserter tube 100. Plungers 820 constructed in accordance with this embodiment of the present invention can be manufactured of an elastomer or metal alloy without departing from the scope of the present invention.

Figure 69:
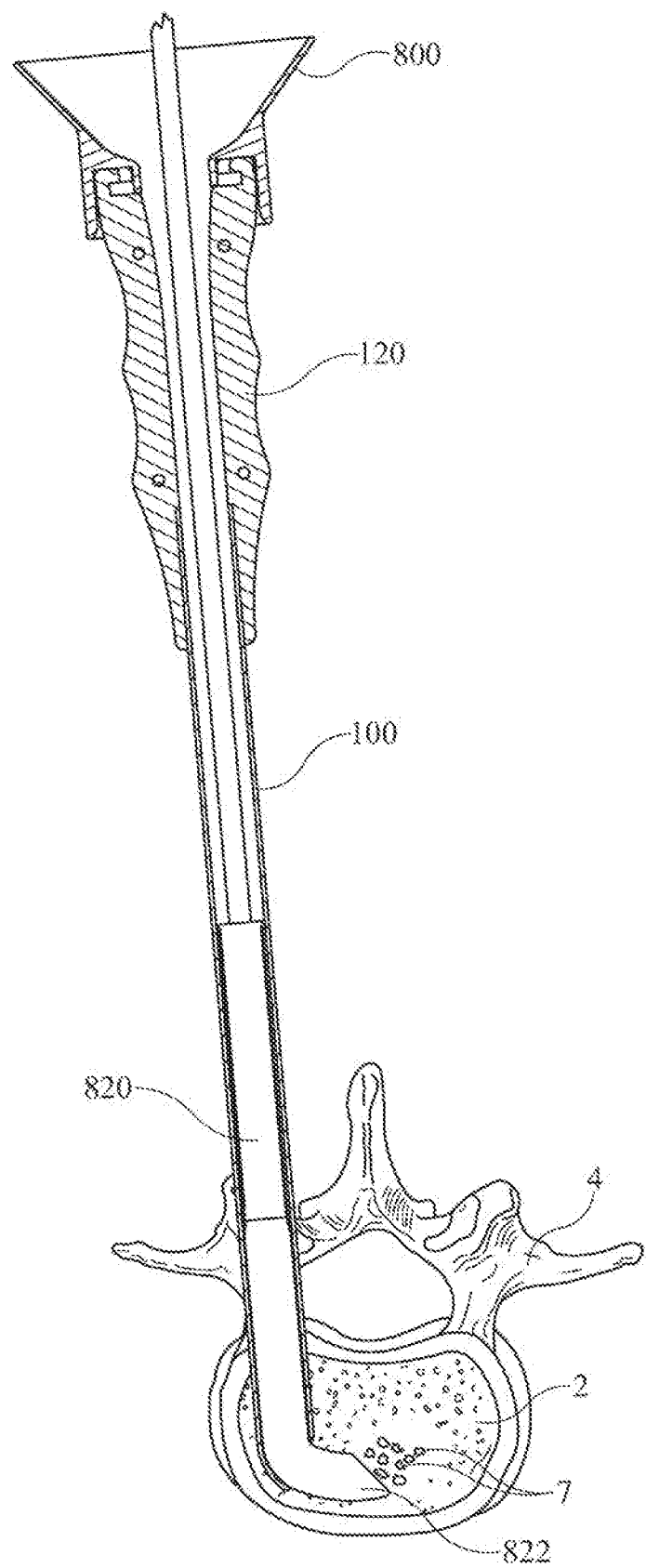
FIG. 69 is a cross-sectional side view of a bone graft plunger being advanced through an inserter tube into a disc space in accordance with one embodiment of the present invention.

FIG. 69 is a cross-section of bone graft funnel 800, plunger 820, and inserter tube 100 in operation. Funnel 800 is secured to inserter tube 100 handle 120 and provides a convenient mechanism for depositing bone graft material 7 into inserter tube 100. Plunger 820 is then inserted into aperture 802, and through handle 120 into inserter tube 100, thereby forcing all bone graft material 7 deposited therein into inserter tube 100 and disc space 2. Funnel 800 is then removed from handle 120 and plunger 820 is once again used to force the remaining bone graft material in inserter tube 100 into disc space 2. Flexible angled tip 822 enables plunger 820 to curve into disc space 2 as it is advanced, thereby providing superior delivery of bone graft material 7.

Figure 70:
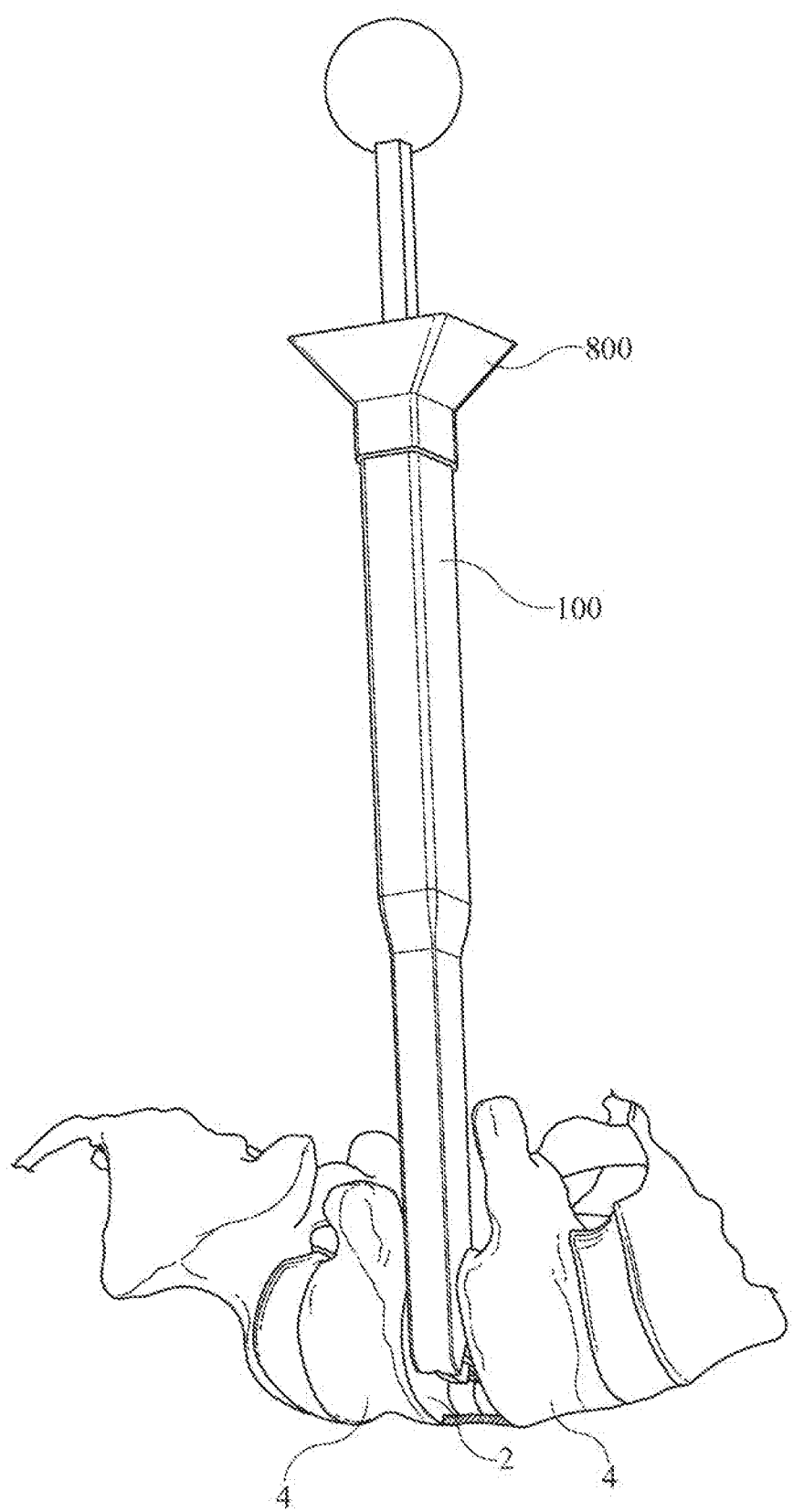
FIG. 70 is a side view of a bone graft plunger being advanced through an inserter tube into a disc space in accordance with one embodiment of the present invention.
Figure 71:
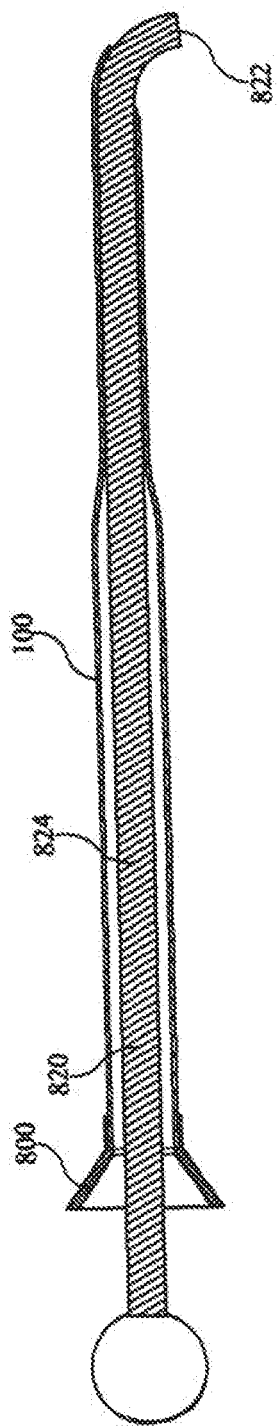
FIG. 71 is a cross-sectional side view of a bone graft plunger being advanced through an inserter tube in accordance with one embodiment of the present invention.
Figure 72:
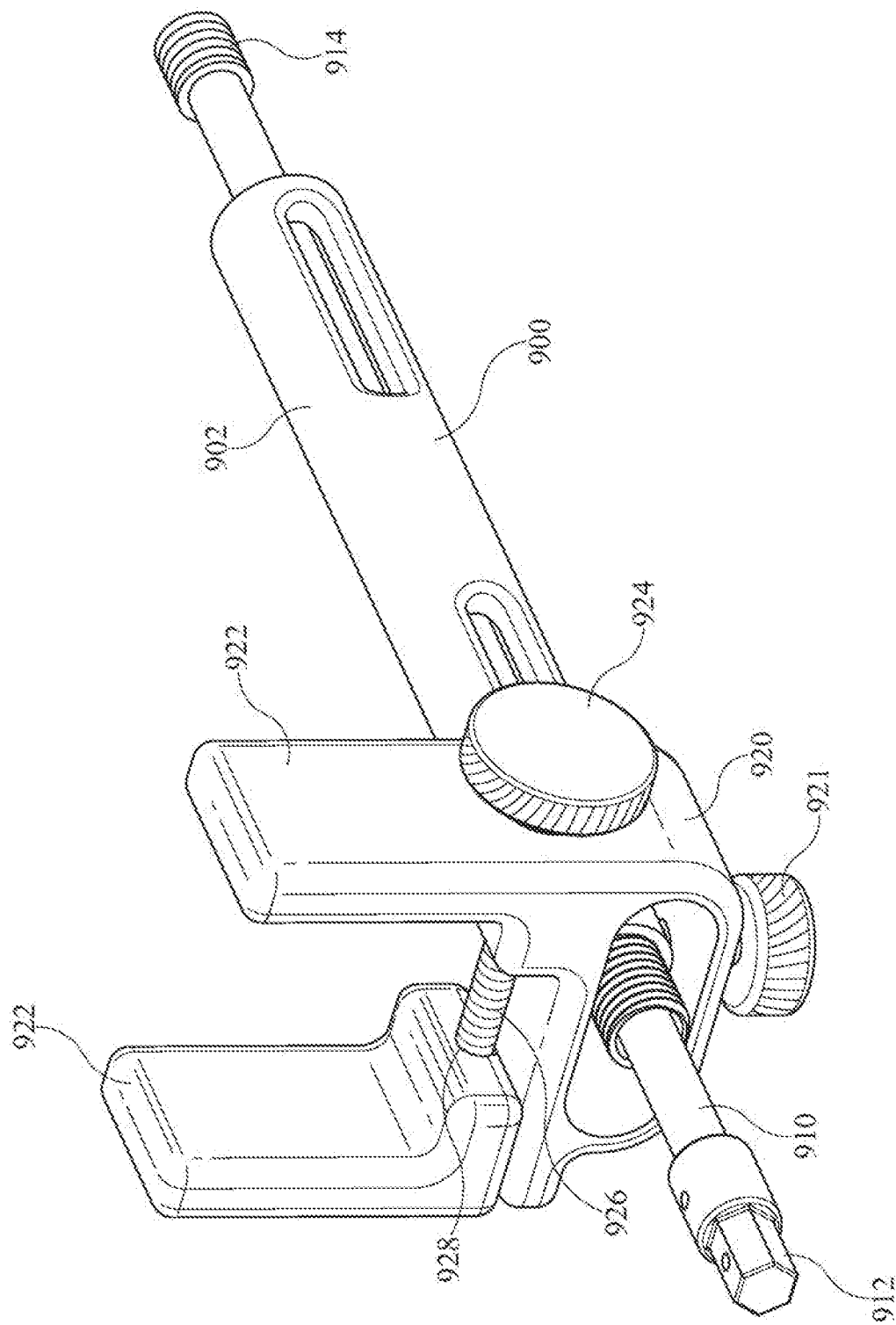
FIG. 72 is a perspective view of an extension arm in accordance with one embodiment of the present invention.
Figure 73:
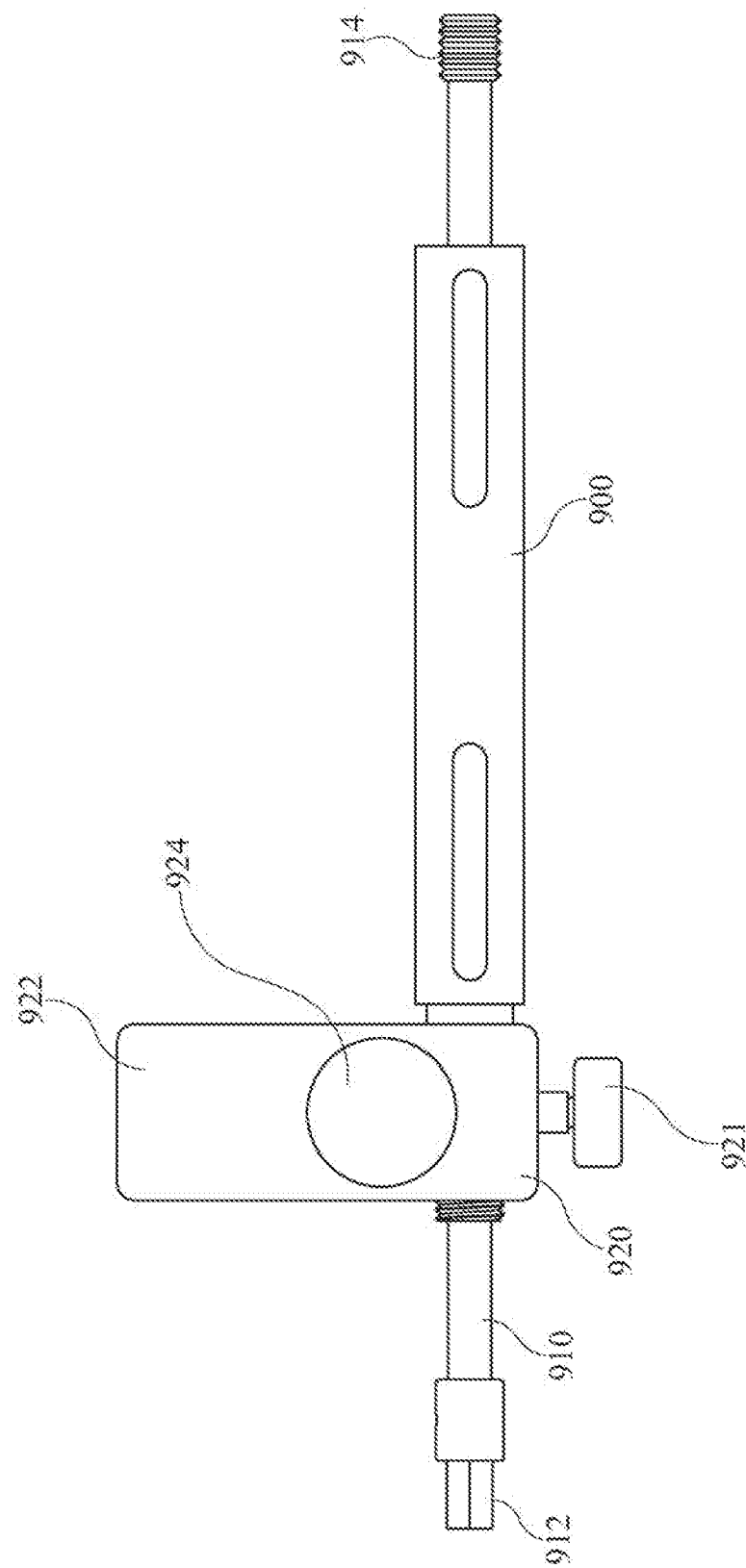
FIG. 73 is a side view of an extension arm in accordance with one embodiment of the present invention.

FIGS. 70 and 71 depict an alternative embodiment of bone graft plunger 820, wherein angled tip 822 and shaft 824 are comprised of a single piece of memory metal that is curved to approximate the curvature of an anterior portion of disc space 2 in its relaxed shape. In this embodiment of the invention, bone graft plunger 820 is straightened to insert its distal tip 822 into funnel 800 and inserter tube 100, and it assumes its curved or relaxed shape when inserted into disc space 2.

Referring now to FIGS. 72-79, and in accordance with a constructed embodiment of the invention, an extension arm 900 is depicted for securing various components of the present system 10 to a plurality of pedicle screws 9 that are secured to a human spine by known-in-the-art surgical techniques. With specific reference to FIGS. 72 and 73, extension arm 900 comprises an arm body 902 that engages a central threaded rod 910 having a proximal end that may be turned by, for example, a wrench, nut driver, or like mechanical device. Rod 910 also includes a distal end 914, which is shown in the present embodiment having a plurality of helical threads thereon for engaging a pedicle screw having complementary threads therein.

An adjustable clamp 920 is secured to extension arm body 902 by a conventional adjustment knob 921 and concomitant threaded member (not shown). Clamp 920 includes a pair of spaced clamp arms 922 extending outwardly from body 902 that are adjustable with respect to one another by conventional means, for example a clamp adjustment knob 924 secured to a threaded member 926, that engages complementary threads 928 in each clamp arm. Extension arm 900 is secured to a complementary pedicle screw by rotating central rod 910 to engage distal end 914 with the pedicle screw. Clamp 920 is then adjusted to position arms 922 to secure, for example, inserter tube 100 to extension arm 900 in a precise location for delivery of inter-body device 20.

Figure 74:
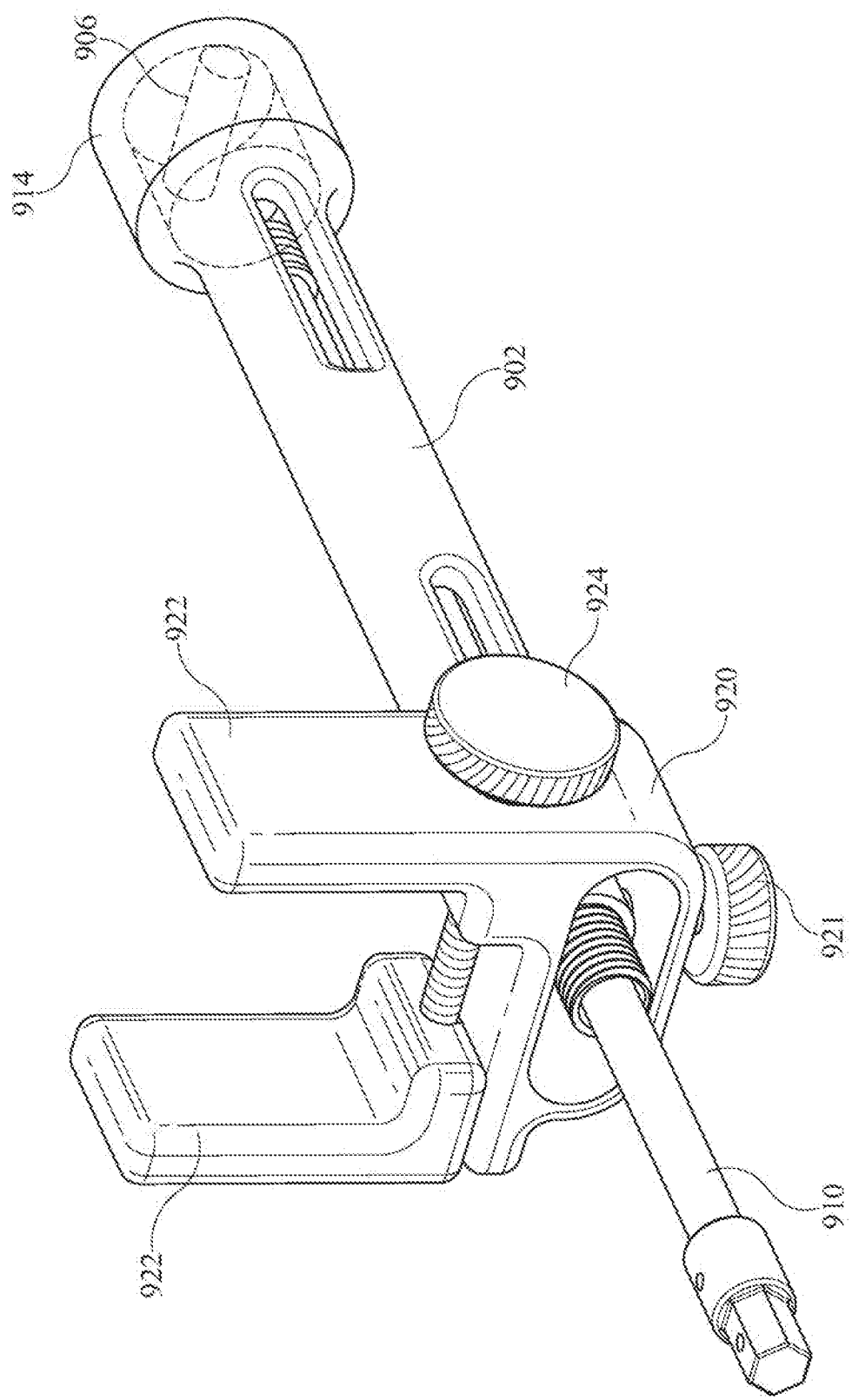
FIG. 74 is a perspective view of an extension arm in accordance with one embodiment of the present invention.
Figure 75:
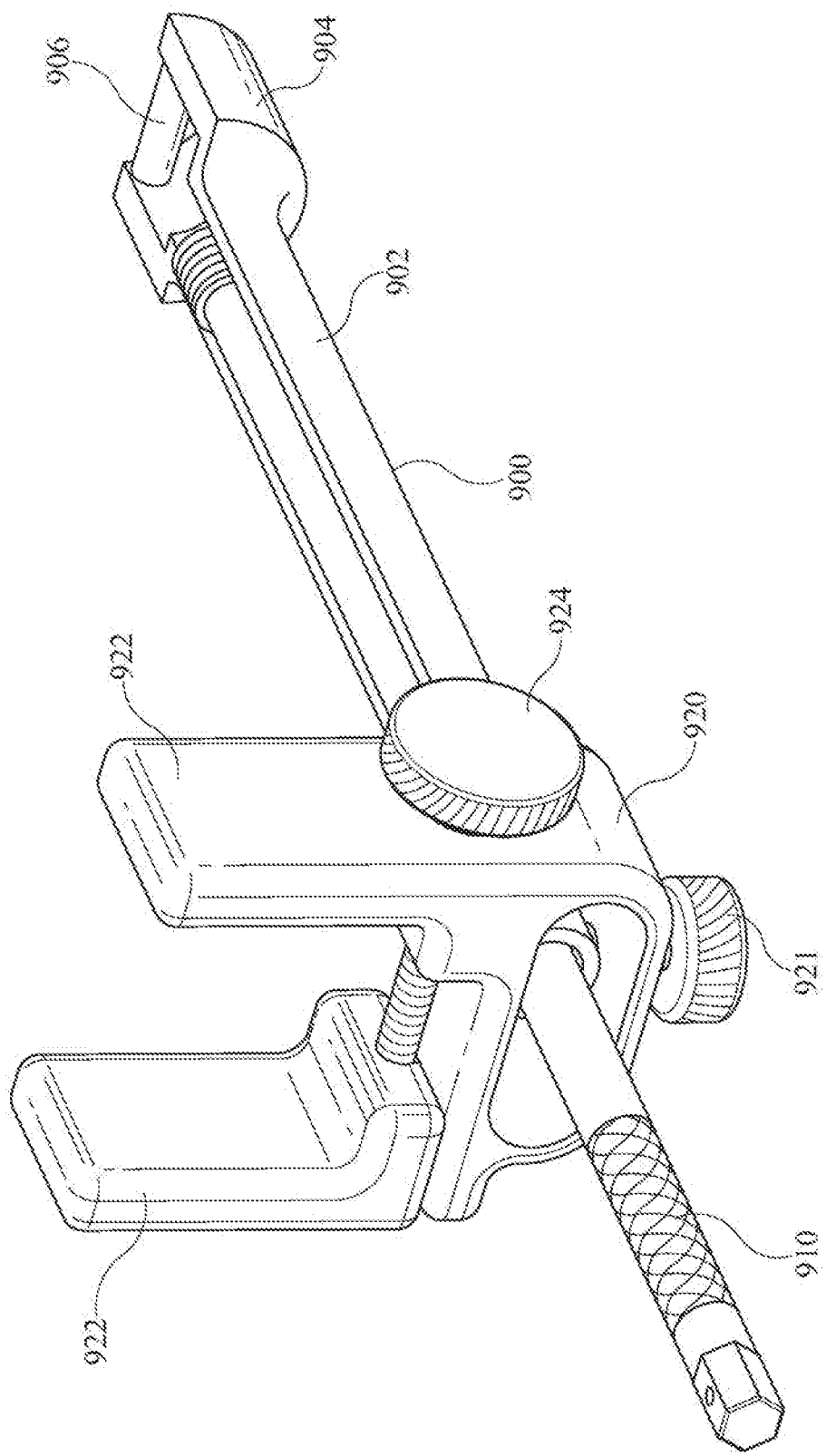
FIG. 75 is a perspective view of an extension arm in accordance with one embodiment of the present invention.

FIGS. 74 and 75 depict additional embodiments of extension arm 900 that include an extension arm body 902 that has a distal end 914 having a transverse pin 906 secured thereto for engaging a complementary hook of a pedicle screw (not shown).

Figure 76:
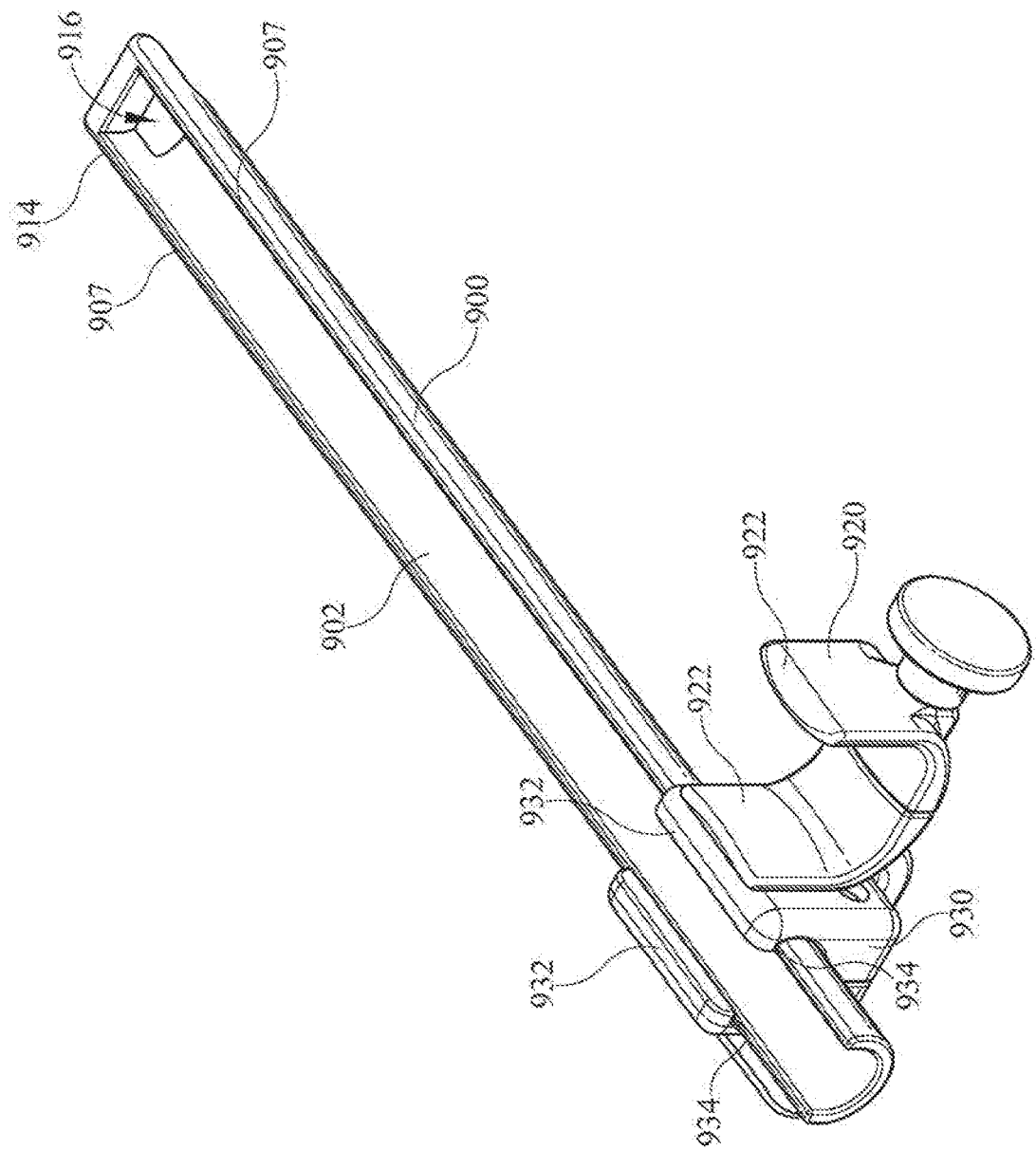
FIG. 76 is a perspective view of an extension arm in accordance with one embodiment of the present invention.
Figure 78:
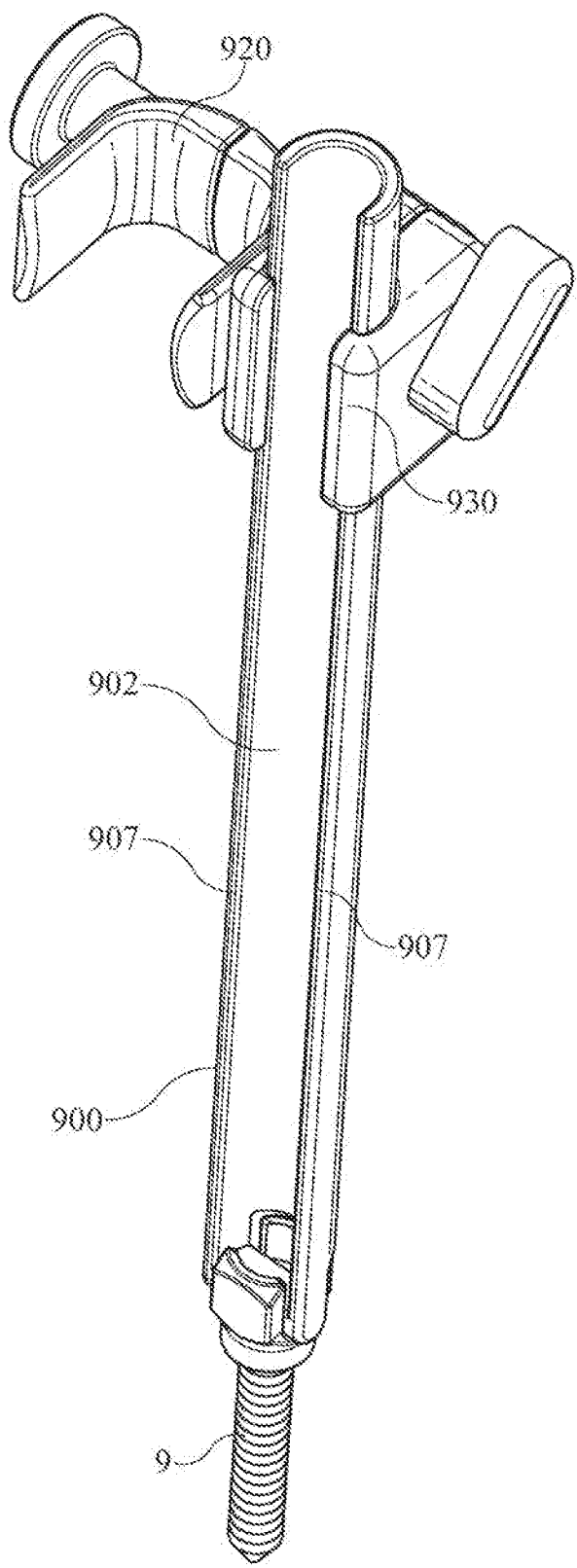
FIG. 78 is a perspective view of an extension arm in accordance with one embodiment of the present invention.

FIGS. 76 and 78 depict an alternative embodiment of extension arm 900 having a body 902 that is shaped like an elongated channel, having a pair of spaced edges 907 along its length. Distal end 914 includes a cut-out portion 916 that engages a head of a pedicle screw 9, as shown in FIG. 78. Clamp 920 is secured to a clamp guide 930 that includes a pair of spaced arms 932, each having a groove 934 therein for engaging edges 907 of extension arm 900 body 902. In this embodiment of the invention, clamp guide 930 arms 932 slide onto body 902 edges 907, thereby providing a clamp guide 930 and claim 920 that is slidable along the length of extension arm body 902.

Figure 77:
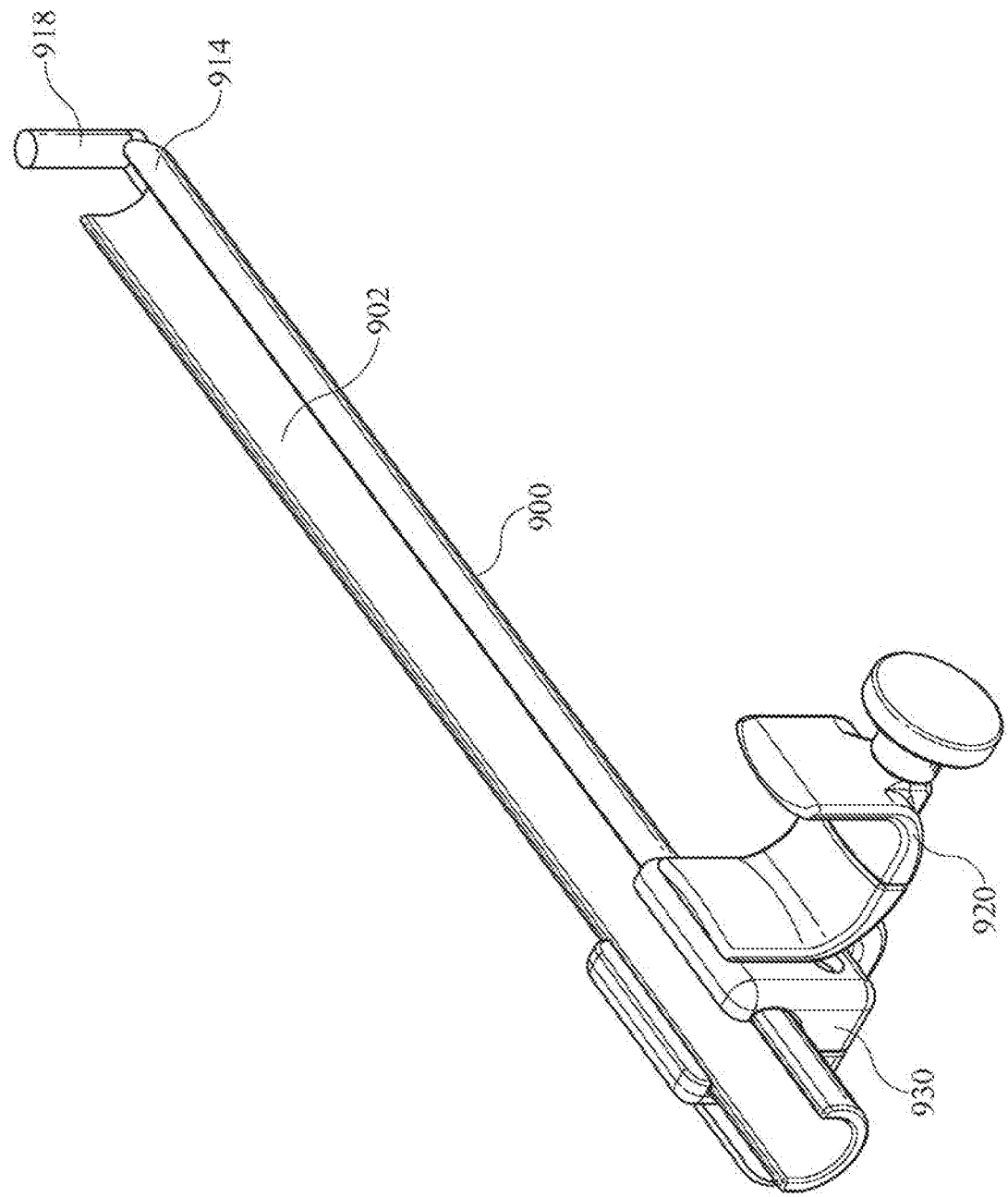
FIG. 77 is a perspective view of an extension arm in accordance with one embodiment of the present invention.
Figure 79:
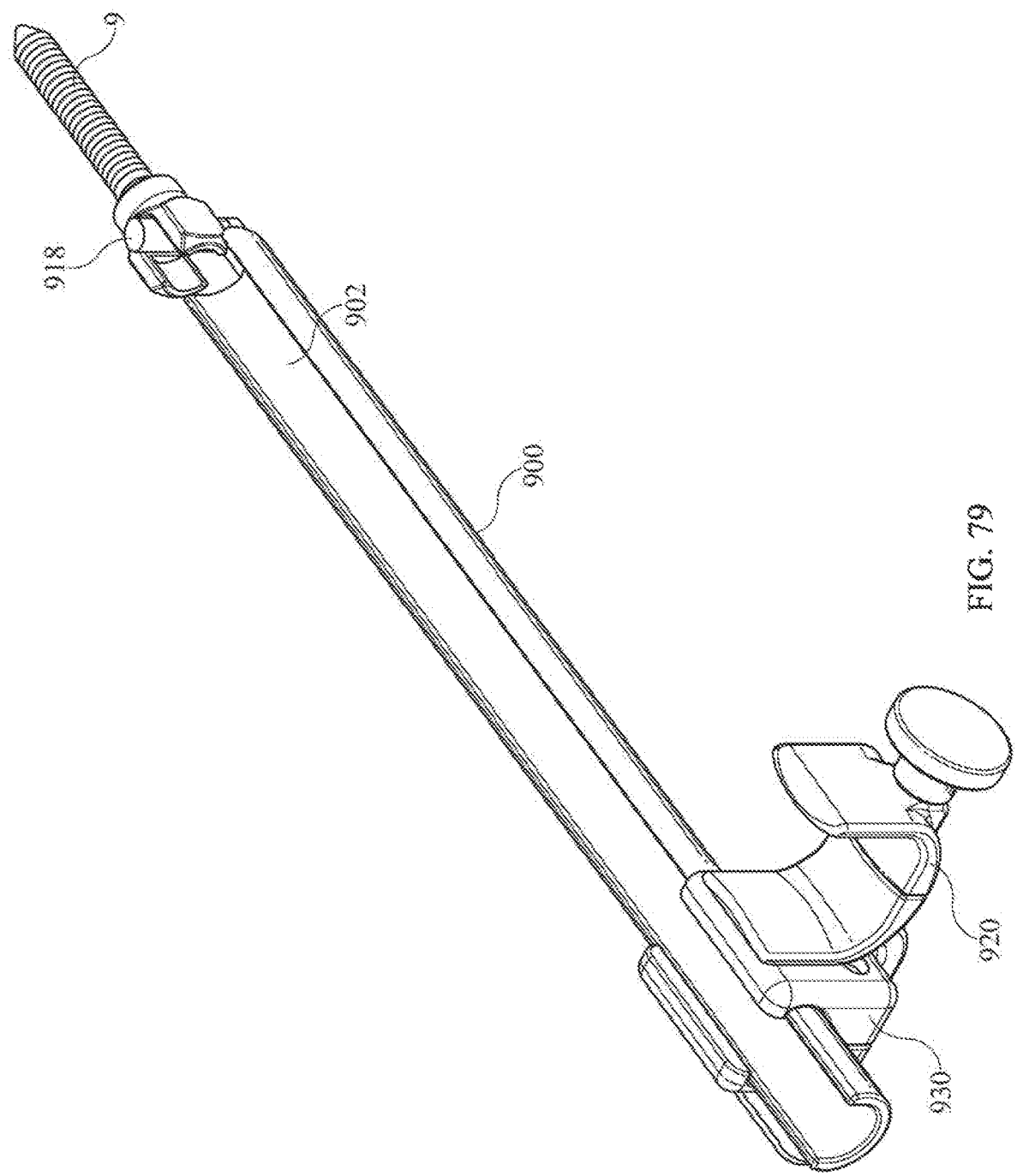
FIG. 79 is a perspective view of an extension arm in accordance with one embodiment of the present invention.

FIGS. 77 and 79 depict a similar extension arm embodiment to those shown in FIGS. 76 and 78, except that distal end 914 includes a vertical pin 918 that engages an aperture in pedicle screw 9, as best seen in FIG. 79.

Figure 80:
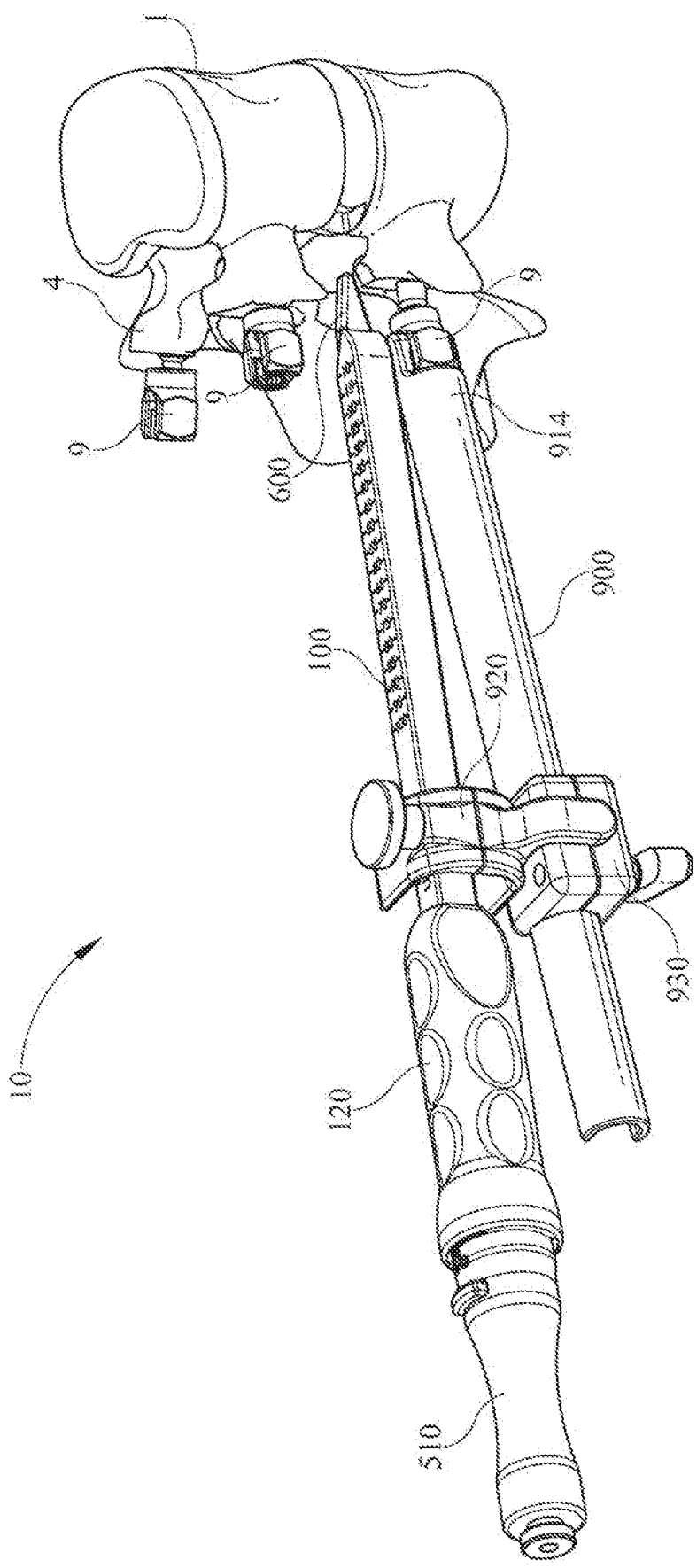
FIG. 80 is a perspective view of the system of the present invention in place in the environment of a human spine in accordance with one embodiment of the present invention.

FIG. 80 depicts the system 10 of the present invention secured to vertebrae 4 of spine 1 in an exemplary fashion. A plurality of pedicle screws are secured to spine 1 in a conventional fashion, as is known to one of ordinary skill in the art. Extension arm 900 is secured to pedicle screw 9 at its distal end 914. Clamp 920 of extension arm 900 is positioned via clamp guide 930 to engage handle 120 of inserter tube 100. Inserter tube 100 is positioned to be inserted through the annulotomy into disc space 2. Finally, trial handle 510 is secured to bullnose 600 and inserted through inserter tube 100.

In operation, the present system 10 and the components thereof may be employed by a surgeon to effect disc replacement in the following fashion. Initially, a surgeon makes a longitudinal midline incision in the area of pathology, through skin, subcutaneous tissue and fascia. Radiologic confirmation of vertebral level is then obtained through conventional radiographic techniques. Next, the lumbar spine is exposed through subperiosteal dissection, extending exposure only to the base of the transverse processes to permit identification of the entry points for insertion of pedicle screws 9. If TLIF (transforaminal lumbar inter-body fusion) is planned in conjunction with posterolateral fusion, dissect to the tips of the transverse processes of the levels included in the fusion. Pedicle screws are then applied in the conventional manner, as is known to one of ordinary skill in the art.

Next, a total ipsilateral facetectomy is performed, using an osteotome or drill. Additional bony removal may be carried out using a Kerrison Rongeur or drill to create a bigger space for insertion of appropriate sized implants and instruments. At this point, a surgeon may perform any additional neural decompression, if the determination is made that the particular case requires it. The posterolateral corner of the annulus is exposed maximally to allow an annulotomy as far lateral as possible. Next, a 1 cm-wide annulotomy incision is made.

Once the above-mentioned preparatory steps are completed, a thorough discectomy is performed. It is desirable in one embodiment of the present invention to extend the discectomy to the contralateral half of the disc space to allow for placement of the longest inter-body device 20 possible and to maximize bony surface exposure for fusion to occur. If there is significant disc space 2 collapse, a complete discectomy may not be possible until disc space 2 distraction is complete.

Next, the surgeon distracts the disc space sequentially with conventional distraction instruments, for example distractors ranging in height from 6 mm to 16 mm, until a snug fit is achieved. The surgeon may note the insertion depth and the height of the distractor used since the insertion depth gauges the depth of disc space 2. The height of the distractor employed in this step will determine the height chosen for the box cutter 700, bullnoses 600, inserter tube 100, trial implants 400, and inter-body device 20.

Next, the surgeon may apply a conventional contralateral distractor to maintain disc height and perform any additional discectomy, as necessary to prepare disc space 2. In one embodiment of the invention, a surgeon may employ a standard Penfield Elevator to palpate the vertebral endplate and then feel the anterior edge of the vertebral body. Once the anterior edge is felt and the Penfield Elevator dips, then adequate discectomy up to the anterior annulus has been achieved.

With a known-in-the art nerve root retractor the surgeon next protects the exiting and traversing nerve roots. At this point, box cutter 700 is inserted to shave the posterior endplate by utilizing a box cutter head of the same size as the tallest distractor used to achieve a snug fit as discussed above. Box cutter head 708 height may be provided on the surface thereof. It also has markings indicating the distance from distal tip 710. The surgeon then decorticates the remaining endplate surfaces of the superior and inferior vertebral bodies to enhance formation of bony fusion.

In the next step, the surgeon secures the extension arm 900 loosely to the inferior pedicle screw 9. Trial handle 510 is next secured to an appropriately sized bullnose 610, with a tapered distal tip 610 and this assembly is inserted into an identically sized inserter tube 100. Bullnose 600 and inserter tube 100 heights may marked on the instruments, as necessary.

Next, the assembled bullnose 600 and inserter tube 100 is advanced into disc space 2 through the annulotomy, by directing inserter tube 100 distal end 100 five to ten degrees laterally. The assembly orientation is then slowly manipulated to 0 degrees in the sagittal plane, keeping inserter tube 100 as far lateral in disc space 2 as possible.

Once the above assembly is inserted to the desired depth (as determined from the distractor placement mentioned above, bullnose 600 is removed. The surgeon should note the insertion depth of inserter tube 100 by the markings on the superior, medial and inferior surfaces thereof to indicate the distance from distal tip 110.

Next, the surgeon assembles handle 510 with the correct sized bullnose 600 having a blunt tip 610. Again, bullnose 600 height may be marked on the surface of the main shaft. Next, bullnose 600 is inserted into inserter tube 100 by engaging inserter tube handle 120 with trial handle 510. In one embodiment of the invention, bullnose 600 having a tapered distal tip 610 extends 15 mm beyond the inserter tube distal aperture 110. Furthermore, bullnose 600 having a blunt distal tip 610 extends only 10 mm beyond inserter tube 100 distal tip 110. The surgeon advances the handle 510, bullnose 600, and inserter tube 100 assembly deeper into disc space 2 until bullnose 600 distal end 610 touches the anterior annulus thereof.

Next, the surgeon secures inserter tube 100 handle 120 to extension arm 900 and extension arm 900 distal end 914 is secured tightly to pedicle screw 9. Next, the surgeon can remove bullnose 600, while remembering that in this position, there is 10 mm of free space between inserter tube 100 distal tip 110 and the anterior annulus of disc space 2, to allow smooth deployment of the bullnose 600 having a blunt distal tip 610 and inter-body device 20 into the anterior disc space 2.

In the next step, the surgeon assembles handle 510 to the determined trial implant 400 height size. Each trial implant 400 may be marked with its length and height to facilitate assembly in the operating room. Through inserter tube 100, the surgeon next sequentially attempts to deploy three different trial implant 400 lengths (of the chosen trial implant 400 height), starting with the shortest (for example, 20 mm), then with an intermediate (for example, 25 mm) to the longest (for example, 30 mm). Saline may be used to lubricate the inserter for easier deployment.

The longest trial implant 400 length that can be successfully deployed into disc space 2 determines the inter-body device length to be used. After radiologic confirmation of satisfactory trial implant 400 position within disc space 2, remove trial implant 400 from disc space 2 and inserter tube 100.

In the next step, the surgeon secures handle 510 to the previously determined bullnose 600 height. At this stage, bullnose 600 having blunt distal end 610 will be employed to push inter-body device 20 through inserter tube 100. Each inter-body device 20 may be marked with its height and length to facilitate assembly. The inter-body device should be visually inspected by the surgeon for any damage. Next, a standard No. 2 suture 3 may be looped through hitch 50 of inter-body device 20. Suture 3 will allow the inter-body device 20 to be retrieved, if necessary, before complete passage through inserter tube 100. If inter-body device 20 is retrieved it should again be visually inspected for any damage.

The surgeon next fills apertures 46 within the inter-body device 20 cans 30 with morselized bone graft material. The relief area 38 between cans 30 and anterior wall 40 should not be filled to permit inter-body device 20 bridge 60 and cans 30 to flex. Doing so may affect the proper deployment of inter-body device 20 through inserter tube 100 and disc space 2.

Nest, the surgeon inserts inter-body device 20 through inserter tube 100 with the concavity of the inter-body device 20 directed medially and hitch 50 directed proximally. Inserter tube 100 medial and lateral sides may be labeled on the instrument for ease of insertion. The surgeon positions looped suture 3 into the suture groove in inserter tube 100 handle 120. The groove in inserter tube 100 handle 120 should align with suture guide groove 612 in bullnose 600. This prevents suture 3 from being caught between the sliding surfaces of bullnose 600 and the interior wall of inserter tube 100.

Using the bullnose 600 handle 510 the surgeon next advances the inter-body device 20 along inserter tube 100 and into anterior disc space 2. Saline may be used to lubricate inserter tube 100 for easier deployment. Once inserted, the surgeon verifies device 20 position by conventional radiography.

Next, the surgeon pulls looped suture 3 out of hitch 50 and inserter tube 100. Inserter tube 100 is next unlocked from extension arm 900 and handle 510, and bullnose 600 and inserter tube 100 assembly is withdrawn from disc space by approximately 10 mm in preparation for application of bone graft material. A slap hammer may be used to aid withdrawal. This assembly is then secured back to extension arm 900 utilizing clamp 920.

Next, the surgeon disengages handle 510 from inserter tube 100 handle 120 and pulls bullnose 600 out of inserter tube 100. Bone graft funnel 800 is then placed on the proximal end of inserter tube 100 handle 120. The surgeon then assembles the appropriate size bone graft plunger 820 tip 822 to handle 510. In one embodiment of the invention, each plunger tip 822 is marked with its height. Next, the surgeon deposits morselized bone graft material 7 into bone graft funnel 800, and pushes it down inserter tube 100 using the bone graft plunger 820. Once this step is completed, the bone graft funnel 800 is disconnected from inserter tube handle 120. The bone graft material 7 may then be pushed further into disc space 2 using bone graft plunger 820 again.

Finally, the surgeon may remove the bone graft plunger 820, disconnect extension arm 900 from pedicle screw 9, and remove extension arm 900 and inserter tube 100 as an assembled unit to complete the procedure.

While the present invention has been shown and described herein in what are considered to be the preferred embodiments thereof, illustrating the results and advantages over the prior art obtained through the present invention, the invention is not limited to those specific embodiments. Thus, the forms of the invention shown and described herein are to be taken as illustrative only and other embodiments may be selected without departing from the scope of the present invention, as set forth in the claims appended hereto.

The invention claimed is:

1. A system for inserting an inter-body device into a spinal disc space, the system comprising:
    an inserter tube having a distal region, the distal region positionable within the spinal disc space;
    a bullnose positionable within the inserter tube; and
    an inter-body device advanceable through the inserter tube, the inter-body device having cans spaced apart from each other and connected to each other by a flexible bridge, each can having an upper surface and a lower surface for contacting adjacent vertebrae, each can having a first wall spaced in opposition to the flexible bridge and a second wall disposed between the upper and lower surfaces, the inter-body device further including a relief area bounded by the first walls of the cans and the flexible bridge, wherein at least one of the cans is configured to be compressed into the relief area as the inter-body device is advanced through the inserter tube and into the spinal disc space with the bullnose.

2. The system of claim 1, wherein the inserter tube includes a curved portion at distal end portion of the inserter tube that guides the inter-body device into the spinal disc space.

3. The system of claim 2, wherein the curved portion enables the inter-body device to move from an uncompressed position to a compressed position, wherein at least one of the cans of the inter-body device is compressed into the relief area when the inter-body device is positioned in the compressed position.

4. The system of claim 1, further including a bone graft plunger configured to advance bone graft material through the inserter tube and into the spinal disc space.

5. The system of claim 1, further including a trial implant coupled to a trial handle and selectively advanceable through the inserter tube.

6. The system of claim 5, wherein the trial handle includes an articulating arm, the trial implant pivotally secured to the articulating arm.

7. The system of claim 1, wherein the inter-body device further includes a hitch, and a suture is selectively attached to the hitch to enable the inter-body device to be pulled proximally through the inserter tube.

8. The system of claim 7, wherein the inserter tube includes a suture groove positioned to guide the suture through the inserter tube as the inter-body device is deployed from the inserter tube.

9. The system of claim 8, wherein the bullnose defines a suture guide groove that aligns with the suture groove of the inserter tube.

10. The system of claim 1, wherein the inter-body device is formed of a single piece of material, wherein the flexible bridge is integral with the cans.

11. A system for inserting an inter-body device into a spinal disc space, the system comprising:
an inserter tube having a distal region, the distal region positionable within the spinal disc space;
a bullnose positionable within the inserter tube
a bone graft funnel configured to secure to a proximal end portion of the inserter tube; and
an inter-body device advanceable through the inserter tube, the inter-body device having spaced cans connected to each other by a flexible bridge, each can having an upper surface and a lower surface for contacting adjacent vertebrae, each can having a first wall spaced in opposition to the flexible bridge and a second wall disposed between the upper and lower surfaces, the inter-body device further including a relief area bounded by the first walls of the cans and the flexible bridge, wherein at least one of the cans is configured to be compressed into the relief area as the inter-body device is advanced through the inserter tube and into the spinal disc space with the bullnose.

12. A method for inserting an inter-body device into a spinal disc space, the method comprising:
positioning a distal region of an inserter tube into the spinal disc space;
inserting a bullnose into the inserter tube such that it engages an inter-body device disposed in the inserter tube to advance the inter-body device through the inserter tube; and
compressing cans of the inter-body device that are spaced apart from each other into a relief area of the inter-body device as the inter-body device is advanced through the inserter tube and into the disc space, the relief area bounded by a flexible bridge that connects the cans and a first wall of each can spaced in opposition to the flexible bridge, each can having an upper surface and a lower surface for contacting adjacent vertebrae, and each can having a second wall disposed between the upper and lower surfaces.

13. The method of claim 12, further including distracting the spinal disc space with a distractor.

14. The method of claim 13, further including applying a contralateral distractor to vertebrae adjacent to the spinal disc space to maintain a disc height of the spinal disc space.

15. The method of claim 14, further including inserting a box cutter instrument into the spinal disc space to shave a posterior endplate of the adjacent vertebrae.

16. The method of claim 15, further including deploying a first trial implant into the spinal disc space through the inserter tube, the first trial implant having a first length.

17. The method of claim 16, further including deploying a second trial implant into the spinal disc space through the inserter tube after removing the first trial implant, the second trial implant having a second length, the second length different than the first length.

18. The method of claim 17, further including selecting the inter-body device based upon one of the first and second lengths.

19. The method of claim 12, further including selectively threading a suture through a hitch of the inter-body device.

20. The method of claim 19, further including selectively pulling the suture away from the hitch when the inter-body device is positioned within the spinal disc space.

21. The method of claim 12, further including imaging the inter-body device while the inter-body device is positioned in the spinal disc space.

22. The method of claim 12, further including:
placing a bone graft funnel on a proximal end portion of the inserter tube;
depositing bone graft material into the bone graft funnel; and
advancing the bone graft material into the inserter tube utilizing a bone graft plunger until the bone graft material is positioned into the spinal disc space.

* * * * *